(12) United States Patent
Wildman et al.

(10) Patent No.: US 7,450,024 B2
(45) Date of Patent: Nov. 11, 2008

(54) ARTICLE LOCATING AND TRACKING APPARATUS AND METHOD

(75) Inventors: Timothy D. Wildman, Metamora, IN (US); Thomas M. Fleck, Batesville, IN (US); Carl W. Riley, Milan, IN (US); Richard J. Schuman, Cary, NC (US); Williams F. Collins, Columbus, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

(21) Appl. No.: 11/770,178

(22) Filed: Jun. 28, 2007

(65) Prior Publication Data
US 2007/0247316 A1  Oct. 25, 2007

Related U.S. Application Data

(60) Division of application No. 10/822,525, filed on Apr. 12, 2004, now Pat. No. 7,242,306, which is a continuation-in-part of application No. 10/141,457, filed on May 8, 2002, now Pat. No. 7,248,933.

(60) Provisional application No. 60/289,432, filed on May 8, 2001, provisional application No. 60/462,216, filed on Apr. 11, 2003.

(51) Int. Cl.
   *G08B 21/00* (2006.01)
(52) U.S. Cl. .................... 340/669; 340/573.1
(58) Field of Classification Search ............ 340/669, 340/573.1, 572.1, 568.1
   See application file for complete search history.

(56) References Cited

U.S. PATENT DOCUMENTS

| | | | |
|---|---|---|---|
| 2,976,419 A | 3/1961 | Menke et al. | |
| 3,439,320 A | 4/1969 | Ward | |
| 3,478,344 A | 11/1969 | Schwitzgebel et al. | |
| 3,696,384 A | 10/1972 | Lester | |
| 3,714,573 A | 1/1973 | Grossman | |
| 3,739,329 A | 6/1973 | Lester | |
| 3,805,227 A | 4/1974 | Lester | |
| 3,805,265 A | 4/1974 | Lester | |
| 3,988,724 A | 10/1976 | Anderson | |
| 4,151,407 A | 4/1979 | McBride et al. | |
| 4,216,462 A | 8/1980 | McGrath et al. | |
| 4,225,953 A | 9/1980 | Simon et al. | |
| 4,275,385 A | 6/1981 | White | |
| 4,598,275 A | 7/1986 | Ross et al. | |

(Continued)

FOREIGN PATENT DOCUMENTS

DE  101 27 156  12/2002

(Continued)

OTHER PUBLICATIONS

Great New Product: Infrared Locator, Teleconnect, Feb. 1986. cited by other.

(Continued)

*Primary Examiner*—Thomas J Mullen, Jr.
(74) *Attorney, Agent, or Firm*—Barnes & Thornburg LLP

(57) ABSTRACT

An activity based monitoring system is disclosed, the activity based monitoring system being configured to monitor a plurality of badges associated with a plurality of assets within a healthcare facility.

12 Claims, 26 Drawing Sheets

U.S. PATENT DOCUMENTS

| | | |
|---|---|---|
| 4,601,064 A | 7/1986 | Shipley |
| 4,649,385 A | 3/1987 | Aires et al. |
| 4,706,689 A | 11/1987 | Man |
| 4,728,928 A | 3/1988 | Shipley |
| 4,740,792 A | 4/1988 | Sagey et al. |
| 4,837,568 A | 6/1989 | Snaper |
| 4,843,640 A | 6/1989 | Juengel |
| 4,885,571 A | 12/1989 | Pauley et al. |
| 4,955,000 A | 9/1990 | Nastrom |
| 4,967,195 A | 10/1990 | Shipley |
| 4,979,217 A | 12/1990 | Shipley |
| 4,981,141 A | 1/1991 | Segalowitz |
| 4,990,892 A | 2/1991 | Guest et al. |
| 5,012,113 A | 4/1991 | Valentine et al. |
| 5,014,040 A | 5/1991 | Weaver et al. |
| 5,027,314 A | 6/1991 | Linwood et al. |
| 5,036,852 A | 8/1991 | Leishman |
| 5,038,800 A | 8/1991 | Oba |
| 5,051,741 A | 9/1991 | Wesby |
| 5,062,151 A | 10/1991 | Shipley |
| 5,119,104 A | 6/1992 | Heller |
| 5,153,584 A | 10/1992 | Engira |
| 5,214,421 A | 5/1993 | Vernon et al. |
| 5,218,344 A | 6/1993 | Ricketts |
| 5,231,991 A | 8/1993 | Nelson |
| 5,245,314 A | 9/1993 | Kah, Jr. |
| 5,266,944 A | 11/1993 | Carroll et al. |
| 5,291,399 A | 3/1994 | Chaco |
| 5,317,309 A | 5/1994 | Vercellotti et al. |
| 5,319,191 A | 6/1994 | Crimmins |
| 5,319,363 A | 6/1994 | Welch et al. |
| 5,341,412 A | 8/1994 | Ramot et al. |
| 5,351,149 A | 9/1994 | Crimmins |
| 5,363,425 A | 11/1994 | Mufti et al. |
| 5,374,921 A | 12/1994 | Martin et al. |
| 5,387,993 A | 2/1995 | Heller et al. |
| 5,390,238 A | 2/1995 | Kirk et al. |
| 5,396,224 A | 3/1995 | Dukes et al. |
| 5,402,469 A | 3/1995 | Hopper et al. |
| 5,412,715 A | 5/1995 | Volpe |
| 5,417,222 A | 5/1995 | Dempsey et al. |
| 5,421,177 A | 6/1995 | Sieber et al. |
| 5,426,425 A | 6/1995 | Conrad et al. |
| RE35,035 E | 9/1995 | Shipley |
| 5,455,851 A | 10/1995 | Chaco et al. |
| 5,458,123 A | 10/1995 | Unger |
| 5,461,665 A | 10/1995 | Shur et al. |
| 5,465,082 A | 11/1995 | Chaco |
| 5,471,404 A | 11/1995 | Mazer |
| 5,493,283 A | 2/1996 | Hopper et al. |
| 5,504,477 A | 4/1996 | Whitright et al. |
| 5,515,426 A | 5/1996 | Yacenda et al. |
| 5,525,967 A | 6/1996 | Azizi et al. |
| 5,534,876 A | 7/1996 | Erickson et al. |
| 5,541,585 A | 7/1996 | Duhame et al. |
| 5,548,637 A | 8/1996 | Heller et al. |
| 5,561,412 A | 10/1996 | Novak et al. |
| 5,572,195 A | 11/1996 | Heller et al. |
| 5,572,653 A | 11/1996 | DeTemple et al. |
| 5,576,952 A | 11/1996 | Stutman et al. |
| 5,588,009 A | 12/1996 | Will |
| 5,589,821 A | 12/1996 | Sallen et al. |
| 5,590,648 A | 1/1997 | Mitchell et al. |
| 5,594,786 A | 1/1997 | Chaco et al. |
| 5,600,108 A | 2/1997 | Newham |
| 5,621,384 A | 4/1997 | Crimmins et al. |
| 5,627,524 A | 5/1997 | Fredrickson et al. |
| 5,629,678 A | 5/1997 | Gargano et al. |
| 5,633,742 A | 5/1997 | Shipley |
| 5,635,907 A | 6/1997 | Bernard et al. |
| 5,640,002 A | 6/1997 | Ruppert et al. |
| 5,640,157 A | 6/1997 | Langeraar |
| 5,652,570 A | 7/1997 | Lepkofker |
| 5,682,139 A | 10/1997 | Pradeep et al. |
| 5,682,142 A | 10/1997 | Loosmore et al. |
| 5,686,888 A | 11/1997 | Welles, II et al. |
| 5,689,229 A | 11/1997 | Chaco et al. |
| 5,714,932 A | 2/1998 | Castellon et al. |
| 5,722,599 A | 3/1998 | Fries |
| 5,729,196 A | 3/1998 | Aljadeff et al. |
| 5,731,757 A | 3/1998 | Layson, Jr. |
| 5,732,401 A | 3/1998 | Conway |
| 5,732,711 A | 3/1998 | Fitzpatrick et al. |
| 5,742,233 A | 4/1998 | Hoffman et al. |
| 5,745,037 A | 4/1998 | Guthrie et al. |
| 5,745,272 A | 4/1998 | Shipley |
| 5,748,084 A | 5/1998 | Isikoff |
| 5,748,148 A | 5/1998 | Heiser et al. |
| 5,751,246 A | 5/1998 | Hertel |
| 5,754,125 A | 5/1998 | Pearce |
| 5,760,687 A | 6/1998 | Cousy |
| 5,767,788 A | 6/1998 | Ness |
| 5,771,003 A | 6/1998 | Seymour |
| 5,793,861 A | 8/1998 | Haigh |
| 5,815,566 A | 9/1998 | Ramot et al. |
| 5,818,617 A | 10/1998 | Shipley |
| 5,822,418 A | 10/1998 | Yacenda et al. |
| 5,822,544 A | 10/1998 | Chaco et al. |
| 5,825,283 A | 10/1998 | Camhi |
| 5,828,306 A | 10/1998 | Curran |
| 5,831,533 A | 11/1998 | Kanno |
| 5,835,907 A | 11/1998 | Newman |
| 5,838,223 A | 11/1998 | Gallant et al. |
| 5,838,472 A | 11/1998 | Welch et al. |
| 5,920,287 A | 7/1999 | Belcher et al. |
| 5,959,529 A | 9/1999 | Kail, IV |
| 6,009,333 A | 12/1999 | Chaco |
| 6,037,879 A | 3/2000 | Tuttle |
| 6,040,773 A | 3/2000 | Vega et al. |
| 6,091,332 A | 7/2000 | Eberhardt et al. |
| 6,097,301 A | 8/2000 | Tuttle |
| 6,100,804 A | 8/2000 | Brady et al. |
| 6,101,390 A | 8/2000 | Jayaraman et al. |
| 6,104,311 A | 8/2000 | Lastinger |
| 6,114,962 A | 9/2000 | Wiklof et al. |
| 6,118,379 A | 9/2000 | Kodukula et al. |
| 6,121,878 A | 9/2000 | Brady et al. |
| 6,127,928 A | 10/2000 | Issacman et al. |
| 6,130,612 A | 10/2000 | Castellano et al. |
| 6,131,067 A | 10/2000 | Girerd et al. |
| 6,133,832 A | 10/2000 | Winder et al. |
| 6,133,837 A | 10/2000 | Riley |
| 6,137,411 A | 10/2000 | Tyren |
| 6,137,412 A | 10/2000 | Herzer |
| 6,144,301 A | 11/2000 | Frieden |
| 6,147,592 A | 11/2000 | Ulrich et al. |
| 6,150,921 A | 11/2000 | Werb et al. |
| 6,154,139 A | 11/2000 | Heller |
| 6,177,861 B1 | 1/2001 | MacLellan et al. |
| 6,204,764 B1 | 3/2001 | Maloney |
| 6,204,765 B1 | 3/2001 | Brady et al. |
| 6,204,813 B1 | 3/2001 | Wadell et al. |
| 6,211,781 B1 | 4/2001 | McDonald |
| 6,211,790 B1 | 4/2001 | Radomsky et al. |
| 6,252,512 B1 | 6/2001 | Riley |
| 6,259,355 B1 | 7/2001 | Chaco et al. |
| 6,344,794 B1 | 2/2002 | Ulrich et al. |
| 6,353,413 B1 | 3/2002 | White et al. |
| 6,424,264 B1 | 7/2002 | Giraldin et al. |
| 6,433,690 B2 * | 8/2002 | Petelenz et al. .......... 340/573.1 |
| 6,445,299 B1 * | 9/2002 | Rojas, Jr. ................ 340/573.1 |
| 6,524,239 B1 | 2/2003 | Reed et al. |
| 6,997,882 B1 * | 2/2006 | Parker et al. ................ 600/534 |
| 7,242,306 B2 | 7/2007 | Wildman et al. |

| | | | |
|---|---|---|---|
| 7,248,933 | B2 | 7/2007 | Wildman |
| 2002/0057203 | A1 | 5/2002 | Borders et al. |
| 2002/0165733 | A1 | 11/2002 | Pulkkinen et al. |
| 2002/0183979 | A1 | 12/2002 | Wildman |
| 2003/0045279 | A1 | 3/2003 | Shostak |
| 2003/0073434 | A1 | 4/2003 | Shostak |
| 2003/0149526 | A1* | 8/2003 | Zhou et al. .................. 701/213 |

FOREIGN PATENT DOCUMENTS

| | | |
|---|---|---|
| GB | 2 193 359 | 2/1988 |
| GB | 2 230 365 | 10/1990 |
| GB | 2 265 038 | 9/1993 |
| WO | WO 92/09178 | 5/1992 |

OTHER PUBLICATIONS

T.H. Ooi, "Low Cost RF Identification and Locating System," IEEE Trans. On Consumer Electronics, vol. 35 No. 4, Nov. 1989, pp. 831-839. cited by other.

United Identifications Systems Corp., Infra-Com, 1989. cited by other.

The Computer for the 21.sup.st Century, Mark Weiser, Scientific American, Sep. 1991. cited by other.

Keeping Track of Alzheimer and Dementia Prone Patients Just Got Easier, Security Tag Systems, Inc., 1991. cited by other.

The Clock with Sekurmed, 1991. cited by other.

Infant Monitoring System, Sekurmed. cited by other.

Voice Gadgets Aid Mercy, The News-Review; Jun. 22, 2003. cited by other.

* cited by examiner

ARTICLE LOCATING AND TRACKING APPARATUS AND METHOD

RELATED APPLICATIONS

This application is a divisional of U.S. patent application Ser. No. 10/822,525, filed Apr. 12, 2004, now U.S. Pat. No. 7,242,306, which is a continuation-in-part of U.S. patent application Ser. No. 10/141,457, filed May 8, 2002, now U.S. Pat. No. 7,248,933, which claims the benefit of U.S. Provisional Application Ser. No. 60/462,216, filed Apr. 11, 2003 and which also claims the benefit of U.S. Provisional Patent Application Ser. No. 60/289,432, filed May 8, 2001, the disclosures of the above applications are hereby expressly incorporated by reference herein.

BACKGROUND AND SUMMARY OF THE INVENTION

The present invention is related to monitoring activities and more particularly monitoring activities of persons and equipment in a healthcare environment.

Caregivers such as nurses and other staff in a hospital ward, hospital wing, or other healthcare facility generally work under high pressure, high stress and long hours. These caregivers should be highly responsive to patient needs, in non-emergency as well as emergency situations. Due to ever-increasing costs of healthcare and other economic practicalities, efficient deployment of the caregivers in a healthcare facility is desired, particularly at night when the number of caregivers is typically maintained at a minimum. Nevertheless, optimizing efficiency is of secondary importance relative to the primary objective of providing a high level of healthcare.

One approach to maximizing the efficiency of caregivers such as nurses in a hospital facility involves the use of a location and identification system to continuously monitor the location of the caregivers. For instance, U.S. Pat. No. 4,275,385 to White, which is incorporated herein by reference, discloses a personnel locating system where individuals to be located wear transmitters, and each transmitter transmits a signal which corresponds to the identity of the wearer. This information is relayed to and displayed at a central control unit. The information may also be displayed at remote terminals, used to control access to equipment or locations, or conveyed via a telephone interface to a telephone switching network to call the nearest telephone or to page the wearer of the transmitter. Additionally, newer communications systems provide even more than the relatively simple locating and telephoning features disclosed in White. For example, U.S. Pat. No. 5,561,412 to Novak et al., U.S. Pat. No. 5,699,038 to Ulrich et al., and U.S. Pat. No. 5,838,223 to Gallant et al., all of which are incorporated herein by reference, disclose the use of communications systems that integrate several aspects of personnel and equipment locating, call/code enunciation, and equipment status information.

As alluded to above, caregiver (e.g., nurse) to patient ratios continue to decline due to increasing economic pressures. Many healthcare facilities are exploring ways to reduce the non-value added activities of the caregivers to maintain quality care while reducing the number of caregivers per patient. Computers hold promise for aiding the caregivers to work more efficiently by eliminating activities previously performed by caregivers and/or reducing the amount of time associated with the performance of caregiver activities. However, conventional uses of computers in the above locating and identification systems only supply the caregivers with information and at the most alarms indicating possible adverse events. Computer systems need to become aware of activities within the hospital environment if they are to reduce employee workload. To enable this evolution in computing technology, Activity Based Tracking ("ABT") is needed. ABT is, in a general sense, the real-time connectivity of information (i.e., location, time, device activity, etc.) to detect the occurrence of a specific activity for which a known response is acted upon by an automated system.

Generally speaking an ABT system performs better if the ABT system includes a locating and detection system with a relatively high location resolution. In other words, the instances in which the ABT system provides value to the caregiver are increased if the ABT system is able to determine the location of caregivers, patients, equipment, etc. (hereinafter, "assets") with high resolution. Current tracking/locating systems used in hospitals are based on IR/RF in which the location of the fixed receiver determines the location of the tagged object. Utilizing this strategy, to increase the locating resolution (e.g., to move from being able to determine which room a caregiver is in to being able to determine that the caregiver is next to a patient's bed), additional receivers with limited range may be employed.

In one exemplary embodiment a system for tracking a plurality of movable assets in a healthcare environment is provided comprising a plurality of badges and a locating system. Each of the plurality of badges including a transmitter, being adapted to be coupled to the asset, and being configured to transmit an identification signal identifying the badge. The locating system being configured to receive the identification signal from the respective badge and to determine a location of the asset in the healthcare environment including a height associated with the asset based at least in part on the identification signal. The locating system being further configured to determine if the height of the asset is an expected height.

In one exemplary method for monitoring an asset to determine if the asset has been dropped or has fallen, the method comprises the steps of providing a badge adapted to be coupled to the asset, the badge having an accelerometer configured to monitor a vertical acceleration of the asset and a transmitter; monitoring the vertical component of the acceleration of the badge; transmitting information regarding the vertical acceleration of the badge; determining if the vertical acceleration of the badge has exceeded a threshold value; and identifying the asset as having been dropped or as having fallen based on the vertical acceleration exceeding the threshold value.

In another exemplary embodiment, a system for tracking a plurality of movable assets in a healthcare facility is provided. The system comprising a plurality of badges, a locating system, and at least one portable device. Each of the plurality of badges including a transmitter, being adapted to be coupled to the asset, and being configured to transmit an identification signal identifying the badge. The plurality of badges including a first badge being associated with a first movable asset. The locating system being configured to receive the identification signal from the first badge and to determine a location of the first movable asset in the healthcare facility based at least in part on the identification signal received from the first badge. The at least one portable device including a controller, a display, a memory, an input device, and a transceiver. The portable device being configured to generate a request signal to be received by the locating system requesting the location of the first movable asset in the healthcare facility, to receive a location signal from the locating system indicating the location of the first movable asset, and to provide appropriate directions to a first location in the healthcare facility based on the location of the first movable asset.

In yet another exemplary embodiment, a system for tracking a plurality of movable assets in a healthcare facility is provided. The system comprises a plurality of badges, a locating system, and a virtual facility interface. Each of the plurality of badges including a transmitter, being adapted to be coupled to the asset, and being configured to transmit an identification signal identifying the badge. The plurality of badges including a first badge being associated with a first movable asset. The locating system configured to receive the identification signal from the first badge and to determine a location of the first movable asset in the healthcare facility based at least in part on the identification signal received from the first badge. The virtual facility interface including a display and an input device. The virtual facility interface presents a virtual facility including a map of the facility and representations of various assets each having a badge associated therewith, the representations being positioned within the virtual facility based on the location information determined by the locating system for each asset. At least the first asset including multiple representations including a first representation corresponding to a first status and a second representation corresponding to a second status.

In still a further exemplary embodiment, a system for tracking a plurality of movable assets in a healthcare environment is provided. The system comprising a plurality of badges and a locating system. Each of the plurality of badges including a transmitter and a displacement sensor, the badge being adapted to be coupled to the asset. The locating system including a plurality of transmitters positioned at fixed locations within the healthcare environment and a processor with an associated receiver. The processor configured to receive an identification signal from the respective badges. The plurality of transmitters configured to transmit identification signals identifying the transmitter. A first badge is configured to receive the transmitter identifying signals from the transmitters within range of the first badge, to transmit an identification signal to the processor of the locating system, the identification signal including identification information identifying the first badge and motion information collected by the first badge based on the displacement sensor. One of the processor and the first badge determines the location of the first badge based on the transmitter identifying signals received by the first badge.

In a further exemplary embodiment, a locating system is provided wherein the location of a user is determined based in part on the position of the user within the field of view of a camera and the focal length of the camera when the user is in focus. In a still further exemplary embodiment, a locating system is provided wherein a plurality of badges are detected by one or more steerable transceivers which generate an excitation signal of limited extent, the badges being configured to respond to the excitation signal.

Additional features and advantages of the present invention will be evident from the following description of the drawings and exemplary embodiments.

DETAILED DESCRIPTION OF EXEMPLARY EMBODIMENTS

Figure 1:
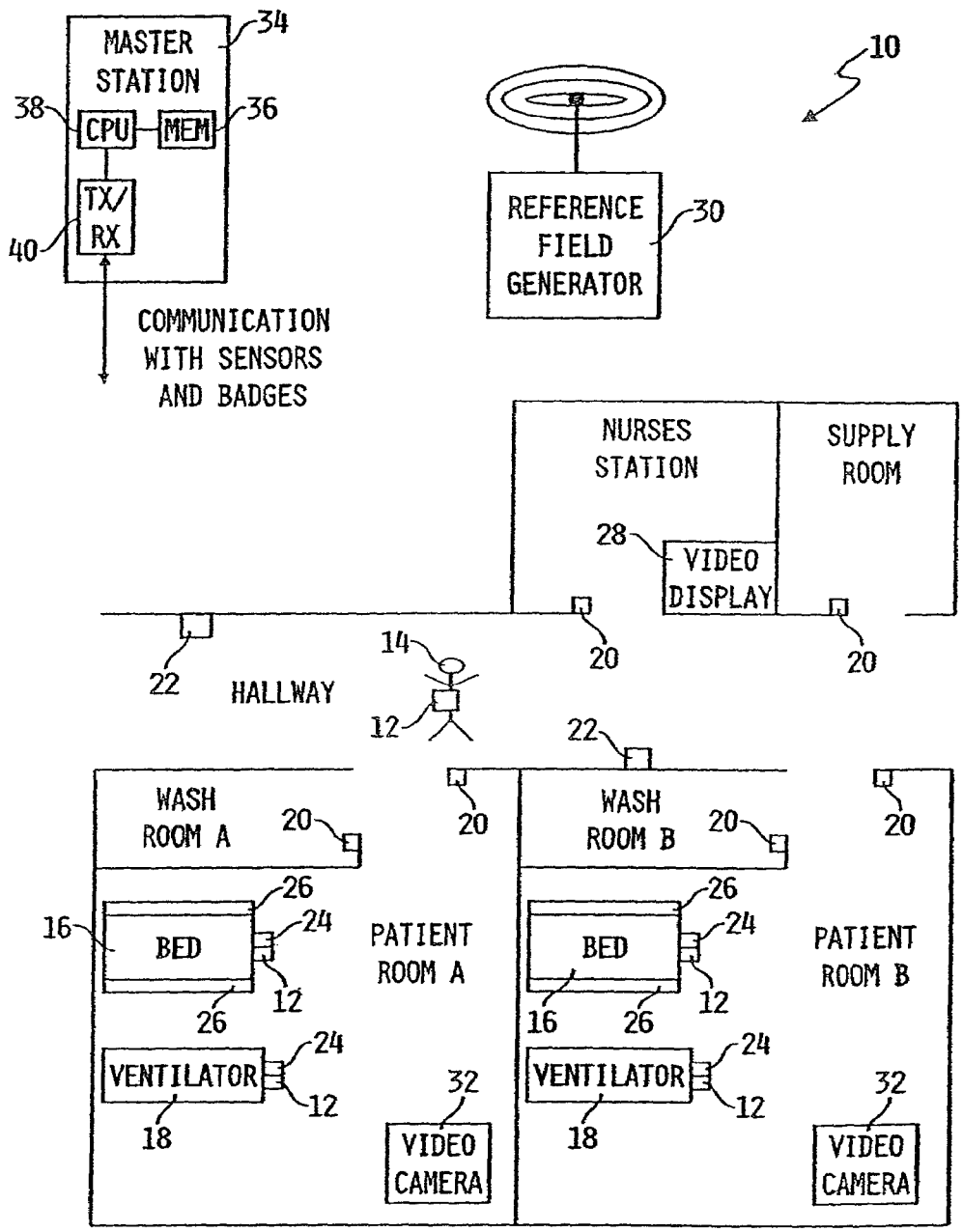
FIG. 1 illustrates an exemplary activity based tracking system that incorporates various features of the present invention.

While the invention is susceptible to various modifications and alternative forms, exemplary embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

FIG. 1 illustrates an exemplary activity based tracking (ABT) system 10 which incorporates various features of the present invention therein. In general, the ABT system 10 is operable to monitor activities and cause execution of actions in response to various activities. The exemplary ABT system 10 includes badges 12 used to tag persons 14 and equipment such as beds 16 and ventilators 18. As further described below, badges 12 may include passive RFID, active RF, active IR, or ultrasound transmitters, or other suitable transmitters configured to emit or generate an ID signal traveling in free space. The exemplary ABT system 10 also includes short range absolute reference position (ARP) sensors 20 operable to communicate with badges 12 and long range sensors 22 operable to communicate with badges 12. As further described below, sensors 20, 22 may include passive RFID, active RF, active IR, or ultrasound sensors, or other suitable sensors configured to receive an ID signal traveling in free space. The exemplary ABT system 10 further includes equipment sensors 24 operable to provide use and/or status information associated with equipment such as beds 16, ventilators 18, and bed side rails 26. The exemplary ABT system 10 also includes video displays 28, an optional reference field generator 30, video cameras 32, and a master station 34.

The master station 34 is generally operable to receive information from the badges 12 and the equipment sensors 24, process the received information, and cause some action to be taken in response to determining that the received information satisfies predefined criteria or rules. The master station 34 includes memory 36, a processor 38, a transceiver 40, and software stored in the memory 36. The software when executed by the processor 38 generally causes the master station 34 to monitor persons 14 and equipment and cause certain actions to be taken in response to activities of the persons 14 and equipment. More details concerning the types of activities monitored, the manner of monitoring the activities, and the types of actions taken in response to the monitored activities are described below with reference to FIGS. 4-8.

As illustrated, the exemplary master station 34 is essentially a centralized computing system that executes software that causes the master station 34 to implement appropriate logic for activity based tracking. However, the master station 34 may alternatively be implemented in a distributed manner with multiple computing systems working together to implement the logic. In particular, the master station 34 may be implemented with a server cluster or server farm comprising several computing systems. Moreover, the master station 34 may also incorporate computational power of hospital equipment distributed throughout the facility such as beds, monitoring devices, docking stations, etc. to distribute portions of the computational burden associated with the logic to many processors.

The transceiver 40 of the master station 34 is coupled to the ARP sensors 20 and long range sensors 22 via a computer network or direct wiring in order to receive and/or transmit information therebetween. Moreover, the transceiver 40 of an exemplary embodiment is also coupled to some of the equipment sensors 24 via a computer network or direct wiring in order to receive and/or transmit information therebetween. Alternatively, the transceiver 40 includes wireless transmitters and receivers in order to wirelessly communicate with some or all of the ARP sensors 20, long range sensors 22, and/or the equipment sensors 24.

The optional reference field generator 30 is generally operable to provide a reference field from which the badges 12 generate heading information. As described below, the exemplary badges 12 include magnetoresistive sensors that provide signals indicative of the sensors' orientation to a reference field such as Earth's magnetic field. The reference field generator 30 is typically configured to generate a stronger magnetic field than the Earth's magnetic field. As a result, the badges 12 used with the reference field generator 30 typically include a low cost magnetoresistive sensor that does not require tilt detection or tilt correction.

Figure 9:
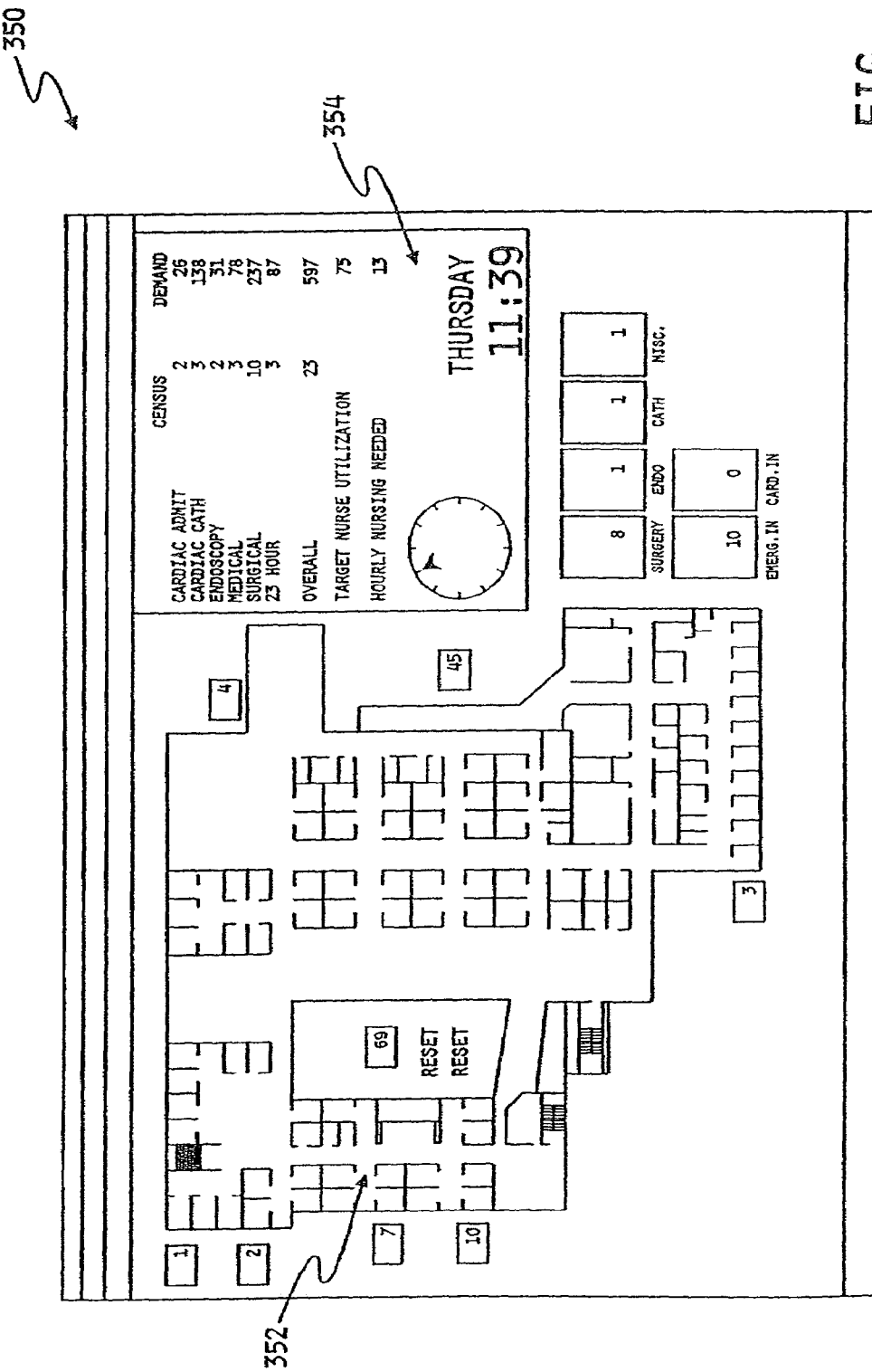
FIG. 9 illustrates an exemplary display generated by the activity based tracking system of FIG. 1.

The video displays 28 of the ABT system 10 are positioned at various locations throughout the facility (e.g., nurses' stations, hallways, utility rooms). The video displays 28 are operable to provide a graphical representation of the facility including the locations of tagged assets in the facility and the status of various equipment 15 in the facility as illustrated in FIG. 9. Moreover, in an exemplary embodiment, at least a portion of the video displays 28 are also operable to display representations of real-time streaming video. The video displays 28 are implemented using various display technologies such as televisions, computer CRTs, liquid crystal displays (LCDs), light emitting diodes (LEDs), and display panels. In an exemplary embodiment, handheld devices such as Palm™ Pilots, or Handspring™ Visors which are carried by the caregivers also include video displays 28.

The badges 12 are generally worn by or attached to assets, such as persons 14 (e.g., doctors, nurses, interns, orderlies, visitors, etc.) or equipment to be monitored (e.g., beds 16, ventilators 18, IV pumps, etc). The badges 12 and the sensors 20, 22 generally each include a receiver, a transmitter, a combination transmitter and receiver, a transceiver, or other receiving or transmitting mechanisms suitable for communicating information between the badges 12 and the sensors 20, 22. In an exemplary embodiment, the badges 12 are operable to send information such as a tag ID that uniquely identifies a given badge 12 and/or displacement information indicative of motion and heading of the badge to the sensors 20, 22. Moreover, the badges 12 of the exemplary embodiment are further operable to receive information such as an acknowledgment from the sensors 20, 22.

The sensors 20, 22 of the exemplary ABT system 10 generally include a receiver operable to receive information transmitted by badges 12. The sensors 20, 22 are also generally operable to forward the information received to the master station 34 and/or provide the master station 34 with a sensor ID that uniquely identifies the sensor 20, 22. The sensor ID enables the master station 34 to track the location of each tagged asset (i.e., person 14 or equipment) based upon which sensors 20, 22 received information from the badges 12 of tagged assets as the tagged assets move through the facility.

According to one embodiment of the invention, a person 14 may enter a floor of a hospital wearing a badge 12. The system recognizes that person 14 has entered the floor when person 14 moves within range of ARP sensor 20, whereupon the passive RFID transceiver of badge 12 is activated and transmits an ID associated with badge 12 (and person 14). The ID is received by a sensor 20 including an RFID interrogator located at a doorway entrance to the floor. As further explained herein, the network establishes an initial location point for person 14 by knowing the specific location of the RFID interrogator. The RFID interrogator may also be configured to transmit, for example, patient assignments to person 14, which are received by badge 12 and stored in badge memory 36. The system may then detect person 14 in a hallway of the floor with a sensor 22 including an active RF sensor for detecting ID signals transmitted by badge 12 with an active RF transmitter that periodically transmits the ID signal (e.g., every 5 seconds). As person 14 enters a patient room, the system may detect three signals from person 14 (i.e., an active RF signal indicating that person 14 is on the floor, an active IR signal indicating that person 14 is in a specific patient room, and a passive RFID signal indicating that person 14 is in the door entryway to the specific patient room). By installing RFID interrogators at different locations within such patient rooms, the system may accomplish increased resolution regarding the location of person 14 within the room.

In an exemplary embodiment, each badge 12 includes a passive RF transmitter which is fully or partially powered by an ARP sensor 20 when in close proximity to the ARP sensor 20 (e.g., within 3 feet). In response to being in close proximity to the ARP sensor 20, the passive RF transmitter of the exemplary badges 12 transmits the identification signal to the ARP sensors 20. For example, the RF transmitter of a badge 12 transmits the identification signal to an RF receiver of an ARP sensor 20 in the doorway of patient room A when the badge 12 passes through the doorway of the patient room A. The ARP sensor 20 then provides information identifying the particular badge 12 to the master station 34 and information identifying the particular ARP sensor 20 for further processing and recording. In an exemplary embodiment, the ARP sensor 20 includes an RF identification receiver or a limited focus IR receiver. In general, the ARP sensor 20 enables the master station 34 to establish a very specific location of a badge 12. More specifically, the ARP sensors 20 are used by the master station 34 to re-calibrate the location of the badges 12 as they pass within close proximity of the ARP sensors 20.

In one embodiment of the ABT system 10, visitors and patients are also provided with badges 12 to enable the master station 34 to monitor their movements through the facility. In such an embodiment, visitors and patients are given active badges which actively transmit an identification signal. In an alternative embodiment, visitors and patients are given passive badges which transmit an identification signal when in close proximity to one of the ARP sensors 20 located throughout the facility.

The badges 12 may also be attached to equipment (e.g., IV pumps, beds 16, ventilators 18, carts, diagnostic equipment, or the like) to be monitored by the ABT system 10 and generally enable the location of equipment to be tracked throughout the facility. As a result of providing the ABT system 10 with information concerning the location of equipment, the ABT system 10 causes actions to be executed based upon the location of the equipment and/or persons' interactions with such equipment.

The equipment sensors 24 are generally associated with equipment and generally enable the ABT system 10 to monitor the use and/or status of such equipment. For example, equipment sensors 24 are attached to the electrical plugs of the equipment to determine whether the equipment is drawing a current. In an exemplary embodiment, the badges 12 that are attached to certain equipment further include equipment sensors 24. The equipment sensors 24 enable the ABT system 10 to cause actions to be executed based upon use and/or status of the equipment. Furthermore, by reporting when the equipment is activated and de-activated, the equipment sensors 24 enable the hospital to charge patients for the actual amount of time the equipment was used instead of utilizing national averages based on the type of illness of the patient.

In an exemplary embodiment, the badges 12 and the sensors 20, 22 further include anti-collision technology that allows for information to be transferred between a single sensor 20, 22 and multiple badges 12 in a simultaneous or pseudo-simultaneous (e.g., TDMA, CDMA) manner. Use of anti-collision technology allows for several badges 12 to be detected at the same time by the same sensor 20, 22 thereby providing the ABT system 10 with the ability to identify persons 14 and equipment in close proximity to one another and accurately track their respective locations and activities.

Additional details concerning the structure and function of a suitable system for locating and tracking persons 14 and to support various other features of the present invention are disclosed in U.S. Pat. No. 5,561,412, the disclosure of which is hereby incorporated by reference. Other location and tracking systems are disclosed in U.S. Pat. No. 6,344,794 filed Jan. 7, 2000 and co-pending U.S. patent application Ser. No. 09/699,796, filed Oct. 30, 2000, now U.S. Pat. No. 6,727,818 the disclosures of which are hereby incorporated by reference. Additional location and tracking systems are disclosed in U.S. Pat. Nos. 4,275,385; 4,601,064; U.S. Pat. No. Re 35,035; U.S. Pat. Nos. 5,633,742; 5,745,272; 5,818,617; 5,119,104; 5,387,993; 5,548,637; 5,572,195; 5,291,399; 5,455,851; 5,465,082; 5,515,426; 5,594,786; 5,689,229; 5,822,418; 5,822,544; 5,699,038 and 5,838,223.

In an exemplary embodiment, the badges 12 are implemented in a manner similar to the badges described in U.S. Pat. Nos. 5,561,412, 6,344,794, and co-pending U.S. patent application Ser. No. 09/699,796 in which the location of a badge 12 is determined solely upon which sensors of the location and tracking system detect the badge 12.

Figure 2:
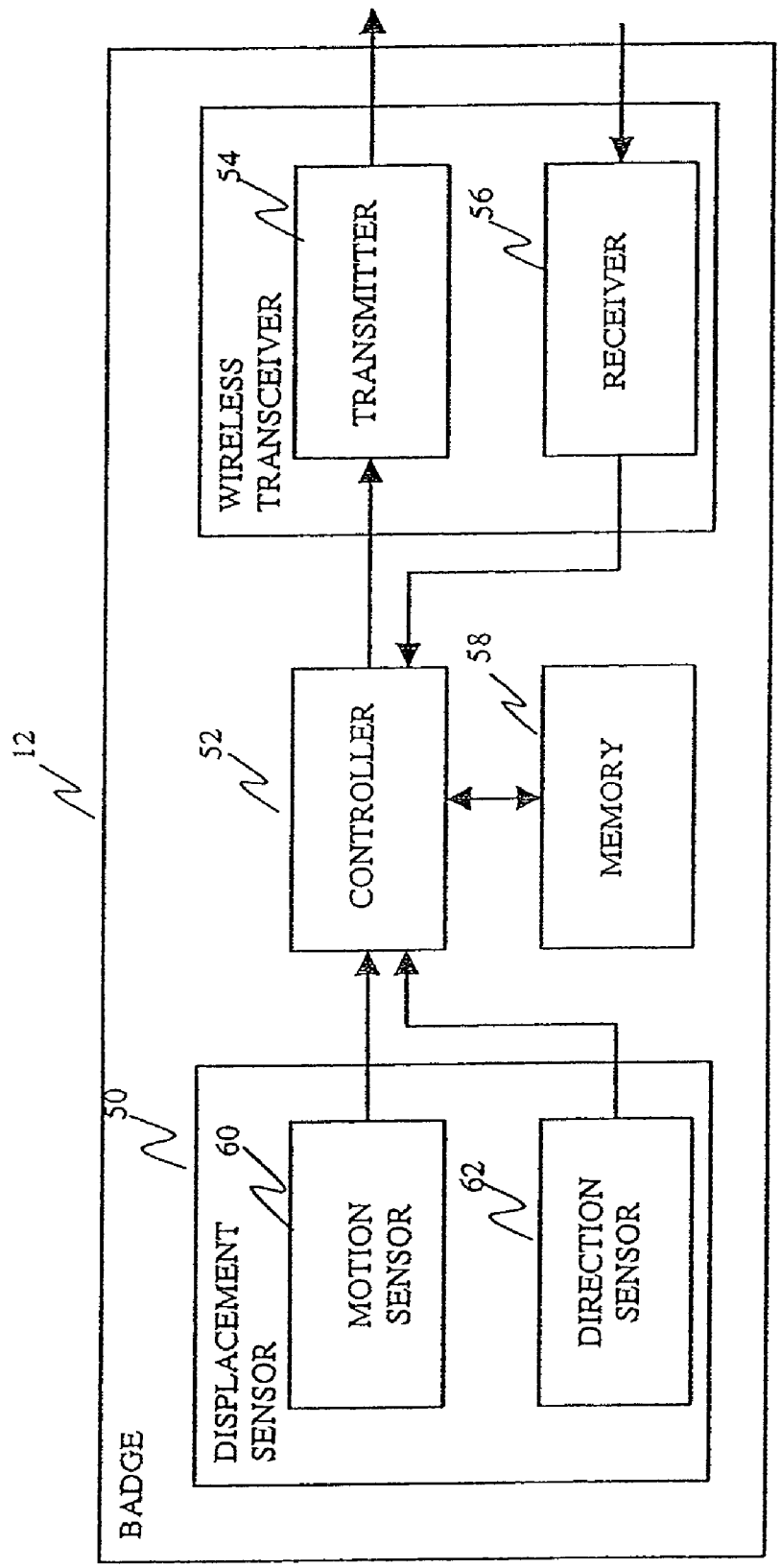
FIG. 2 illustrates an exemplary badge of the activity based tracking system shown in FIG. 1.

Alternatively, the badges 12 include components which aid in tracking the location of the badges 12 and thus enable a reduction in the number of sensors otherwise required to track the location of the badges 12 in a high resolution manner. As depicted in FIG. 2, the exemplary badges 12 include a displacement sensor 50, a controller 52, a transmitter 54, a receiver 56, and a memory 58. The displacement sensor 50 is configured to generate one or more signals the combination of which is indicative of a motion and a heading of a "tagged asset." As indicated above, tagged assets may include persons (e.g., doctors, nurses, orderlies, visitors, etc.), and equipment (e.g., a hospital bed 16, IV pumps, ventilators 18, heart monitors, medication containers, charts, portable televisions, etc.), or any other tangible thing desired to be located and/or tracked.

As depicted, the displacement sensor 50 generally comprises a motion sensor 60 and a direction sensor 62. The motion sensor 60 is generally operable to sense movement of the tagged object and generate one or more signals that in combination are indicative of the sensed movement. The motion sensor 60 includes a mono-axis, dual-axis, or tri-axis accelerometer which generates one or more signals that in combination are indicative of the dynamic acceleration (e.g., vibration induced acceleration) and/or static acceleration (e.g., gravity induced acceleration) of the tagged asset. In particular, the motion sensor 60 of the exemplary embodiment includes an ADXL202 accelerometer from Analog Devices which is a low cost, low power, complete two-axis accelerometer with a measurement range of ±2 g. The ADXL202 accelerometer measures both dynamic acceleration (e.g., vibration) and static acceleration (e.g., gravity) and generates a first Duty Cycle Modulated ("DCM") signal whose duty cycle (ratio of pulsewidth to period) is proportional to the acceleration in a first sensitive axis (e.g., x-axis) and a second DCM signal whose duty cycle is proportional to acceleration in a second sensitive axis (e.g., y-axis).

The following Analog Devices publications further describe the ADXL202 accelerometer and methods for relating the sensed accelerations to distances traveled: "ADXL202/ADXL201-Low cost ±2 g/±10 g Dual Axis iMEMS® Accelerometers with Digital Output" (Datasheet, Rev. B-4/99) and "Using the ADXL202 in Pedometer and Personal Navigation Applications," by Harvey Weinberg, the disclosures of which are hereby incorporated herein by reference.

The direction sensor 62 of the displacement sensor 50 is generally operable to generate one or more signals that in combination are indicative of the directional orientation or heading of the badge 12 with respect to a reference direction and therefore indicative of the direction traveled by the asset tagged with the badge 12. The direction sensor 62 of the exemplary embodiment includes a two-dimensional magnetoresistive field sensor such as the Philips KMZ52 sensor or two one-dimensional magnetoresistive field sensors such as the Philips KMZ51 which generate one or more signals indicative of the horizontal orientation of the badge 12 with respect to a reference direction such as magnetic north, true north, or some other direction defined by an associated reference field such as the Earth's magnetic field or an artificially generated field such as that generated by reference field generator 30. The exemplary direction sensor 38 further includes support electronics such as a flip coil driver and pre-amps which are used to calibrate the field sensors and interface the field sensors with the controller 32 as explained in Philips Semiconductor publication "Electronic Compass Design using KMZ51 and KMZ52, Application Note AN00022", dated Mar. 30, 2000.

As indicated above, the exemplary ABT system 10 includes a reference field generator 30 that enables the badge 12 to be implemented without tilt correction. However, in an alternative exemplary embodiment, the direction sensor 62 further includes mechanical or electrical gimbaling components that maintain the two sensitive axes of the field sensor in a horizontal plane (e.g., maintain an x-axis and a y-axis perpendicular with Earth's gravity). To support electronic gimbaling or tilt compensation, the direction sensor 62 includes a three-dimensional field sensor and a pitch-and-roll sensor. The three-dimensional field sensor includes three sensitive orthogonal axis sensors that generate one or more signals which in combination are indicative of a three-dimensional spatial orientation of the badge 12 with respect to a reference field such as Earth's magnetic field or a generated field such as that generated by the reference field generator 30. Further, the pitch-and-roll sensor generates one or more signals indicative of the orientation of the field sensor with respect to gravity. In particular, the pitch-and-roll sensor includes a two-dimensional accelerometer, such as the ADXL202 accelerometer described above, including two orthogonal axis sensors that generate one or more signals. These signals, in combination, are indicative of the static acceleration experienced by the badges 12 due to gravity.

The transmitter 54 of the badges 12 is coupled to the controller 32 to receive one or more signals indicative of information to be transmitted. Similarly, the receiver 56 is coupled to the controller 52 to provide the controller 52 with one or more signals indicative of information received. The transmitter 54 and the receiver 56 include infrared (IR), radio frequency (RF), and/or other wireless transmission and reception components which utilize one or more different transmission protocols. More specifically, as indicated above, the transmitter 52 includes a passive RF transmitter to transmit identification information such as a tag ID to the ARP sensors 20. Passive RF transmitters i) do not require battery power to transmit information, and ii) generally must pass close to an ARP sensor 20 in order to transmit information which insures a high resolution point for the absolute position.

The controller 52 in general controls the transmission and reception of information to and from the badges 12. In an exemplary embodiment, the controller 52 is implemented with a low cost microcontroller such as the MicroChip PIC16C54. Besides controlling the transmission and reception of information to and from the badges 12, the controller 52 also processes the displacement signals received from the displacement sensor 50 and stores displacement samples in the memory 58 that are representative of the motion and heading of the badges 12 as sensed by the displacement sensor 50. In particular, the controller 52 in an exemplary embodiment processes one or more motion signals from the displacement sensor 50 to obtain motion data that is indicative of the speed of the badge 12 and heading data indicative of the heading of the badge 12.

Figure 3A:
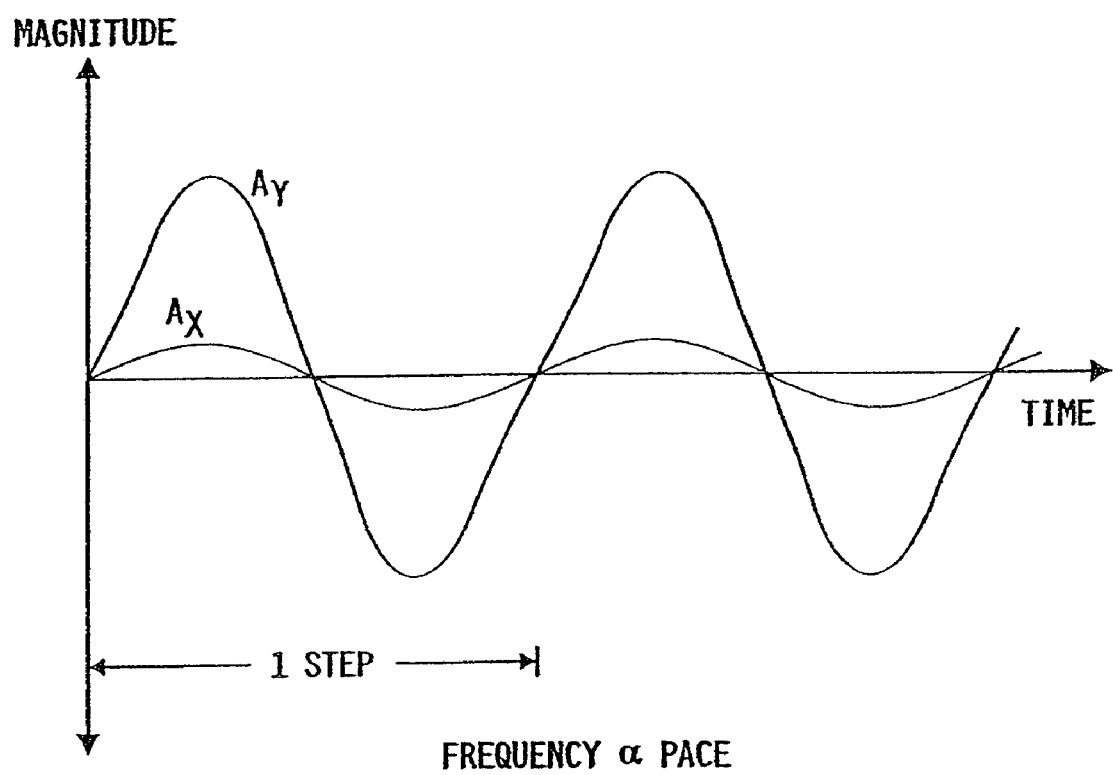
FIG. 3A illustrates typical movement of the badge shown in FIG. 2 when a object tagged with the badge is in transit.

FIG. 3A shows waveforms representing an exemplary vertical acceleration "$A_y$," and an exemplary horizontal acceleration, "$A_x$," of a person walking or running. In general, pedestrian travel is fairly rhythmic pursuant to the gait of the pedestrian. Accordingly, as the person walks or runs through the facility, the badge 12 attached to the person is accelerated vertically and horizontally in a generally periodic manner. Each step or stride taken by the person is detectable as the period of $A_y$. Thus, the frequency of $A_y$ is proportional to the number of steps taken by the caregiver per unit of time, which is proportional to the approximate pace at which the person walks or runs.

In the exemplary embodiment discussed above in connection with FIG. 2, the controller 52 receives one or more signals from the displacement sensor 50 that are indicative of the vertical acceleration $A_y$. In the exemplary embodiment, the controller 52 determines the approximate speed of movement of the person by processing the received signals to obtain the frequency of the vertical acceleration $A_y$ which is indicative of the speed of the person.

In the case of wheeled objects or objects on skids (e.g., hospital beds 16, carts, tables, etc.) the accelerations imparted to the tag or badge 12 attached to the object are fairly periodic in nature due to each revolution of the wheel(s) or vibrations of the skid(s). In an exemplary embodiment, a ridge or a bump is added to a wheel of a wheeled object in order to aid in the generation of a discernable amount of acceleration. In any event, although the relationship of the vertical acceleration $A_y$, horizontal acceleration $A_x$, and time may vary between different types of assets, and even between different pedestrians, the fairly periodic nature of the accelerations imparted to the badges 12 while the object is in motion are readily discernable via the appropriate signal processing algorithms. Moreover, the displacement sensor 50 may generate the signals based on other parameters that vary with the speed of movement of the object. For example, the displacement sensor 50 for wheeled assets may include a more conventional type speedometer that senses the rotation of the wheels and generates signals based upon the sensed rotation of the wheels.

Figure 3B:
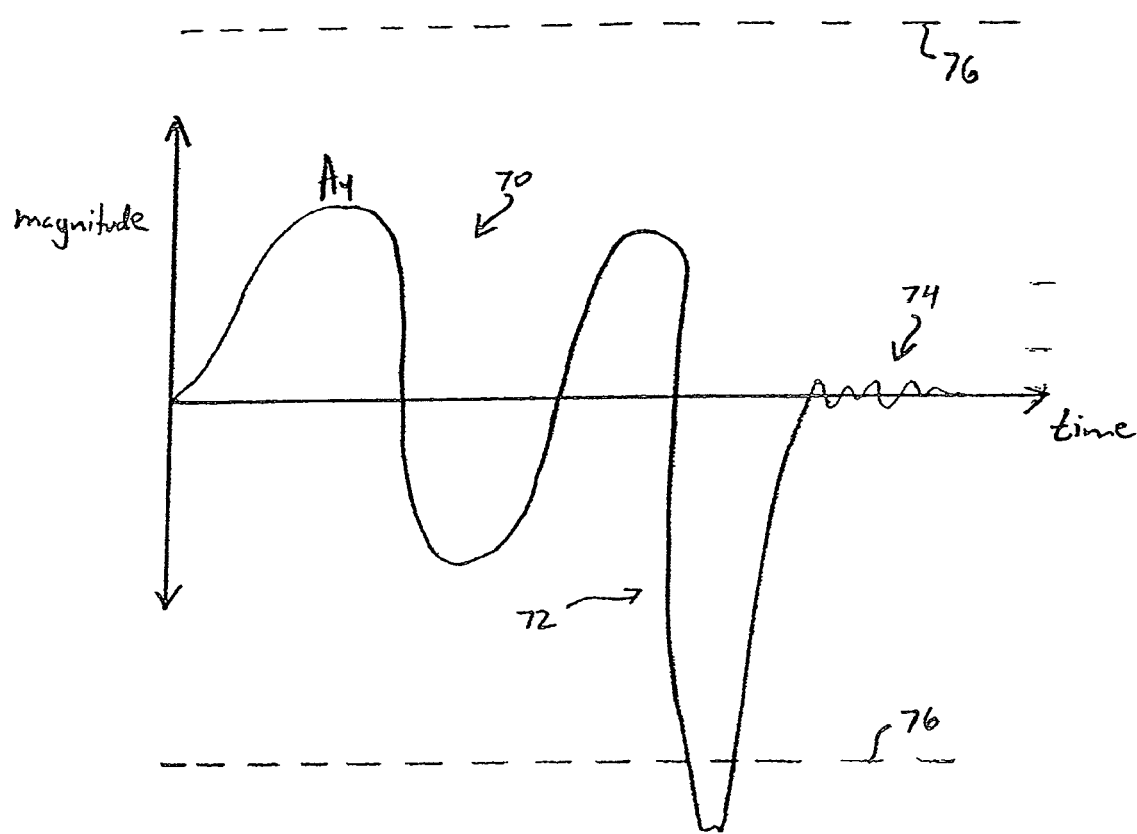
FIG. 3B illustrates typical movement in a vertical direction of the badge shown in FIG. 2 when an object tagged with the badge is in transit and the object subsequently experiences a fall.

In an exemplary embodiment, discussed above in connection with FIG. 2, controller 52 of badge 12 receives one or more signals from the displacement sensor 50 that are indicative of the vertical acceleration ($A_y$) of badge 12. Controller 52 monitors the vertical acceleration ($A_y$) to determine the speed of badge 12, as discussed above in connection with FIG. 3A, and to determine if the asset (person or equipment) associated with badge 12 has fallen or has been dropped. Assuming an asset associated with badge 12 falls or is dropped, the vertical acceleration ($A_y$) of badge 12 will exhibit a substantial change in the magnitude of the vertical acceleration ($A_y$) as illustrated in FIG. 3B. In one example, badge 12 includes a three-dimensional accelerometer and acceleration data in all three directions is monitored for substantial changes in magnitude.

Turning to FIG. 3B, the vertical acceleration ($A_y$) of a patient walking and subsequently falling is shown. A first portion 70 of the curve associated with vertical acceleration ($A_y$) exhibits the rhythmic pattern discussed above in connection with FIG. 3A indicative of a person walking. The first portion is followed by a second portion 72 corresponding to a substantial change in the magnitude of vertical acceleration ($A_y$) indicative of a fall. Assuming the patient is at least partially immobilized due to the fall, the vertical acceleration ($A_y$) associated with badge 12 will generally return to a baseline value as indicated by third portion 74. In one example, the vertical acceleration ($A_y$) in second portion 72 is indicative of a fall or drop if the vertical acceleration ($A_y$) exceeds a threshold amount 76. Threshold amount 76 in one example is the same for all assets. In another example, threshold amount 76 is different for at least one type of asset. Further, in an additional example, a characteristic of an asset is used in determining the threshold amount 76.

The vertical acceleration ($A_y$) data generated by badge 12, in one example, is processed by badge 12 to determine the speed of the asset associated with badge 12 and to determine if the asset associated with badge 12 has fallen or been dropped. In another example, the vertical acceleration ($A_y$) data is forwarded to master station 34 which processes the vertical acceleration ($A_y$) to determine the speed of the asset associated with badge 12 and to determine if the asset associated with badge 12 has fallen or been dropped.

In an exemplary embodiment, the master station 34 receives the displacement samples from the badges 12 and further processes the displacement samples to obtain an estimated distance traveled and an estimated heading traveled. In particular, the master station 34 determines the estimated distance traveled based upon the motion data received from the badges 12 in a manner similar to one of the methods described in "Using the ADXL202 in Pedometer and Personal Navigation Applications," by Harvey Weinberg. The master station 34 also determines an estimated heading traveled from the motion data and/or the heading data received from the badges 12. In particular, the master station 34 performs one or more of the following functions on the motion data and/or the heading data: offset-elimination, temperature drift compensation, non-orthogonality correction of sensor axes, interference field correction, declination compensation, tilt compensation, and true north compensation in a manner similar to those described in "Electronic Compass Design Using KMZ51 and KMZ52." Alternatively, the controller 52 of the badges 12 may be implemented with a more powerful processor which executes software or firmware instructions to implement all or portions of the functions performed on motion data and/or heading data described above.

Figure 4:
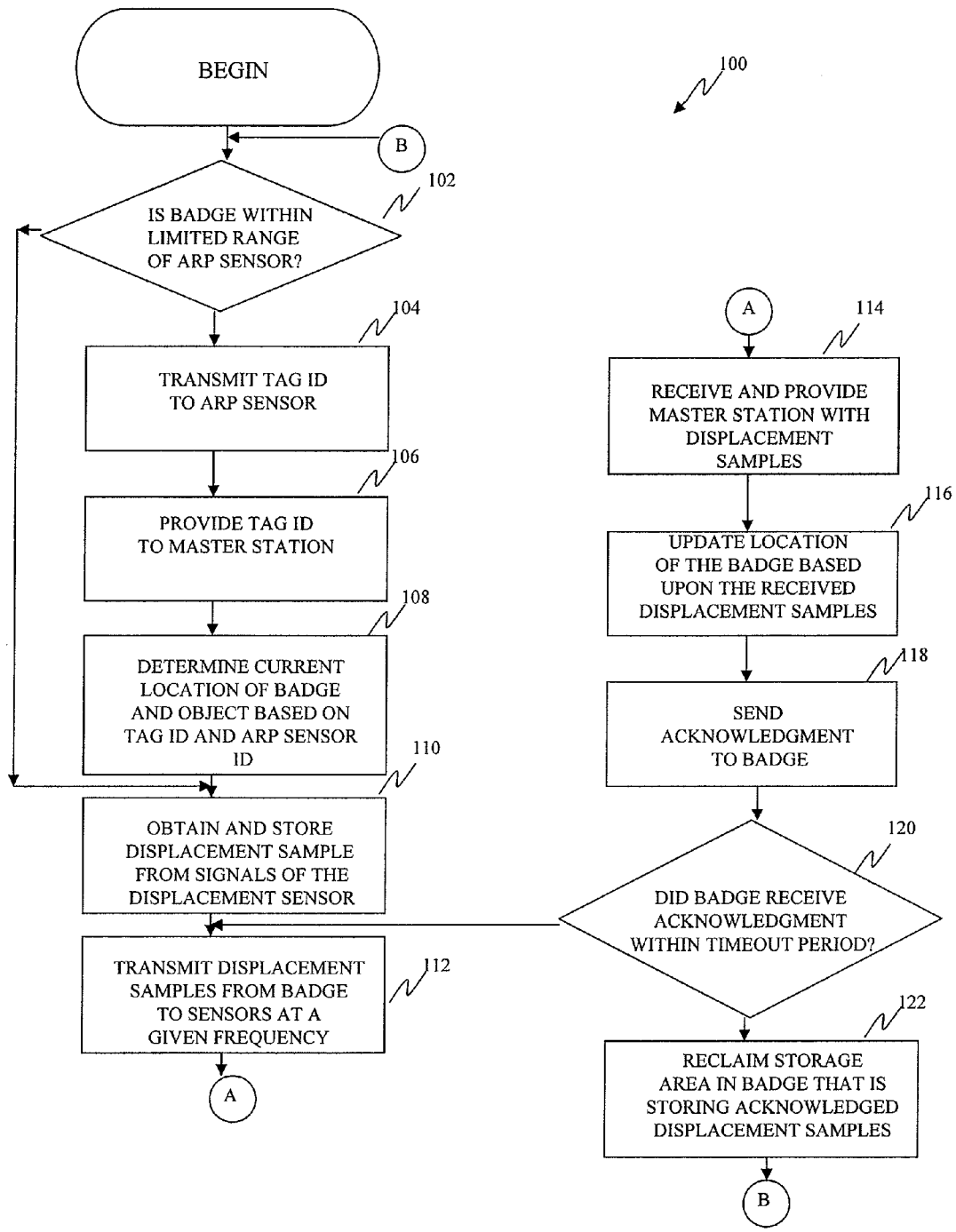
FIG. 4 illustrates an exemplary location method used by the activity based tracking system of FIG. 1 to determine the location of tagged objects based upon information received from the badges of the tagged objects.

Shown in FIG. 4 is a location tracking method 100 used to track the location of objects tagged with badges 12. In step 102, the badge 12 determines whether the badge 12 is within the limited range of an ARP sensor 20. If the badge 12 is within range of the ARP sensor 20, then the badge 12 in step 104 transmits a tag ID to the ARP sensor 20 that uniquely identifies the badge 12. More specifically, the badge 12 includes a passive RF transmitter that is powered by the ARP sensors 20 when in range of the ARP sensors 20. Accordingly, the badge 12 determines that the badge 12 is within range of the ARP sensor 20 if the transmitter 54 of the badge 12 is powered by the ARP sensor 20. In step 104, the ARP sensor 20 that receives the information from the badge 12 provides the master station 34 with the tag ID received from the badge 12 and a sensor ID that identifies the ARP sensor 20.

In a power saving embodiment of the badge 12, the ARP sensor 20 in step 104 further causes the badge 12 to power active portions of the badge 12 (e.g., displacement sensor 50, controller 52 ) with an on-board battery (not shown). In particular, after receiving power from the ARP sensor 20 and initiating battery operation of the active portions, the badge 12 continues to power the active portions until the controller 52 detects a power off condition. For example, the controller 52 may remove battery power from the active portions of the badge 12 after determining that the badge 12 has not received transmissions from the sensors 20, 22 for a predetermined time period (e.g., 10 minutes), and/or that the badge 12 has been static (i.e., substantially still) for a predetermined time period (e.g., 5 minutes).

In step 106, the master station 34 determines the location of the badge 12 and associated tagged object from the tag ID and the sensor ID. More specifically, the master station 34 includes facility map information that defines the location of doorways, walls, ARP sensors 20, and other static features of the facility. From the facility map information and the information received from the ARP sensor 20 in step 104, the master station 34 determines that the current location of the tagged object is the ARP sensor 20 identified by the received sensor ID.

The badge 12 in step 108 starts transmitting displacement samples at a predetermined interval (e.g., every 5 seconds). In an exemplary embodiment, the badge 12 transmits signals representative of the tag ID and all displacement samples that have been stored in the memory 58 since receiving an acknowledgment of a prior displacement sample transmission. In an exemplary embodiment, the controller 52 obtains displacement samples from the displacement signals of the displacement sensor 50 on a predetermined interval (e.g., 1 millisecond intervals) and stores the obtained displacement samples in the memory 58. In particular, the controller 52 periodically samples the received displacement signals during the given interval to obtain displacement samples that are generally representative of the displacement signals during the interval. After obtaining the displacement samples for the interval, the controller 52 stores the displacement samples in the memory 58. In an alternative embodiment, the badge 12 transmits the displacement samples at various different intervals depending upon the rate of movement of the badge 12 as described in U.S. Provisional Patent Application 60/306,818, filed Jul. 20, 2001, converted to U.S. patent application Ser. No. 10/199,849, now U.S. Pat. No. 6,972,683 and entitled "Locating Badge with Intelligent Transmission Based on Acceleration," the disclosure of which is hereby incorporated by reference.

In an alternative embodiment, the controller 52 combines displacement samples to reduce the number of displacement samples stored in the memory 58. In particular, the controller 52 combines displacement samples that are temporally adjacent to one another and that do not significantly differ from one another. For example, if the controller 52 determines that the motion and heading of temporally adjacent displacement samples are within a predetermined tolerance, then the controller 52 combines the two displacement samples (e.g., averaging the samples, discarding one of the samples) to obtain a displacement sample representative of the interval associated with both displacement samples. In this manner, the controller 52 obtains a single displacement sample that is representative of several temporally adjacent displacement samples thus reducing the number of samples stored in the memory 58.

Further, the controller 52 of the alternative embodiment includes timing information with the displacement samples. For example, the controller 52 includes a count value with the motion data and heading data of the displacement samples to indicate the number of samples of which the stored displacement sample is representative. Alternatively, the controller 52 includes a timestamp value with the displacement samples. The controller 52 may instead utilize other techniques for correlating the motion data and heading data of a displacement sample to a respective time interval such as including an interval sequence count with the displacement samples.

As a result of periodically transmitting the displacement samples and tag ID in step 112, receivers of the sensors 22 in step 114 receive signals that are representative of the displacement samples and tag ID of the badge 12. The sensors 22 further provide the master station 34 with information representative of the tag ID and displacement samples in step 114.

The master station 34 in step 116 determines the movement path and location of the badge 12 based upon the received tag ID, displacement samples, and the previously determined location for the badge 12 (e.g., location of an ARP sensor 20, or location determined from displacement samples). The master station 34 processes the motion data, heading data, and optionally the timing data of the displacement samples to determine the movement path of the badge 12. Techniques for obtaining distance information from motion data are described in the previously referenced Analog Devices publications.

The master station 34 in step 116 further adjusts the movement path and location to prevent a conflict between the calculated movement path for the badges 12 and the layout information for the facility. For example, the calculated movement path may indicate that the tagged object passed through a wall at a location near a doorway and then proceeded down a hallway outside the doorway. The master station 34 may alter the calculated movement path to indicate the reality that the tagged object passed through the doorway. Methods such as fuzzy logic, neural networks, expert systems, and/or other artificial intelligence techniques for correlating location information with map information are known.

In response to receiving the tag ID and displacement samples from the badges 12, the master station 34 in step 118 causes an acknowledgment to be sent to the badge 12 via a transmitter such as the RF and/or IR transmitters of the ARP sensors 20 or the long range sensors 22. If the badge 12 receives the acknowledgment, then the controller 52 in step 120 reclaims the storage area of the memory 58 used to store the acknowledged displacement samples. However, if the controller 52 determines in step 120 that the badge 12 did not receive the acknowledgment message within a predefined timeout period (e.g., 1 second), then the controller 52 returns to step 112 in order to retransmit the tag ID and displacement samples.

In one embodiment, badge 12 is configured to transmit the displacement samples and tag ID at two or more transmission rates to reduce errors in the calculated location of badge 12 due to rapid changes in direction. It is possible that errors in location of badge 12 can arise due to the changes in direction of badge 12 between two transmissions of badge 12. For example, assume that the transmission rate of badge 12 is once per second and at a first time (t=1 second), the last known location of badge 12 is ten feet north of ARP sensor 20 and badge 12 transmits a signal including displacement information indicating that badge 12 is moving north of ARP sensor 20 at a speed of 2 feet per second. Immediately after transmitting the displacement information at the first time, badge 12 changed direction and began heading back towards ARP sensor 20 at two feet per second. At a second time (t=2 seconds), badge 12 sends a second transmission including displacement information indicating that badge 12 is moving south toward ARP sensor 20 at a speed of 2 feet per second.

As such the true location of badge 12 at the second time is generally eight feet north of ARP sensor 20. However, master station 34 assumes that badge 12 is moving north at two feet per second between the first time an the second time. As such, master station 34 will incorrectly calculate the location of badge 12 to be twelve feet north of ARP sensor 20 and heading south toward ARP sensor 20 at two feet per second. In order to reduce or generally eliminate this discrepancy in the location of badge 12, badge 12 is configured increase its associated transmission rate in response to rapid changes in direction of badge 12. In one example, whenever there is a rapid change in direction of badge 12, badge 12 immediately generates a transmission including the new displacement information. In another example, whenever there is a rapid change in direction, badge 12 increases the transmission rate of badge 12 for a preset time period. For example, badge 12 in the above example may begin transmitting at a rate of four times a second for the next three seconds.

Figure 5:
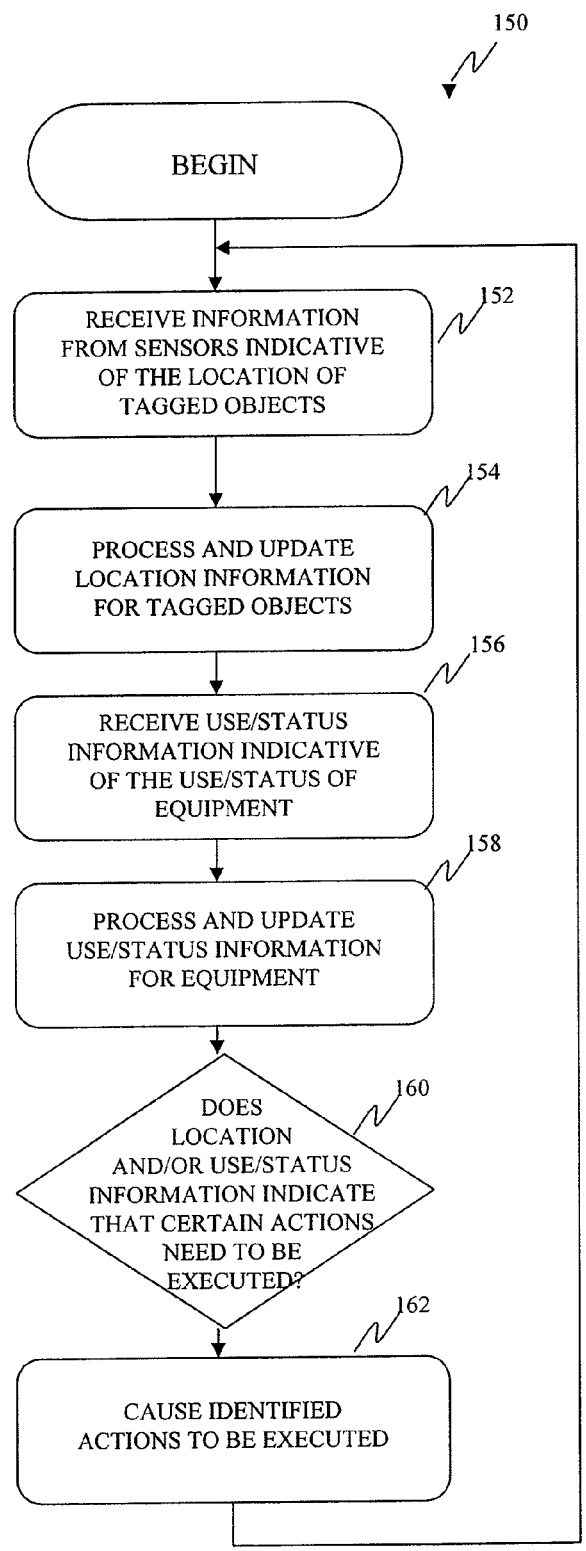
FIG. 5 illustrates an exemplary activity based tracking method used by the activity based tracking system of FIG. 1 to perform activity based tracking.

Referring now to FIG. 5, there is depicted an activity based tracking method 150 implemented by the ABT system 10. The master station 34 of the ABT system 10 in step 152 receives information from the ARP sensors 20 that is indicative of the location of tagged objects associated with the badges 12. The master station 34 in step 154 processes the information received in step 152 and updates location information for the tagged objects associated with the badges 12 accordingly.

The master station 34 also receives in step 156 information from the equipment sensors 24 that is indicative of the use/status of the equipment associated with the equipment sensors 24. In step 158, the master station 34 processes the information received in step 156 and updates use/status information for the equipment associated with the equipment sensors 24.

The master station 34 in step 160 analyzes the updated location and use/status information to determine whether actions need to be taken in response to the received information. In particular, the master station 34 determines for each predefined rule whether all conditions associated with the rule have been satisfied. If the updated location and/or use/status information satisfies the conditions of a given rule, then the master station 34 in step 162 causes actions associated with each satisfied rule to be executed. However, if the master station 34 determines that no predefined rule has been satisfied, then the master station 34 returns to step 62 in order to process additional information from the ARP sensors 20 and the equipment sensors 24.

Hygiene monitoring systems that monitor handwashing and equipment washing are disclosed in copending U.S. patent application Ser. No. 09/699,796, filed Oct. 30, 2000 and are exemplary embodiments of the activity based tracking method 100. In particular, the hygiene monitoring systems receive information indicative of the location of caregivers and handwashing devices and use/status information indicative of the use of the handwashing devices. From this information, the hygiene monitoring systems determine whether caregivers need to wash their hands to maintain compliance with an established hygiene policy. The disclosure of U.S. patent application Ser. No. 09/699,796, filed Oct. 30, 2000 and entitled "Hygiene Monitoring System" is hereby incorporated by reference.

Figure 6:
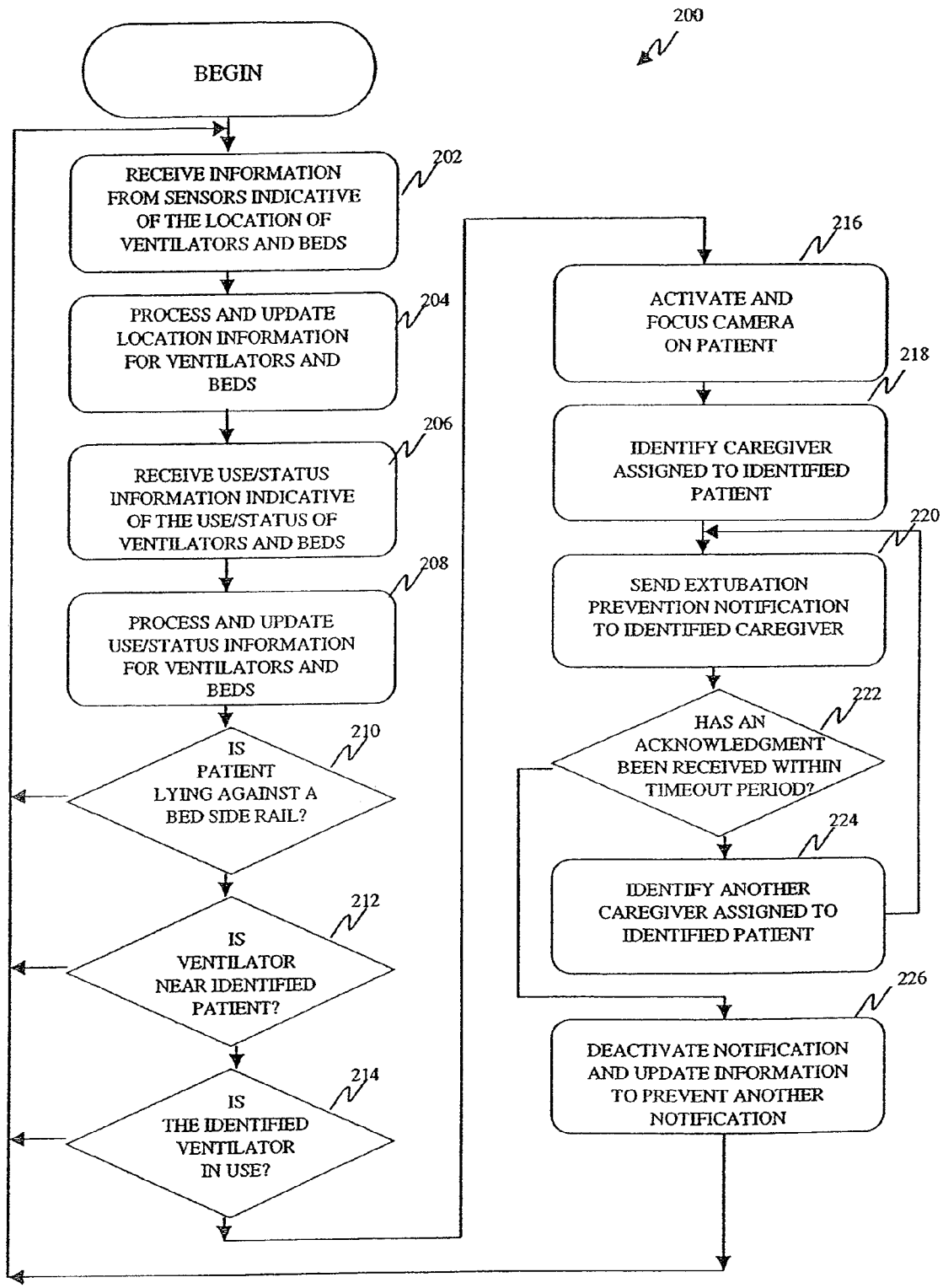
FIG. 6 illustrates an exemplary extubation prevention method which is a particular embodiment of the activity based tracking method shown in FIG. 5.

Referring now to FIG. 6, there is depicted an exemplary extubation prevention method 200 which is a particular embodiment of the ABT method 150. Experience has shown that extubation is more likely if a patient is lying against a side rail 26 of a bed 16 while on a ventilator 18. Extubation may result in harm to the patient and lost work time to re-establish the breathing pathway. When executing the extubation prevention method 200 of FIG. 6, the ABT system 10 generally determines whether a patient is using a ventilator 18 while lying against a side rail 26 of a bed 16. If the patient is using a ventilator 18 while lying against a bed side rail 26, then the ABT system 10 alerts a caregiver via a pocket pager, badge 12, or other portable device and may provide the caregiver with streaming video of the patient via the portable device or a nearby video display 28. With such information, the caregiver determines whether corrective action is needed in order to prevent a possible extubation.

The master station 34 in step 202 receives location information from badges 12 of tagged beds 16 and badges 12 of tagged ventilators 18 that is indicative of the location of the tagged beds 16 and tagged ventilators 18. The master station 34 in step 204 processes the location information received in step 202 and updates location information for the tagged beds 16 and ventilators 18.

The master station 34 of the ABT system 10 in step 206 receives use/status information from equipment sensors 24 of beds 16 and ventilators 18 that is indicative of the use and/or status of the beds 16 and ventilators 18. More specifically, the ABT system 10 in step 206 receives use/status information from equipment sensors 24 of beds 16 that is indicative of positions of patients within beds 16. In an exemplary embodiment, the beds 16 are equipped with one or more equipment sensors 24 in the bed side rails 26 that detect the weight of the patient lying against the bed side rail 26. In an alternative embodiment, the beds 16 include a patient support surface having one more equipment sensors 24 that detect the position of the patient upon the patient support surface as disclosed in U.S. Pat. No. 6,208,250, entitled "Patient Position Detection Apparatus for a Bed 16," the disclosure of which is hereby incorporated by reference.

The master station 34 in step 206 also receives use/status information from equipment sensors 24 of ventilators 18 that is indicative of the usage of the ventilators 18. In an exemplary embodiment, the ventilators 18 include one or more equipment sensors 24 that detect whether the ventilator 18 is in use. For example, the ventilators 18 include a current sensor, voltage sensor, and/or power sensor which respectively detect the presence or absence of an operating current, operating voltage, and/or operating power and provide the result of such detection to the master station 34. Numerous other manners for detecting whether a device such as a ventilator 18 is operating are well known in the art and any may be used with the present invention.

The master station 34 in step 208 processes the use/status information received in step 206 and updates use/status information for the beds 16 and the ventilators 18 accordingly. More specifically, the master station in step 208 updates use/status information to indicate the current position of patients in beds 16 and which ventilators 18 of the ABT system 10 are presently being used.

The master station 34 analyzes the updated location and use/status information to determine whether a patient has an increased likelihood of extubation. More specifically, the master station 34 in step 210 determines whether a patient is lying against a bed side rail 26 based upon the use/status information associated with the beds 16. If the master station 34 determines that a patient is not lying against a bed side rail 26, then the master station 34 returns to step 202 in order to process further information received from the badges 12 and the equipment sensors 24.

If the master station 34 determines that the patient is lying against a bed side rail 26, then the master station 34 further determines whether the patient is using a ventilator 18. In particular, the master station 34 determines whether a ventilator 18 is near the patient lying against the bed side rail 26 based upon location information associated with the ventilators 18. In an exemplary embodiment, the master station 34 determines that the ventilator 18 is near the patient if the location information associated with the ventilator 18 indicates that the ventilator 18 is in the same room as the patient lying against the bed side rail 26. Alternatively, the master station 34 may determine that the ventilator 18 is near the patient if the location information indicates that the ventilator 18 is within a predetermined range (e.g., 3 feet) of the patient or the bed 16 on which the patient is lying.

If the master station 34 determines that a ventilator 18 is not near the patient lying against the bed side rail 26, then the master station 34 returns to step 202 in order to process further information received from the badges 12 and the equipment sensors 24. However, if the master station 34 determines that a ventilator 18 is near the patient lying against the bed side rail 26, then the master station 34 in step 214 determines whether the ventilator 18 near the identified patient is in use based upon the use/status information associated with the ventilator 18.

If the master station 34 determines that the ventilator 18 is not in use, then the master station 34 returns to step 202 in order to process further information received from the badges 12 and the equipment sensors 24. However, if the master station 34 determines that the ventilator 18 is in use, then the master station 34 causes actions associated with preventing extubation of the identified intubated patient lying against the bed side rail 26. In an exemplary embodiment, the master station 34 in step 216 activates a camera 32 located in the room of the identified patient and focuses the camera 32 on the patient if not already focused on the patient. The master station 34 in step 218 identifies which caregiver is assigned to the identified patient based upon patient assignment data that the master station 34 either maintains or has access to.

The master station 34 in step 220 sends an extubation prevention notification to the caregiver assigned to the intubated patient lying against the bed side rail 26. More specifically, the master station 34 causes the badge 12 of the identified caregiver to provide a tactile indication (e.g., vibrate), an audible indication (e.g., beep), a visual indication (e.g., blinking LED), and/or some other indication of the possible extubation situation. Furthermore, the master station 34 provides the identified caregiver with streaming video of the patient via a hospital network system such as the system disclosed in U.S. Pat. Nos. 5,561,412, 5,699,038, and 5,838,223, the disclosures of which are hereby incorporated by reference. The streaming video enables the caregiver to assess the patient specific situation to determine without physically entering the room of the patient if intervention is required. If the streaming video indicates that intervention is not required, then the caregiver is saved a trip to the patient's room thus providing a savings of time. In an exemplary embodiment, the master station 34 causes the video stream be sent to a video display 28 located near the caregiver (such as a nurse's station, hall monitor, etc.) or to a portable pager or badge 12 carried by the caregiver which has video playback capabilities.

The master station 34 in step 222 determines whether an acknowledgment was received from the caregiver within a predetermined time span (e.g., 30 seconds). The ABT system 10 provides various manners for the caregiver to acknowledge the extubation prevention notification. For example, the ABT system 10 enables caregivers to provide acknowledgments by actuating a mechanism (e.g., switch, button) on their badges 12, or actuating a nearby acknowledgment mechanism (e.g., switch, button) located in various locations throughout the facility such as in the patient rooms, hallways, nurses station, rest rooms, utility rooms, etc. Alternatively, the ABT system 10 enables the caregiver to provide the acknowledgment via a remote control carried by the caregiver such as the remote control disclosed in U.S. patent application Ser. No. 09/848,941, entitled "Remote Control for Hospital Bed," filed May 4, 2001, the disclosure of which is hereby incorporated by reference.

If the master station 34 determines that an acknowledgment was not received from the caregiver within the predetermined timeout period, then the master station 34 in step 224 identifies another caregiver assigned to the patient. The master station 34 then returns to step 220 in order to send an extubation prevention notification and accompanying video stream to the newly identified caregiver. However, if the maser station 34 determines that an acknowledgment was received from the caregiver within the predetermined timeout period, then the master station 34 in step 226 deactivates the extubation prevention notification and updates use/status information associated with the patient and/or the ventilator 18 such that another extubation prevention notification is not generated for the same patient for a predetermined time span (e.g., 5 minutes). The master station 34 then returns to step 202 in order to process further information received from the badges 12 and the equipment sensors 24.

Figure 7:
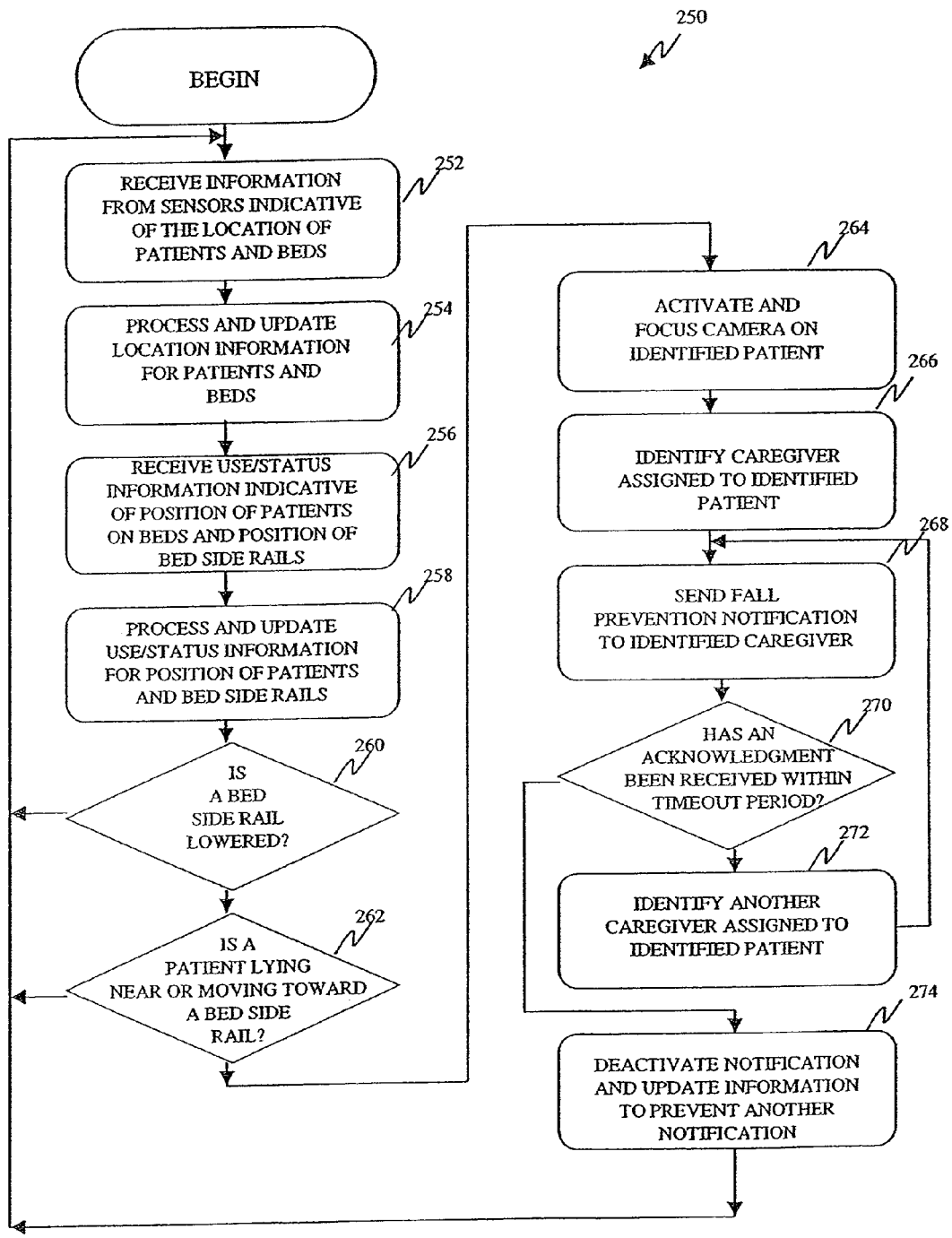
FIG. 7 illustrates an exemplary fall prevention method which is a particular embodiment of the activity based tracking method shown in FIG. 5.

Referring now to FIG. 7, there is depicted an exemplary fall prevention method 250 which is another exemplary embodiment of the ABT method 100. Experience has shown that a patient is more likely to fall out of a bed 16 if a side rail 26 of a bed 16 is in a lowered position (i.e., down). When executing the patient fall prevention method 250 of FIG. 7, the ABT system 10 generally detects the position of a patient in a bed 16 and the position of the side rails 26 of the bed 16. If ABT system 10 detects that a bed side rail 26 is in a lowered position and the patient is lying near or is moving toward the lowered bed side rail 26, then the ABT system 10 provides a caregiver with a fall prevention notification via a pocket pager or badge 12 and provides the caregiver with streaming video of the patient via a pocket pager, badge 12, or other portable device, or a nearby video display 28. With such information, the caregiver can assess whether corrective action is needed in order to prevent a possible fall.

The master station 34 in step 252 receives location information from badges 12 of tagged patients and badges 12 of tagged beds 16 that is indicative of the location of the tagged patients and beds 16. The master station 34 in step 254 processes the location information received in step 252 and updates location information for the tagged patients and beds 16 accordingly.

The master station 34 in step 254 receives use/status information from equipment sensors 24 of the beds 16 that is indicative of the position of a patient within a bed 16 and the position of bed side rails 26. As indicated above, the beds 16 include a patient support surface having one or more equipment sensors 24 that detect the position of a patient upon the patient support surface as disclosed in U.S. Pat. No. 6,208, 250. Moreover, the bed side rails 26 include one or more equipment sensors 24 that detect the position of the side rail 26 and provide information indicative of the detected position of the bed side rail 26. In an exemplary embodiment, the bed side rails 26 are implemented as indicated in U.S. Pat. No. 6,021,533, filed on Aug. 25, 1992 and entitled "Mattress Having a Siderail Down Sensor," the disclosure of which is hereby incorporated by reference.

The master station 34 in step 258 processes the use/status information received in step 256 and updates use/status information for the beds 16 and the bed side rails 26 accordingly. More specifically, the master station in step 258 updates use/status information that indicates the position of patients on beds 16 and the position of bed side rails 26.

The master station 34 analyzes the updated location and use/status information to determine whether a patient has an increased likelihood of falling from a bed 16. More specifically, the master station 34 in step 260 determines whether a bed side rail 26 is lowered based upon the use/status information received from the bed side rails 26 in step 256. If the master station 34 determines that a bed side rail 26 is not in the lowered position (i.e., determines that the bed side rail 26 is in the raised position), then the master station 34 returns to step 252 in order to receive and process further location and use/status information. However, if the master station 34 determines that a bed side rail 26 is in the lowered position, then the master station 34 proceeds to step 262 in order to determine whether a patient is lying near or is moving toward a lowered bed side rail 26.

In step 262, the master station 34 analyzes the use/status information indicative of the position of patients within beds 16 in order to determine whether a patient is lying near or is moving toward the identified lowered bed side rails 26. If the master station 34 determines that a patient is not lying near and is not moving toward a lowered bed side rail 26, then the master station 34 returns to step 252 in order to process further location and/or use/status information.

However, if the master station 34 determines that the patient is lying near or is moving toward a lowered bed side rail 26, then the master station 34 causes actions associated with preventing the identified patient from falling from bed 16. In an exemplary embodiment, the master station 34 in step 264 activates a camera 32 located in the room of the identified patient and focuses the camera 32 on the patient if not already focused on the patient. The master station 34 in step 266 identifies which caregiver is assigned to the identified patient based upon patient assignment data that the master station 34 either maintains or has access to.

The master station in step 268 sends a fall prevention notification to the caregiver assigned to the patient lying near or moving toward the lowered bed side rail 26. More specifically, the master station 34 causes the badge 12 of the identified caregiver to provide a tactile indication (e.g., vibrate), an audible indication (e.g., beep), a visual indication (e.g., blinking LED), and/or some other indication of the possible fall situation. Furthermore, the master station 34 provides the identified caregiver with streaming video of the patient via a hospital network system such as the system disclosed in U.S. Pat. Nos. 5,561,412, 5,699,038, and 5,838,223. In an exemplary embodiment, the master station 34 causes the video stream be sent to a video display 28 located near the caregiver (such as a nurse's station, hall monitor, etc.) or to a portable pager or badge 12 carried by the caregiver which has video playback capabilities.

The master station 34 in step 270 determines whether an acknowledgment was received from the caregiver within a predetermined timeout period (e.g., 30 seconds). The ABT system 10 provides various manners for the caregiver to acknowledge the fall prevention notification. For example, the ABT system 10 enables caregivers to provide acknowledgments by actuating a mechanism (e.g., switch, button) on their badges 12 or actuating a nearby acknowledgment mechanism (e.g., switch, button) located in various locations throughout the facility such as in the patient rooms, hallways, nurses station, rest rooms, utility rooms, etc.

If the master station 34 determines that an acknowledgment was not received from the caregiver within the predetermined timeout period, then the master station 34 in step 272 identifies another caregiver assigned to the patient. The master station 34 then returns to step 268 in order to send a fall prevention notification and accompanying video stream to the newly identified caregiver. However, if the maser station 34 determines that an acknowledgment was received from the caregiver within the predetermined timeout period, then the master station 34 in step 274 deactivates the fall prevention notification and updates use/status information associated with the patient, the bed 16, and/or bed side rails 26 such that another fall prevention notification is not generated for the same patient for a predetermined time span (e.g., 5 minutes). The master station 34 then returns to step 252 in order to process further location and/or use/status information.

Figure 8:
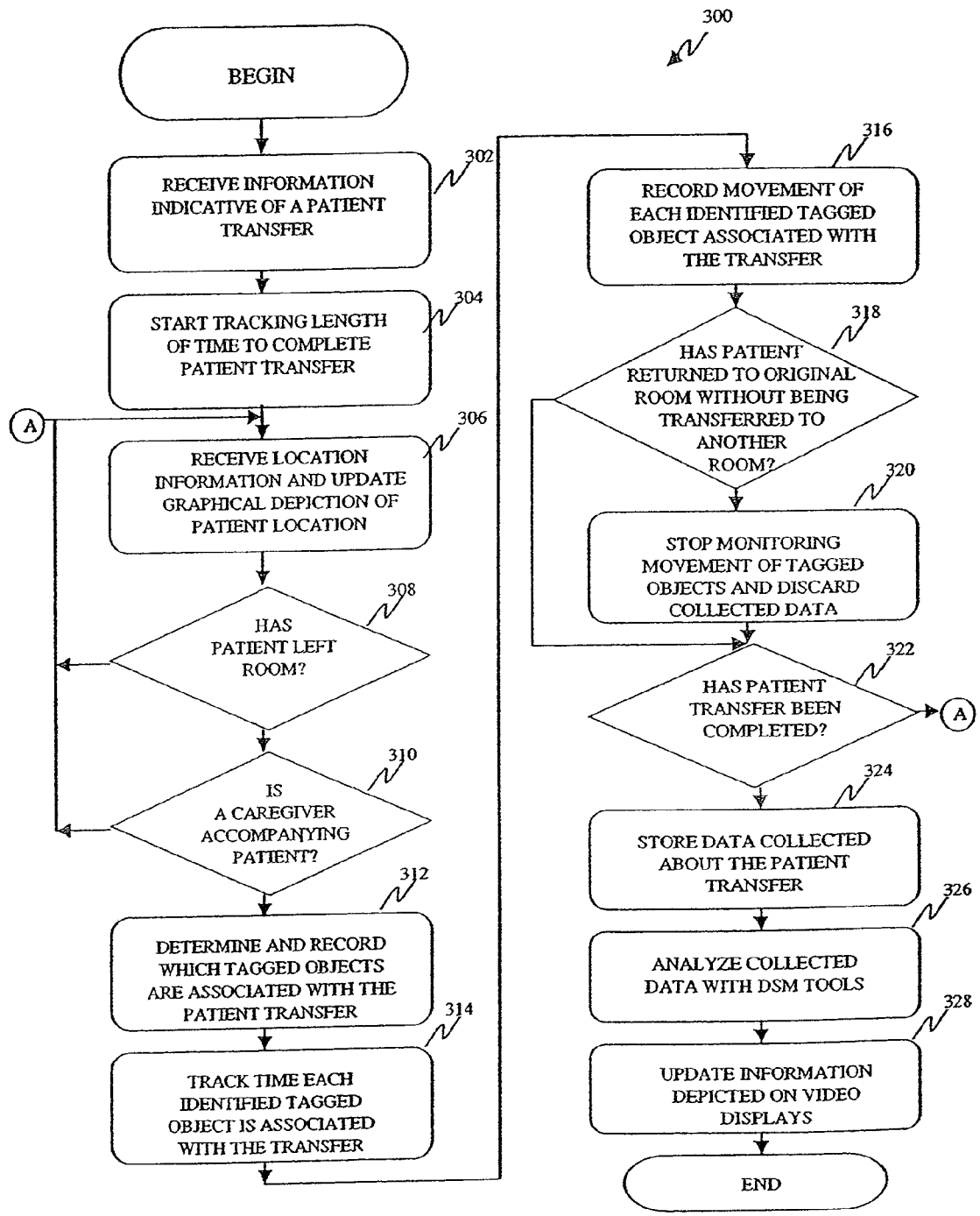
FIG. 8 illustrates an exemplary modeling simulation method which is a particular embodiment of the activity based tracking method shown in FIG. 5.

Referring now to FIG. 8, there is provided an automated method 300 for gathering information about an activity or processes in a healthcare facility and analyzing the gathered information with a simulation modeling ("SM") tool such as a dynamic simulation modeling tool or a static simulation modeling tool. SM tools enable simulations of the relationships among various processes competing for space, time and resources and enable a quantitative assessment of the impact of proposed changes. However, such SM tools require an extensive amount of data associated with the activities and processes to be simulated and analyzed. Due to the costs associated with traditional methods for obtaining sufficient information regarding activities and processes, SM tools have not been utilized in the healthcare industry. The ABT system 10 greatly reduces the cost of information gathering thus making it feasible to apply SM tools and technology to the healthcare industry.

The automated method 300 of FIG. 8 is illustrated and described in regards to gathering and analyzing information regarding the process of transferring a patient from one location to another location. However, those skilled in the art should readily appreciated that similar techniques apply to gathering and analyzing information about other processes.

In step 302, the ABT system 10 receives information indicative of the start of the process to be recorded. For example, in the case of tracking a patient transfer, the ABT system 10 receives information describing a patient transfer order that has been entered into the ABT system 10 or a clinical information system in communication with the ABT system 10 in response to a written transfer order of a physician. In an alternative embodiment, the physician directly enters the patient transfer order into the ABT system 10 or the clinical information system in communication with the ABT system 10 via a point of care computer system.

The ABT system 10 begins to record information related to the monitored activity or process. In particular, the ABT system 10 in step 304 starts tracking the length of time to complete the patient transfer. For example, the ABT system 10 records the time at which the patient transfer order was received, records the time at which the patient transfer order was written by the physician, begins a timer in response to receiving the patient transfer order, and/or utilizes some other mechanism to track the length of time to complete the patient transfer.

The ABT system 10 also tracks and records the location and movement path of tagged objects associated with the monitored activity. In particular, the ABT system 10 in step 306 monitors the location of the patient to be transferred based upon location information received from the badge 12 of the patient. Further, the ABT system 10 in step 306 continuously updates a graphical depiction of the current location of the patient upon one or more video displays 28. The ABT system 10 causes one or more video displays 28 to provide further visual indications that a transfer is taking place such as (i) causing textual information indicative of the transfer to be displayed on video displays 28 (e.g., text in the scoreboard areas), and/or (ii) causing the graphical depiction of the patient and/or the room in which the patient is to be transferred from to be altered (e.g., blink, change color).

In step 308, the ABT system 10 determines whether the patient has left the room based upon location information received from the badge 12 of the patient. If the ABT system 10 determines that the patient has not left the room, then the ABT system 10 returns to step 306 in order to further update the location of the patient. However, if the ABT system 10 determines that the patient has left the room, then the ABT system 10 in step 310 determines whether a caregiver is accompanying the patient based upon location information received by the badges 12 of the caregivers. If the ABT system 10 determines that a caregiver is not accompanying the patient, then the ABT system 10 returns to step 306 in order to further update the location of the patient.

The ABT system 10 in step 312 records which tagged objects (i.e., equipment, caregivers, etc.) are associated with the transfer of the patient. In particular, the ABT system 10 (i) determines based upon the location information received from badges 12 which caregivers are taking part in the transfer of the patient and which equipment is being transferred with the patient, and (ii) records identification information associated with such tagged objects. In an exemplary embodiment, the ABT system 10 determines which equipment is being transferred with the patient based upon information received from badges 12 of the equipment and business logic of the master station 34. Alternatively, equipment may be manually associated with a patient via a terminal (not shown) of the ABT system 10, thus providing the ABT system 10 with an indication of which equipment needs to be tracked when the patient is transferred.

The ABT system 10 in step 314 tracks the length of time the identified tagged objects are involvement with the patient transfer. In particular, the ABT system 10 records the time at which each identified tagged object becomes involved with the patient transfer and records the time at which each identified tagged object becomes no longer involved with the patient transfer. Alternatively, the ABT system uses individual timers for each of the identified tagged objects or some other mechanism in order to track the objects involvement. In general, the ABT system 10 tracks the elapsed time of the patient from source (i.e., original room) to destination (i.e., new room), tracks the time of involvement of each person 14 involved with the transfer, and tracks the time of involvement for each piece of equipment involved with the transfer.

The ABT system 10 in step 316 records the movement of the patient, caregivers, and equipment associated with the patient transfer. The exemplary ABT system 10 periodically receives location information from the badges 12 of each tagged object on relatively short time intervals such as every 5 seconds. However, in order to reduce the amount of location information recorded, the ABT system 10 of the exemplary embodiment stores the location of each patient, caregiver, and equipment associated with the transfer on a longer time interval such as every 10 seconds. In an exemplary embodiment, the longer time interval used by ABT system 10 is user definable for each monitored activity in order to enable user selectable granularity of the movement path of the patient, caregivers, and equipment associated with a particular activity.

The ABT system 10 in step 318 determines based upon location information for the patient whether the patient has returned to the original room without being transferred to another room. If the ABT system 10 determines that the patient has been returned to the original room, then the ABT system 10 in step 320 stops monitoring the movement path and elapsed times of the identified tagged objects and returns to step 306 without saving the acquired information. However, if the ABT system 10 determines that the patient has been transferred to another room, then the ABT system 10 in step 324 stores the acquired information (i.e., elapsed times, movement, etc.) in a database.

The ABT system 10 then in step 326 utilizes SM tools to perform calculations on the information stored in the database. For example, the SM tools analyze the information to identify bottlenecks, resources consumed, critical paths, etc., related to transfers based upon information gathered over a predetermined time period. The ABT system 10 in step 328 updates information on the video displays 28 in order to indicate results of the SM tool analysis. For example, the ABT system 10 causes the video displays 28 to provide statistical information related to the monitored activity such as the number of transfers, the total cost of transfers, and personnel hours consumed due to transfers. Moreover, the ABT system 10 further causes the graphical depiction of rooms associated with awaiting transfers to blink, and causes the graphical depiction of hallways associated with bottlenecks in the physical transfer to blink red.

Referring now to FIG. 9, there is shown an exemplary graphical display 350 generated by the activity based tracking system 10 on video displays 28. In the exemplary embodiment, the exemplary graphical display 350 is implemented as a MedModel application executing on the master station 34. MedModel is a software tool of ProModel Corporation which is generally used for simulation modeling of healthcare facilities. The graphical display 350 includes a floor layout 352 and a scoreboard status 354. The floor layout 352 depicts the physical features of the facility (i.e., location of walls, rooms, doorways, etc.) and the location of tagged objects (e.g., beds 16, ventilators 18, persons 14). As indicated above, the master station 34 causes the floor layout 352 to provide visual indications of monitored activities (e.g., causes rooms, persons 14, and/or equipment associated with a monitored activity to be highlighted, to be depicted in a different color, or to blink on and off.)

The scoreboard status 354 generally provides pseudo-real time statistics and other information for the facility and activities monitored in the facility. For example, the master station 34 as a result of monitoring patient transfers displays the total number of patient transfers, the total cost of patient transfers, personnel hours consumed due to patient transfers, and/or other statistical information associated with patient transfers over a certain time period.

In one embodiment, the locating system of ABT 10 compares the location of an asset to expected locations of the asset and provides an indication to a caregiver or initiates an alarm if the location of the asset is an unexpected location. For example, if the asset is a patient, the locating system or ABT 10 expects that badge 12 corresponding to the patient will most likely always be at least about three feet above the floor in patient room A shown in FIG. 1. As such, if the location of the patient (i.e., badge 12) is determined to be less than about three feet from the floor, the locating system or ABT 10 initiates an alarm or provides an indication to a caregiver that the patient has fallen or is lying on the floor. By knowing that the previous location of the patient was in bed 16, the locating system or ABT 10 may determine that the patient has fallen out of bed.

In one variation, the locating system ABT 10 waits a predetermined time period to determine if the location of the asset returns to an expected location before initiating an alarm or providing an indication to a caregiver. The length of the predetermined time period is selected to minimize false alarms triggered by a patient retrieving an article from the floor or engaging in other everyday activities. In another variation, the status of siderail 26 further assists in determining if a patient has exited bed 16 or fallen. In yet another variation, the acceleration data from badge 12 is used to distinguish between normal movement and a fall (sudden change in acceleration, see FIG. 3B).

In one example, the type of asset governs the expected locations of the asset. For instance, it is known by the locating system ABT 10 that badge 12 when corresponding to an I/V pole (not shown) is always placed approximately three feet from the base of the I/V pole. As such, any altitude deviation beyond a preset altitude deviation from the determination that the badge corresponding to the I/V pole is approximately three feet from the floor results in the initiation of an alarm or an indication to a caregiver. Further, an altitude deviation from the preselected altitude deviation may indicate that the asset (I/V pole, ventilator, computer, etc.) has been dropped and must therefore be recertified. In one variation, the displacement sensor 50 of badge 12 provides acceleration data which assists the locating system or ABT 10 to distinguish between a situation wherein the asset has been placed on the floor and a situation wherein the asset has been dropped.

In one example, the locating system or ABT 10 uses both status information of equipment or personnel along with location information to better determine whether the location of the asset corresponds to an expected location. For example, a bed such as bed 16 provides a status signal indicating that the patient is lying on bed 16. As such, a location determination which indicates that the patient is less than about three feet from the floor might correspond to a patient lying in bed 16 when bed 16 is positioned in a low configuration, not that the patient has fallen.

In one embodiment, the locating system or ABT 10 determines, based on location information, the status of an asset. For example, based on location information, the locating system or ABT 10 may determine that a window or a door is opened or closed.

In one embodiment, the locating system or ABT 10 prevents the movement of an asset based on the current location of at least one other asset. For example, based on the location of a monitor (not shown) relative to bed 16, the locating system or ABT 10 may prevent bed 16 from moving to a raised position or to a lowered position based on expected interference with the monitor. Once the monitor has been moved farther away from bed 16, the locating system or ABT 10 will allow the movement of bed 16 to a raised position or to a lowered position.

In one embodiment, ABT 10 is further configured to record location information related to therapy. For example, a badge 12 may be attached to a cast or sling for a patient lying in bed 16 or placed in traction. ABT 10 records the location of the cast or sling and maintains a record of the locations of badge 12. Based on this information, a caregiver is better able to assess whether a patient is keeping the cast elevated for a given duration during the day or other activities.

In one embodiment, ABT 10 is configured to carry out activities based on the location of an asset. For example, ABT 10 may be configured, such that once a caregiver enters a patient room a computer is booted or access to the computer is provided such that the caregiver can interface with patient care programs on the computer. Further, door locks may be disabled or lighting adjusted based on the location of the caregiver in the patient room. Additionally, a nurse call indicator may be automatically reset once the caregiver enters the room.

Figure 10:
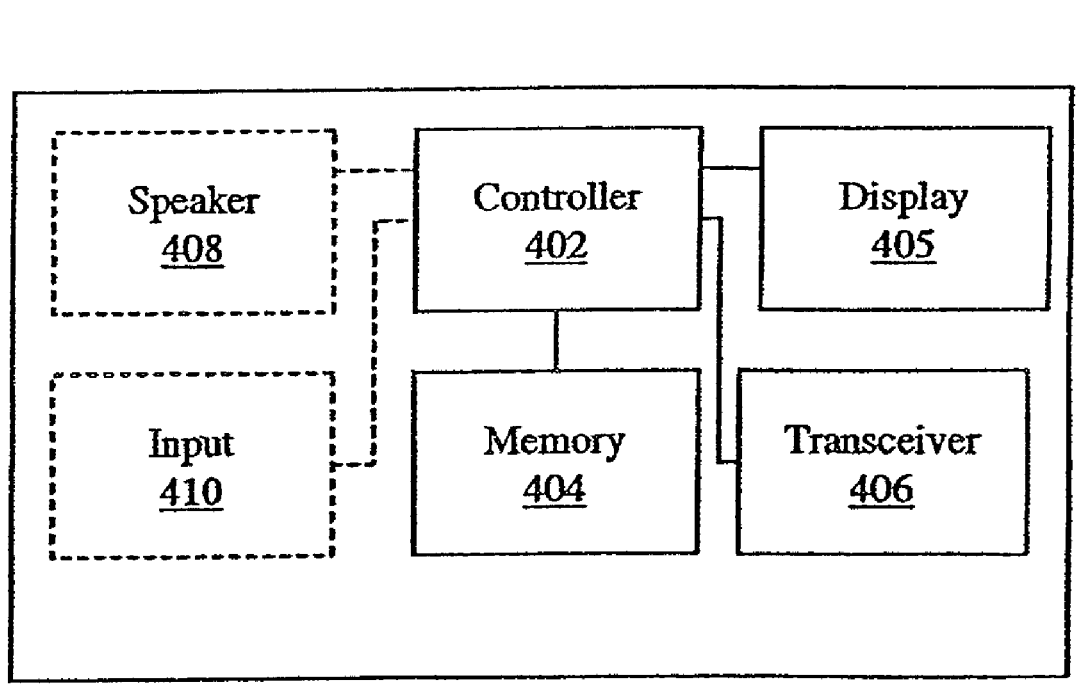
FIG. 10 illustrates a portable unit for use with the activity based tracking system.

In one embodiment, a portable device 400 is provided to a person, such as a caregiver. Referring to FIG. 10, portable device 400 includes a controller 402, a memory 404, a display 405, and a transceiver 406. Portable device 400 is configured to generate a request signal requesting the location of an asset and to receive a location signal including an indication of the location of the asset. Portable device 400 may be a badge, generally similar to badge 12, a portable data assistant, a cellular phone, a pocket PC, or other similar portable device.

Portable device 400 is configured to provide the associated person with instructions to direct the person to the requested asset. In one example, portable device 400 provides at least one of audio and visual instructions. The audio instructions are provided with an optional speaker 408. In another example, portable device 400 provides compass type directions. For example, portable device 400 provides on display 405 a direction-indicating symbol, such as an arrow that points in the direction to travel along a route to reach the location of the asset. An exemplary system for directing a person to a specified location in a facility with a portable device is provided in co-pending application Ser. No. 09/798,398, filed on Mar. 2, 2001, now U.S. Pat. No. 6,622,088 and titled "AMBULATORY NAVIGATION SYSTEM," the disclosure of which is expressly incorporated herein by reference.

In one example, display 405 provides a map of the facility. The map provides an indication of the location of the portable device, the location of the requested asset, and a suggested route to the asset. In one example, the route to the asset is shown in a different color than the rest of the map. Further, the suggested route may be chosen based on the shortest distance or the shortest time to the asset. The shortest time, in one example, being determined based on the potential congestion in various locations along potential routes.

In one example, the asset is in a location to which the user of the portable device does not have access. In such a case, the portable device 400 may direct the user of the portable device to a location that is not the current location of the asset. For example, wherein the asset is a piece of equipment which must be checked out from an equipment room, the portable device 400 directs the user to a clerk associated with the equipment room. In another example, wherein the asset is a patient currently in surgery, the portable device 400 directs the user to a waiting room assigned to the surgical area wherein the patient is located. Additionally, the portable device may communicate to the user that the patient is still in surgery. The user may then add the asset to a watch list which instructs the portable device 400 to request updates regarding the location of the asset and to provide instructions or an indication when the patient has left surgery and is in recovery.

In one embodiment, the map is a three-dimensional map. In one example, the three-dimensional map changes as the user of portable device 400 progresses through the facility. For example, as the user walks forward the map progresses forward to show the environment corresponding to the location of the user. In one case, as the user approaches a bank of elevators, the elevators appear on the three-dimensional map. Further, the map may include tagged assets along the route such as beds, caregivers, and equipment that are shown based on the current location of such tagged assets.

The portable device 400 further includes an input device 410 which allows the user to enter information such as a request for a specific asset or type of asset. Example input devices include a touch screen, a touch pad, a mouse, a light pen, a roller ball, a keyboard, a keypad, or one or more input keys. Assuming a user enters a request for an asset, ABT 10 locates the asset using the associated locating system and, based on an indication that the asset is available, issues a command to have the asset brought to the requested location. The command issued by ABT 10 may result in an orderly being called to retrieve the asset or the activation of a robot unit to retrieve the asset. In another example, the user also enters a requested destination location for the asset. In another example, the requested destination location is the location of the user at the time the request is made.

In one embodiment, the ABT system 10 provides a virtual facility corresponding to the actual facility that contains ABT 10. The virtual facility includes representations of the various assets having badges 12 associated therewith and physical structures, such as walls, elevators, cafeterias, and restroom facilities to name a few. In one example, the representations of the assets are selected from a library of images corresponding to various assets. For example, bed 16 may have multiple images associated therewith, one corresponding to bed 16 being in a low position and another corresponding to bed 16 having a raised head section. The images stored in the image library may be selected from two-dimensional images and three-dimensional models, such as models for use by a VRML (virtual reality modeling language) based system.

The images corresponding to the assets are located in the virtual facility based on their current locations as recorded by the locating system associated with ABT 10. Further, the images may be animated to simulate movement or use. For example, a person walking in the facility may be animated in the virtual facility to simulate walking. Also, if the person associated with badge 12 has an associated personal image, such as the person's face then that image may be shown. In another example, an I/V pump may include an animation to indicate that it is currently turned on and is pumping.

The virtual facility may be presented to a user or caregiver through a virtual facility interface, such as portable device 400, through a computer interface located within the facility, such as at a caregiver station or in a patient room, or through a virtual reality system including goggles to be worn by the user. The virtual reality system, in one example, places the user in a three-dimensional representation of the facility.

Through the virtual facility interface the user may select an asset, such as bed 16. In one example, the user has the option to be presented with information related to the asset, such as maintenance records, specifications, manuals, status, history, prior locations, and other asset related information. In another example, the user can obtain information related to an alarm status associated with the asset. In yet another example, the user may change the status of the asset. For instance, a caregiver may send a signal to bed 16 to raise siderail 26. As such, the caregiver may remotely change the status or configuration of an asset via the virtual reality interface.

In one embodiment, the virtual reality interface color-codes assets based on their status. For example, bed 16 may be shown in red if an alarm is associated with bed 16 or bed 16 may be shown in yellow indicating that bed 16 needs attention, such as a linen change. Further, assuming the user of virtual reality interface has a badge associated therewith, the user may receive status information about himself/herself. For example, the user might be shown in red if the user is currently contaminated and needs to wash his or her hands. Details on what constitutes a contamination and methods and apparatuses for monitoring handwashing are disclosed in copending U.S. patent application Ser. No. 09/699,796, filed Oct. 30, 2000 which is expressly incorporated by reference.

FIGS. 11-23 provide additional exemplary locating and tracking systems for use with ABT system 10. Many of the following locating and tracking systems are configured to determine the location of an asset and/or to track the location of the asset through use of various transceivers located throughout a facility and badges associated with the assets. The badges are configured to generate an ID signal that provides an indication of the asset associated with the respective badge. Further, each of the locating and tracking systems is configured to be implemented as part of ABT system 10 or as stand-alone location and tracking systems.

It should be noted that the concepts described in each locating system can be combined with the concepts of the other locating systems to create hybrid-type locating systems. For instance, each of the exemplary locating systems can include ARP sensors 20 or ARP-style transmitters positioned at various locations, such as in doorways or other locations.

In one example, the location of an asset is determined by identifying which transceiver receives an ID signal from a badge associated with the asset. An infrared (IR) line-of-sight tracking system is one type of such locating and tracking system. Another type is the passive RF transmitters and ARP sensors 20 discussed above. The system knows that the asset is generally in the area of the transceiver receiving the signal from the badge. In one variation, signal strength of the ID signal received from the badge is used to better approximate the location of the corresponding asset relative to the transceiver, as further described below. In another variation, the badge is interrogated or caused to send the ID signal and the time it takes for the signal to reach the transceiver is used to better approximate the location of the corresponding asset relative to the transceiver, as further described below.

In another example, the location of an asset is determined by two or more fixed-location transceivers that each receive an ID signal from the badge associated with the asset. Such systems determine the location of the asset by determining a distance measurement for each transceiver that is indicative of the distance from the respective transceiver to the badge. The distance measurements for the transceivers are then used to determine the location of the asset in either two dimensions or three dimensions. In one variation, the distance measurements are based on the time it takes for the ID signal from the badge to reach each transceiver. In another variation, the distance measurements are based on the signal strength of the ID signal received at each transceiver. In yet another variation, the distance measurements are based on a combination of both time and signal strength. The location of the asset may be classified as being within a given region or zone of an area of interest or as being within a sphere of space having a center that corresponds to the best approximation of the asset location and a periphery corresponding to the resolution of the system.

In yet another example, the location of an asset is determined based on location signals sent by a badge to a central receiver. In this example, the badge receives signals from at least one of the fixed transmitters, each of the fixed transmitters generating a unique ID signal. The badge then either generates a location signal including the received transmitter ID along with an ID associated with the badge to the central receiver or determines its own location and generates a location signal including the determined location and the associated badge ID to the central receiver. Either way the location of the badge is determined based at least in part on the received transmitter IDs. In one variation, the location of the badge is determined based on the received transmitter IDs. In another variation, the location of the badge is determined based on the received transmitter IDs and at least one of signal strength or timing information.

Figure 11:
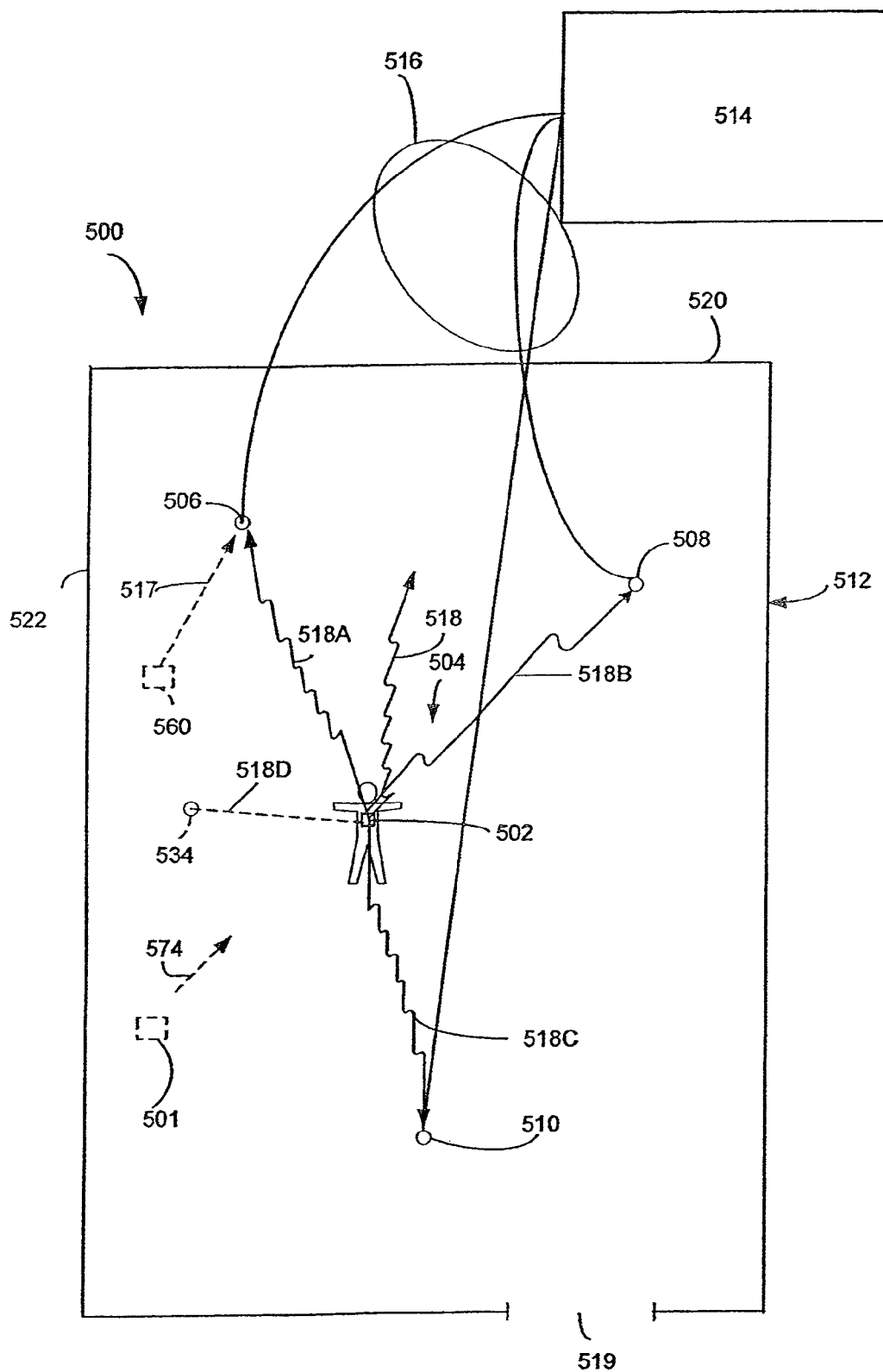
FIG. 11 illustrates an exemplary locating and tracking system of the present invention.

Referring to FIG. 11, one exemplary locating and tracking system 500 of the present invention is shown. System 500 includes a badge or tag 502, which is attached to or otherwise associated with an asset 504, three fixed transceivers 506, 508, 510 mounted at known locations within an area 512 such as a hospital room, and a central computing device 514, such as master station 34, connected to transceivers 506, 508, 510 via a wired or wireless connection referred to by the numeral 516. In one example, locating system 500 including one or more ARP sensors 20 which are located at various locations, such as proximate a doorway 519, and are connected to central computing device 514.

Badge 502 is generally similar to badge 12 and includes at least one of a passive RFID transmitter, an active RF transmitter, an active IR transmitter, an ultrasound transmitter, or other suitable transmitter configured to emit or generate an identification (ID) signal traveling in free space. Transceivers 506, 508, 510 each include a sensor to detect the ID signal being generated by badge 502 and/or to excite badge 502 to generate the ID signal. It should be noted that the term transceiver is used to denote devices at least configured to receive an ID signal from a badge, such as badge 502. Further, as explained herein, in some embodiments and examples the transceivers are further configured to transmit an excitation signal which is received by the badges and in turn causes the badges to transmit an ID signal.

In one embodiment, badge 502 includes an active RF transmitter (not shown) that transmits an ID signal uniquely associated with the asset 504. Power may be supplied to badge 502 by a battery (not shown) as is well known in the art. In another embodiment, badge 502 may further include an antenna (not shown) that receives an excitation signal from a transceiver 506, 508, 510 when within the range of the transceiver according to conventional techniques. The same antenna may be used to transmit the ID signal associated with badge 502. Badge 502 in one example is an RFID tag which provides an ID signal associated with asset 504 in response to receiving an excitation signal from at least one of transceivers 506, 508, 510. As such, badge 502 may be configured to emit an ID signal at a predetermined time interval, to emit an ID signal at random time intervals, to emit an ID signal at varying time intervals based on a characteristic of asset 504, or in response to the reception of an excitation signal. In one example, badge 502 includes a displacement sensor and badge 502 transmits its associated ID signal at two or more transmission rates depending on the output of the displacement sensor.

When badge 502 is configured to generate or emit the ID signal at a predetermined interval, transceivers 506, 508, 510 are configured to detect the emission of the ID signal. However, when badge 502 is configured to emit the ID signal in response to reception of an excitation signal, transceivers 506, 508, 510 are configured to transmit an excitation signal that has sufficient strength to be received by badge 502 anywhere within area 512. As such, transceivers 506, 508, 510 include at least one of an RFID exciter, a RF receiver, an RF transmitter, an RF transceiver, an IR receiver, an IR transmitter, an IR transceiver, an ultrasound receiver, an ultrasound transmitter, or other suitable receivers, transmitters, or transceivers configured to receive ID signals from badge 502 and/or configured to cause badges 502 to generate and transmit an ID signal.

Each transceiver 506, 508, 510 further includes a detection circuit (not shown) that performs a badge locating function as is further described below. The badge locating function corresponds to the calculation of a distance measurement associated with badge 502. As stated above and explained in more detail below, the distance measurement for a given badge is based on at least one of signal strength or timing information.

In operation, an asset 504 having a badge 502 associated therewith moves into area 512. Assuming badge 502 generates the corresponding ID signal in response to an excitation signal, when asset 504 enters area 512, the antenna of asset 504 receives excitation signals from at least one of transceivers 506, 508, 510. Badge 502 responds to receipt of any excitation signal by transmitting its ID signal via its antenna. Alternatively, badge 502 includes an active RF transmitter and transmits the associated ID signal at a predetermined time interval or a random time interval. As such, transceivers 506, 508, 510 do not need to send excitation signals to initiate transmission of the ID signal from badge 502. In one example, badge 502 includes a motion detector or displacement sensor and the transmission rate of the ID signal is dependent upon the status of the motion detector or displacement sensor.

When badge 502 transmits its ID signal either due to reception of an excitation signal or at a predetermined or random time interval, transceivers 506, 508, 510 receive the ID signal, process it, and transmit location signals to central computing device 514. In one example, transceivers 506, 508, 510 are all positioned in room 512 at approximately the same height or altitude. In another example, at least one of transceivers 506, 508, 510 is positioned at a different height or altitude than the remaining transceivers 506, 508, 510.

Referring to FIGS. 11-13C, each transceiver 506, 508, 510 or central computing device 514 determines based at least in part on the received ID signal from badge 502 a distance measurement 524, 526, 528 corresponding to the respective transceiver 506, 508, 510. The distance measurement corresponds to the distance between badge 502 and the respective transceiver 506, 508, 510. As illustrated in FIG. 11, badge 502 generates an ID signal 518 which is detected by transceivers 506, 508, 510. Illustratively, transceiver 506 detects ID signal 518A, transceiver 508 detects ID signal 518B, and transceiver 510 detects ID signal 518C. It should be noted that ID signals 518A, 518B, 518C all contain the same information, however, each may have different signal strengths due to the distance between badge 502 and transceivers 506, 508, 510. Referring to FIG. 13A, ID signal 518A corresponding to transceiver 506 results in a calculated distance measurement 524 of three feet, ID signal 518B corresponding to transceiver 508 results in a calculated distance measurement 526 of eight feet, and ID signal 518C to transceiver 510 results in a distance measurement 528 of ten feet. In one embodiment, distance measurements 524, 526, 528 are calculated by either the respective transceiver 506, 508, 510 or the central computing device 514. In other embodiments, the distances are calculated by 502 and transmitted to transceivers 506, 508, 510.

Figure 12:
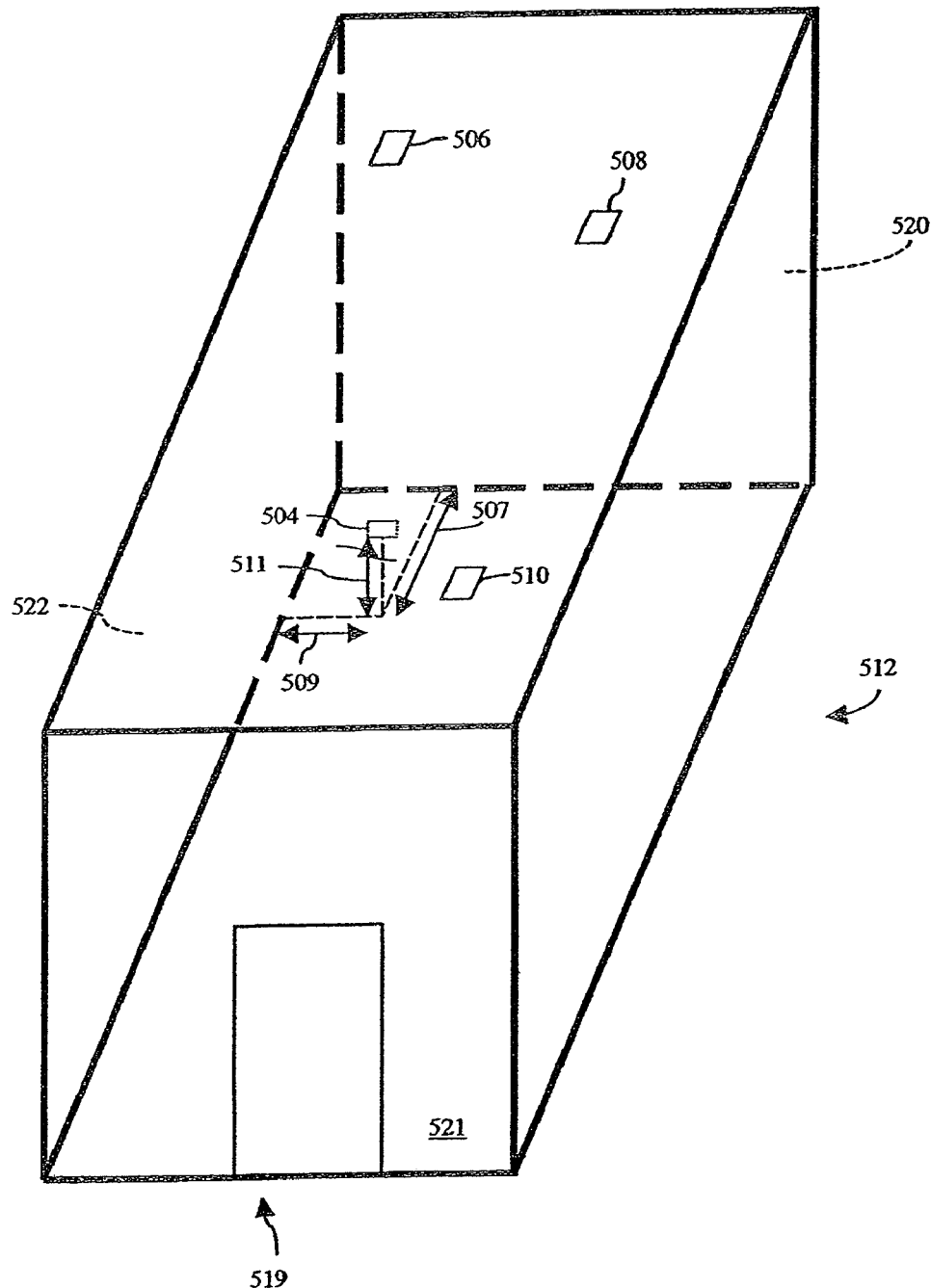
FIG. 12 illustrates the location of an asset in an area of interest.

Once the distance measurements have been calculated central computing device 514 may access stored location information corresponding to the fixed locations of transceivers 506, 508, 510 and apply known mathematical techniques to determine a location of asset 504. In a three-dimensional system, illustratively shown in FIG. 12, central computing device 514 determines that asset 504 is located a distance 507, from wall 520 of area 512, such as five feet, a distance 509, from wall 522, such as five feet, and a distance 511 above floor 521, such as four feet. In a two-dimensional system, central computing device 514 will apply known mathematical techniques to determine that asset 504 is a distance 507 from wall 520 of area 512 and a distance 509 from wall 522 of area 512. As asset 504 moves within area 512, the above-described process is periodically repeated to maintain up-to-date location information relating to asset 504. The example illustrated in FIG. 12 shows the distance information in Cartesian coordinates. However, it is within the scope of the present invention to report location information in other formats, including a zone designation or spherical coordinates.

Figure 13A:
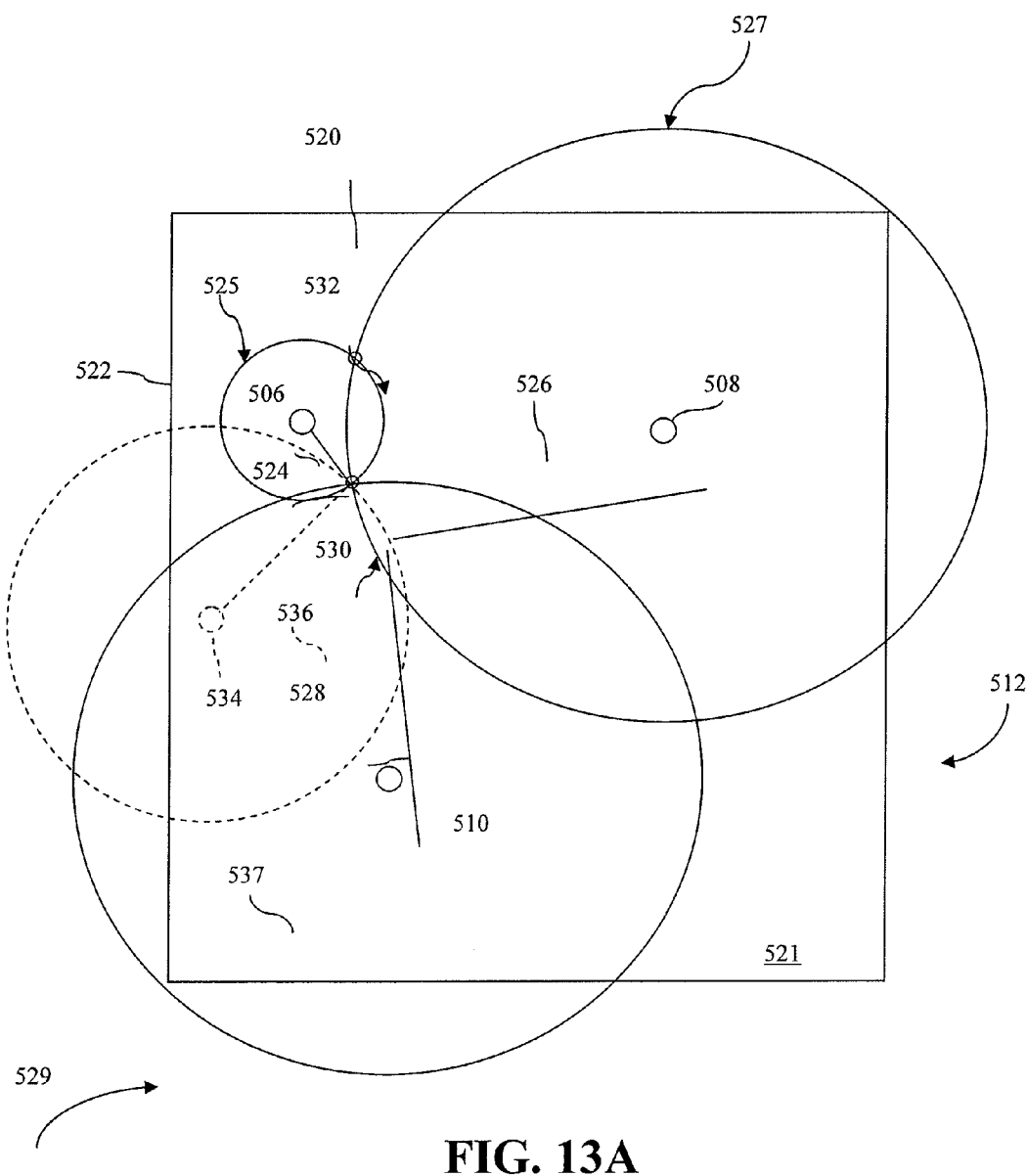
FIG. 13A provides an illustration of one method of determining the location of an asset with the system of FIG. 11 in three dimensional space.

In one three-dimensional embodiment, locating system 500 uses simple triangulation to determine the location of asset 504 based on distance measurements 524, 526, 528. FIG. 13A corresponds to a diagrammatic view of a plane generally parallel to floor 521 and coincident to an altitude of asset 504. As shown in FIG. 13A, distance measurement 524 corresponding to transceiver 506 indicates that asset 504 is approximately located on the circumference of a sphere 525 (shown as a circle in the plane shown in FIG. 13A) having a radius of three feet equal to distance measurement 524. Further, distance measurement 526 corresponding to transceiver 508 indicates that asset 504 is approximately located on the circumference of a sphere 527 (shown as a circle in the plane shown in FIG. 13A) having a radius of eight feet equal to distance measurement 526. As such, based on distance measurements 524 and 526, locating system 500 may narrow the location of asset 504 to approximately a circle in three-dimensional space and either location 530 or location 532 in the plane shown in FIG. 13A, both of which are intersections of spheres 525 and 527. The ambiguity in the location of asset 504 is resolved by distance measurement 528 corresponding to transceiver 510, which indicates that asset 504 is approximately located on the circumference of a sphere 529 (shown as a circle in the plane shown in FIG. 13A) having a radius of ten feet equal to distance measurement 528. Sphere 529 most closely intersects with spheres 525 and 527 at location 530. Therefore, locating system 500 may deduce that the location of asset 504 is location 530.

It should be understood that the location of asset 504 in at least one instance is determined by the closest positioning of spheres 525, 527, 526 relative to each other because one or more of spheres 525, 527, 529 does not intersect at least one of the other of spheres 525, 527, 529, or that the intersection of a first pair of spheres 525, 527, 529 does not coincide with the intersection of a second pair of spheres 525, 527, 529. The determination of the location of asset 504 may be enhanced by adding additional transceivers to room 512, such as transceiver 534 shown in FIGS. 11 and 13A, which is generally similar to transceivers 506, 508, 510 and receives ID signal 518D from badge 502 of asset 504. Transceiver 534 provides an additional distance measurement 536 and corresponding sphere 537 (shown as a circle in the plane shown in FIG. 13A). By looking at the distance measurements 524, 526, 528, 536, locating system 500 can better pinpoint the location of asset 504. For example, the location of asset 504 can be determined using distance measurements 524, 526, 528, 536 and a least squares algorithm or other known mathematical techniques.

Figure 13B:
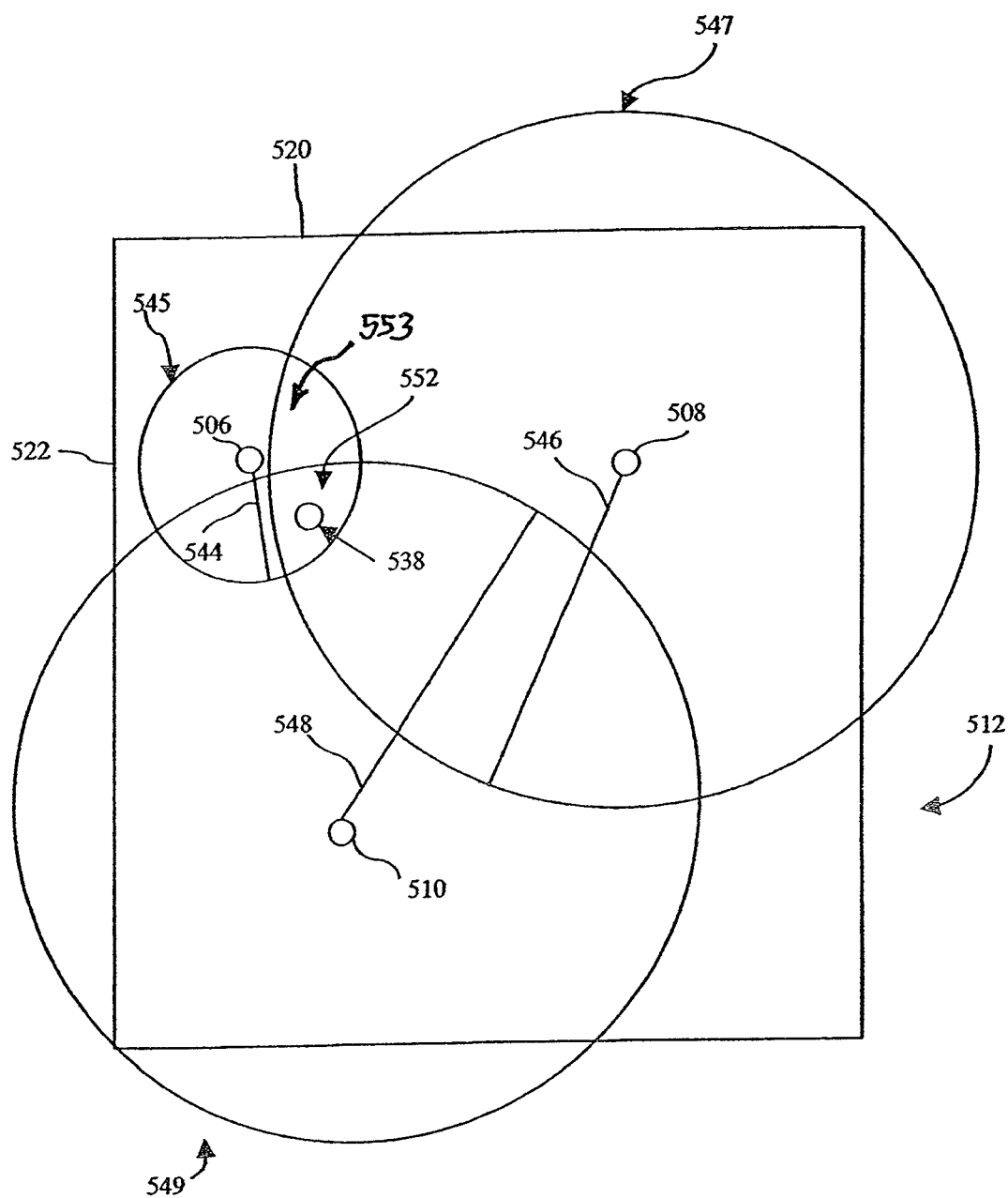
FIG. 13B provides an illustration of one method of determining the location of an asset with the system of FIG. 11 in two dimensional space.

In one two dimensional embodiment, locating system 500 uses triangulation to determine the location of asset 504 based on distance measurements 524, 526, 528. FIG. 13B corresponds to a diagrammatic view of a plane generally parallel to floor 521, and not coincident to an altitude of asset 504. It should be noted that if the plane of FIG. 13B was coincident to an altitude of asset 504, FIG. 13B would be identical to FIG. 13A. However, the plane FIG. 13B was chosen to not be coincident with an altitude of asset 504 to better illustrate characteristics of a two-dimensional location determination that does not account for the altitude of an asset.

Figure 13C:
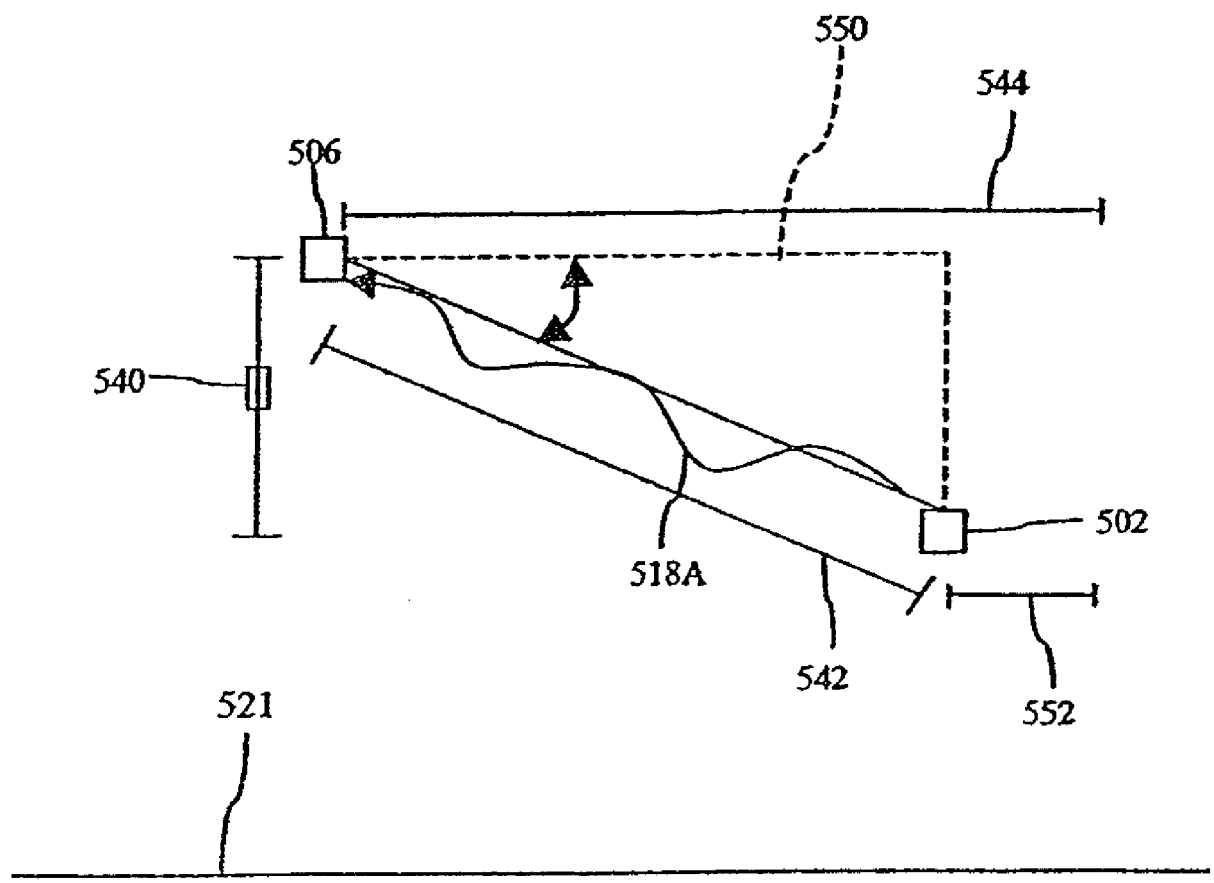
FIG. 13C illustratively shows the effect of differing altitudes on the two dimensional location of FIG. 13B.

Referring to FIG. 13C, badge 502 transmits ID signal 518A to transceiver 506. As shown in FIG. 13C, badge 502 is at a different altitude (represented by a distance 540) relative to floor 521 than transceiver 506. Further, badge 502 in reality is located a distance 542 from transceiver 506. As such, based on either signal strength or timing information, or a combination of both signal strength and timing information, transceiver 506 or central computing device 514 will determine a distance measurement 524 generally equal in magnitude to distance 542.

Distance measurements 524, 526, 528 of transceivers 506, 508, 510, respectively, indicate that asset 504 is located as respective circles 545, 547, 549. However, as shown in FIG. 13B, circles 545, 547, 549 do not intersect at generally the same location. This is due to the fact that distance measurements 524, 526, 528 include a component corresponding to the difference in altitude between badge 502 and respective transceivers 506, 508, 510. As such, assuming that badge 502 is at a different altitude than all of respective transceivers 506, 508, 510, each distance measurement 544, 546, 548 will incorrectly overestimate a horizontal distance from respective transceiver 506, 508, 510 to badge 502 such as horizontal distance 550 between transceiver 506 and badge 502 as shown in FIG. 13C. In fact, distance measurement 544 overestimates horizontal distance 550 by a distance 552.

Referring to FIG. 13B, locating system 500 may determine that the location of asset 504 is within a region 552 bounded by circles 545, 547, 549. In one example, the location of asset 504 is assumed to be the center 538 of region 552. For some applications, the knowledge that asset 504 is located within region 552 may be sufficient, while for other applications the extent of region 552 may need to be reduced to increase the accuracy of the estimated location of asset 504. It should be understood that if lower resolution is acceptable, only two transceivers are required, such as transceivers of 506 and 508, and asset 504 is assumed to be located in region 553 (which includes region 552) corresponding to the overlap of circles 545 and 547.

One method to reduce the extent of region 552 is to utilize characteristics of an asset to better estimate distance measurements 544, 546, 548 or to modify distance measurements 544, 546, 548 to account for the altitude of badge 502. For instance, it might be known that all I/V poles have associated badges 502 placed three feet from floor 521. As such, when central computing device 514 receives a set of distance measurements, such as distance measurements 544, 546, 548, corresponding to an I/V pole, central computing device 514 knows to modify distance measurements 544, 546, 548 to account for differences in altitude between badge 502 and respective transceivers 506, 508, 510. Referring to FIG. 13C, central computing device 514 will modify distance measurement 544 to be generally equal to distance 550 with known trigonometric relations by knowing measured distance measurement 544 and by knowing distance 540.

In one variation of system 500, the detection circuit of each transceiver 506, 508, 510 includes a signal strength detector. As such, each detection circuit includes electronics for determining the strength of ID signals received from badges 502. Transceivers 506, 508, 510 in this variation of system 500 may further include electronics and/or software for converting the determined signal strength into a distance measurement, which is communicated to central computing device 514 for processing. Alternatively, transceivers 506, 508, 510 may simply transmit signal strength measurements to central computing device 514, which includes hardware and/or software for performing the conversion to distance.

In one example, the signal strength is converted to a distance measurement by comparing the received signal strength to known signal strengths corresponding to known distances. In another example, the signal strength is compared to the signal strength of fixed badges whose location and hence distance to transceivers 506, 508, 510 is known. An illustrative fixed badge 560 is shown in FIG. 11. Fixed badge 560 generates an ID signal 517 including a unique identifier associated with fixed badge 560. Transceiver 506, as representative of transceivers 506, 508, 510, receives ID signal 517 and determines the signal strength of ID signal 517. Distance measurement 524 is determined by multiplying a ratio of the signal strength of ID signal 518 A and the signal strength of ID signal 517 by the known distance to fixed badge 560. In one case, the distance measurement 524 is determined from the signal strength of ID signals from a plurality of fixed badges.

In yet another example, transceiver 506 sends out an excitation signal to badge 502 which generates an ID signal. The excitation signal includes a unique identifier or ID associated with transceiver 506. Badge 502 is configured to determine the signal strength of the received excitation signal. The ID signal generated by badge 502 includes the ID received from transceiver 506, an ID associated with badge 502, and the signal strength of the received excitation signal. By including the received transceiver ID, transceivers 506, 508, 510 can determine to which transceiver badge 502 is responding.

Transceiver 506 or central computing device 514 then computes, for example, distance measurement 524 based either on the reported signal strength of the excitation signal or the reported signal strength of both the excitation signal and the received ID signal. Either way, the above-mentioned signal strengths are compared to either known signal strengths or signals strengths from one or more fixed badges 560. In one case, fixed badges 560 may also include in their ID signals the received transceiver ID and the signal strength of the received excitation signal.

In the example shown in FIG. 11, the ID signals received by transceivers 506, 508, 510 are labeled 518A, 518B, and 518C, respectively. ID signal 518A may be a relatively weak signal, or have a low signal strength, as detected by transceiver 506 because of the relatively long distance between badge 502 and transceiver 506. ID signal 518C, on the other hand, may be a relatively strong signal, or have a high signal strength, as detected by transceiver 510 because of the relatively short distance between badge 502 and transceiver 510. ID signal 518B may have a signal strength that falls between the strengths of ID signals 518A and 518C. When the signal strengths are converted to distance measurements 524, 526, 528, either by transceivers 506, 508, 510 or by central computing device 514, central computing device 514 may determine the location of asset 504 by using the known locations of transceivers 506, 508, 510. In one embodiment, locating system 500 determines the location of asset 504 in two-dimensions, such as the location of asset 504 in area 512 (without regard to altitude) as explained above in connection with FIGS. 11, 13B and 13C. In another embodiment, locating system 500 determines the location of asset 504 in three-dimensions, such as the location of asset 504 in area 512 and relative to floor 521 of area 512 as explained above in connection with FIGS. 11, 12, and 13A.

In another variation of system 500, the detection circuit of each transceiver 506, 508, 510 includes a timer circuit, electronics, such as for determining the time required to transmit an excitation signal to badge 502 and receive an ID signal in response. Transceivers 506, 508, 510 in this variation of system 500 may further include electronics and/or software for converting the determined time required to transmit an excitation signal to badge 502 and to receive an ID signal in response into a distance measurement which is communicated to central computing device 514 for processing. Alternatively, transceivers 506, 508, 510 may simply transmit the timing information to central computing device 514, which includes hardware and/or software for performing the conversion to a distance measurement. The calculated distance measurement includes a known badge delay, $t_{BD}$, corresponding to the time required for badge 502 to process the excitation signal and generate an ID signal.

Figure 14A:
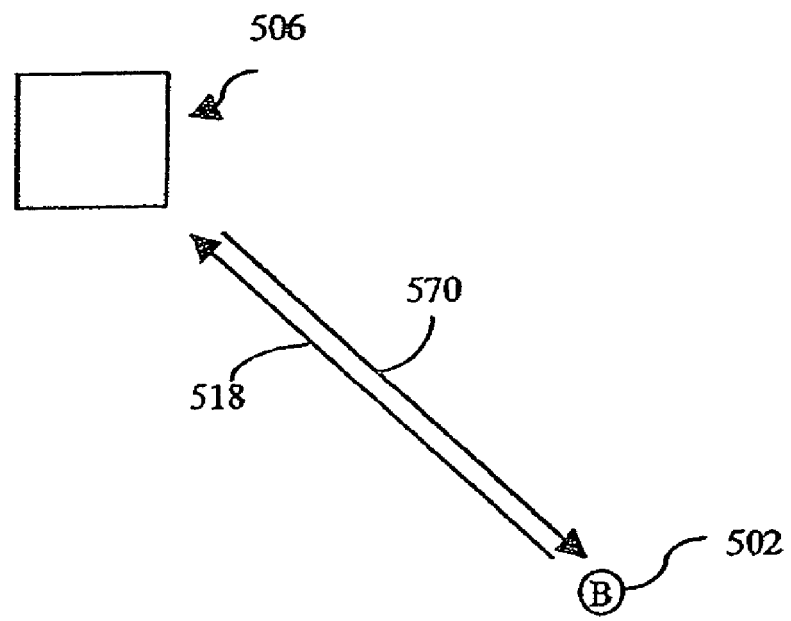
FIG. 14A illustrates an exemplary interaction between a transceiver and a badge of the exemplary locating and tracking system of FIG. 11.
Figure 14B:
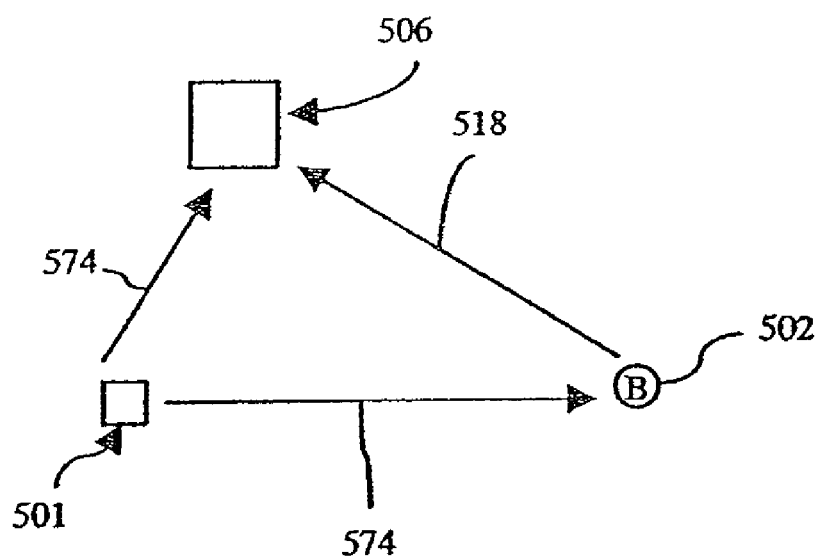
FIG. 14B illustrates an exemplary interaction between a fixed transmitter or pinger, a transceiver and a badge of the exemplary locating and tracking system of FIG. 11.

FIGS. 14A-14B illustrates several examples of interactions between transceiver 506 and badge 502 for the calculation of distance measurement 524. It should be understood that the interactions between badge 502 and transceivers 508 and 510 are generally similar to the interactions between badge 502 and transceiver 506. Referring to FIG. 14A, a first example of the interaction between badge 502 and transceiver 506 is shown. As shown in FIG. 14A, transceiver 506 generates a excitation signal 570 which is received by badge 502. In one example, excitation signal 570 includes an ID that is unique to transceiver 506. Badge 502 responds by generating an ID signal 518. In one example, the badge ID signal 518 includes the received transceiver ID and an ID that is unique to badge 502. By including the received transceiver ID, transceivers 506, 508, 510 can determine to which transceiver badge 502 is responding.

The distance measurement calculated by either transceiver 506 or central computing device 514, in one example, corresponds to equation 1 below, wherein D is the calculated distance measurement, $v$ is the propagation speed of the generated signals (IR, RF, ultrasound, etc.), $t_E$ is the time period for excitation signal 570 to reach badge 502, $t_{BD}$ is the time period for badge 502 to process excitation signal 570 and generate ID signal 518, and $t_{BT}$ is the time period for badge ID signal 518 to reach transceiver 506.

$$D = \frac{v(t_E + (t_{BT} - t_{BD}))}{2} \quad (1)$$

As explained above in connection with FIGS. 12 and 13A-C, the distance measurements for each transceiver are used to estimate the location of badge 502 in either two-dimensional space or three-dimensional space.

In one example, transceiver 506 and badge 502 generate signals using different signal types. For example, transceiver 506 might generate an RF signal and badge 502 might generate an ultrasound signal. In such a situation, the propagation speed of each signal is different. Therefore, equation 1 must be modified to account for the different propagation speeds. Equation 2 provides the distance measurement for the example when transceiver 506 and badge 502 generate signals of different propagation speeds wherein $v_T$ is the propagation speed of the signal generated by transceiver 506 and $v_B$ is the propagation speed of the signal generated by badge 502.

$$D = \frac{v_T t_E + v_B(t_{BT} - t_{BD})}{2} \quad (2)$$

Referring to FIG. 14B, a second example of the interaction between badge 502 and transceiver 506 is shown wherein transceiver 506 does not generate an excitation signal 570. As such, transceiver 506 may be a simple receiver. As shown in FIG. 14B, a fixed location pinger (transmitter) 501 generates an excitation signal 574 which is received by both transceiver 506 and badge 502. In one example, a plurality of fixed pingers, similar to fixed pinger 501, are provided. In one example, excitation signal 574 includes an ID that is unique to pinger 501. In another example, excitation signal 574 includes a time-stamp. In yet another example, excitation signal 574 includes both a unique pinger ID and a time-stamp.

Badge 502 responds to the reception of excitation signal 574 by generating an ID signal 518. In one example, ID signal 518 includes an ID that is unique to badge 502. In another example, ID signal 518 includes a time-stamp. In yet another example, ID signal 518 includes both a unique badge ID and a time-stamp. In a further example, ID signal 518 includes at least one of a badge ID and a badge timestamp along with the information or an indication of the information received in excitation signal 574 selected from a pinger ID and a pinger timestamp. By including the received pinger ID or timestamp, transceivers 506, 508, 510 can determine to which pinger signal(s) 574 badge 502 is responding.

Transceiver 506 receives both excitation signal 574 from pinger 501 and ID signal 518 from badge 502. The distance measurement calculated by either transceiver 506 or central computing device 514, in one example, corresponds to equation 3 wherein D is the calculated distance measurement, $v$ is the propagation speed of the generated excitation and ID signals (IR, RF, ultrasound), $t_{PB}$ is the time period for excitation signal 574 to reach badge 502, $t_{BD}$ is the time period for badge 502 to process excitation signal 574 and to generate ID signal 518, $t_{BT}$ is the time period for badge ID signal 518 to reach transceiver 506, and $t_{PT}$ is the time period for excitation signal 574 to reach transceiver 506.

$$D = v[(t_{PB} + (t_{BT} - t_{BD})) - t_{PT}] \quad (3)$$

As explained above in connection with FIGS. 12 and 13A-C, the distance measurements for each transceiver are used to estimate the location of badge 502 in either two-dimensional space or three-dimensional space.

In one example, pinger 501 and badge 502 generate signals using different signal types. For example, pinger 501 might generate an RF signal and badge 502 might generate an ultrasound signal. In such a situation the propagation speed of each signal is different. Therefore, equation 3 must be modified to account for the different propagation speeds. Equation 4 provides the distance measurement for the example when pinger 501 and badge 502 generate signals of different propagation speeds wherein $v_P$ is the propagation speed of the signal generated by pinger 501 and $v_B$ is the propagation speed of the signal generated by badge 502.

$$D = v_P t_{PB} + v_B(t_{BT} - t_{BD}) - v_P t_{PT} \quad (4)$$

In one example, $t_{BD}$ is set to be longer in duration than $t_{PT}$ such that the dependence on $t_{PB}$ in the calculation of D is reduced. In one case $t_{BD}$ is set equal to about five seconds.

Referring to FIG. 11, locating system 500, in one embodiment, includes at least one pinger 501 and transceivers 506, 508, 510. Transceivers 506, 508, 510 are connected to central computing device 514 through a wireless or wired connection. As shown in FIG. 11, asset 504 and associated badge 502 enter area 512. Badge 502 receives an excitation signal 574 from fixed pinger 501. Excitation signal 574, in one example, is generated at a predetermined time interval. In another example, excitation signal 574 is generated at two or more predetermined time intervals including a first time interval corresponding to a high activity time period, such as a day shift in a hospital ward, and a second time interval corresponding to a lower activity time period, such as a night shift in a hospital ward. In an alternative embodiment, at least one of transceivers 506, 508, 510 generates excitation signal 574. As such locating system 500 does not need a separate fixed pinger.

Excitation signal 574 is received by badge 502 and transceivers 506, 508, 510. Further, badge 502 generates ID signal 518 in response to excitation signal 574 that is received by transceivers 506, 508, 510. As explained above, either transceivers 506, 508, 510 or central computing device 514 determines a distance measurement 524, 526, 528 corresponding to the distance from transceiver 506, 508 510 to badge 502.

In one example, transceivers 506, 508, 510 and badges 502 are time synchronized (i.e., each precisely measures time from a common starting instant). Fixed pinger 501 generates an excitation signal 574. Badge 502 receives excitation signal 574 and generates ID signal 518 including a timestamp. ID signal 518 is received by transceivers 506, 508, 510. Transceivers record or otherwise denote the timestamp associated with the generation of ID signal 518. Since transceivers 506, 508, 510, and badges 502 are synchronized, by knowing the time ID signal 518 was generated and the time it was received, each transceiver can estimate a distance measurement corresponding to the distance of badge 502 from transceiver 506, 508, 510, respectively. At least two transceivers of transceiver 506, 508, 510 are needed to locate badge 502 in a two dimensional space, such as over floor 521 (without regard to altitude) as explained above in connection with FIGS. 11, 13B and 13C. At least three transceivers are needed to locate badge 502 in three dimensional space as explained above in connection with FIGS. 11, 12 and 13A. The determination of the location of badge 502 may be further enhanced by the implementation of additional transceivers, such as transceiver 534 shown in FIG. 11. (It should be noted that the time period corresponding to the delay associated with badge 502 processing the received excitation signal 574 and generating the ID signal 518 is taken into account by the transceiver 506, 508, 510 in calculating distance measurement 524, 526, 528 for badge 502.)

In another example, transceivers 506, 508, 510, badges 502 and fixed pinger 501 are time synchronized. Excitation signal 574 generated by fixed pinger 501 includes a timestamp. Each of transceivers 506, 508, 510 receive excitation signal 574 from pinger 501 and records or otherwise denotes the timestamp associated with excitation signal 574. Badge 502 receives excitation signal 574 and generates ID signal 518 including a timestamp and the timestamp associated with reception of excitation signal 574. ID signal 518 is received by transceivers 506, 508, 510. Transceivers record or otherwise denote the timestamp associated with the generation of ID signal 518. Since pinger 501, transceivers 506, 508, 510, and badges 502 are synchronized, by knowing the time excitation signal 574 was sent, the time excitation signal 574 was received by badge 502, and the time ID signal 518 was generated, each transceiver 506, 508, 510 may estimate a distance measurement corresponding to the distance of badge 502 from the respective transceiver 506, 508, 510.

By determining the distance measurement during, for example, three time periods instead of one, a better approximation of the distance from badge 502 to the respective transceiver can be made. Further, if the placement of pinger 501 and the respective transceiver are known, the loci of possible locations of badge 502 may be reduced from generally a sphere to generally a circle. At least two transceivers of transceiver 506, 508, 510 are needed to locate badge 502 in a two dimensional space, such as a plane over floor 521 as explained above in connection with FIGS. 11, 13 B, and 13C. At least three transceivers are needed to locate badge 502 in three dimensional space as explained above in connection with FIGS. 11, 12, 13A. The determination of the location of badge 502 may be further enhanced by the implementation of additional transceivers, such as transceiver 534 shown in FIG. 11. (It should be noted that the time period corresponding to the delay associated with badge 502 processing the received excitation signal and generating the ID signal is taken into account by the transceiver 506, 508, 510 in calculating the distance measurement 524, 526, 528 for badge 502.)

In another embodiment, transceivers 506, 508, 510 act as pingers and generate excitation signals which are received by badge 502 and by fixed badges, such as fixed badge 560 in FIG. 11. Both badge 502 and fixed badge 560 receive the generated excitation signals from transceivers 506, 508, 510 and generate an ID signal 517, 518 corresponding to the respective badge 502, 560. In one example the transceiver excitation signals include a transceiver ID and the badge ID signal signals include a badge ID and the received transceiver ID. By including the received transceiver ID, transceivers 506, 508, 510 are able to determine to which transceiver badges 502, 560 are responding.

A distance measurement for badge 502 is determined by transceivers 506, 508, 510 by comparing the round trip time (from generation of the excitation signal to reception of the respective ID signal) to receive ID signal 517 and the round trip time to receive ID signal 518. As stated previously, the location of fixed badge 560 is known and hence the round trip time corresponding to ID signal 517 may be equated to a distance value. Distance measurements 524, 526, 528 are determined by multiplying a ratio of the round trip time of ID signal 518 and the round trip time of ID signal 517 by the known distance to fixed badge 560.

Figure 15:
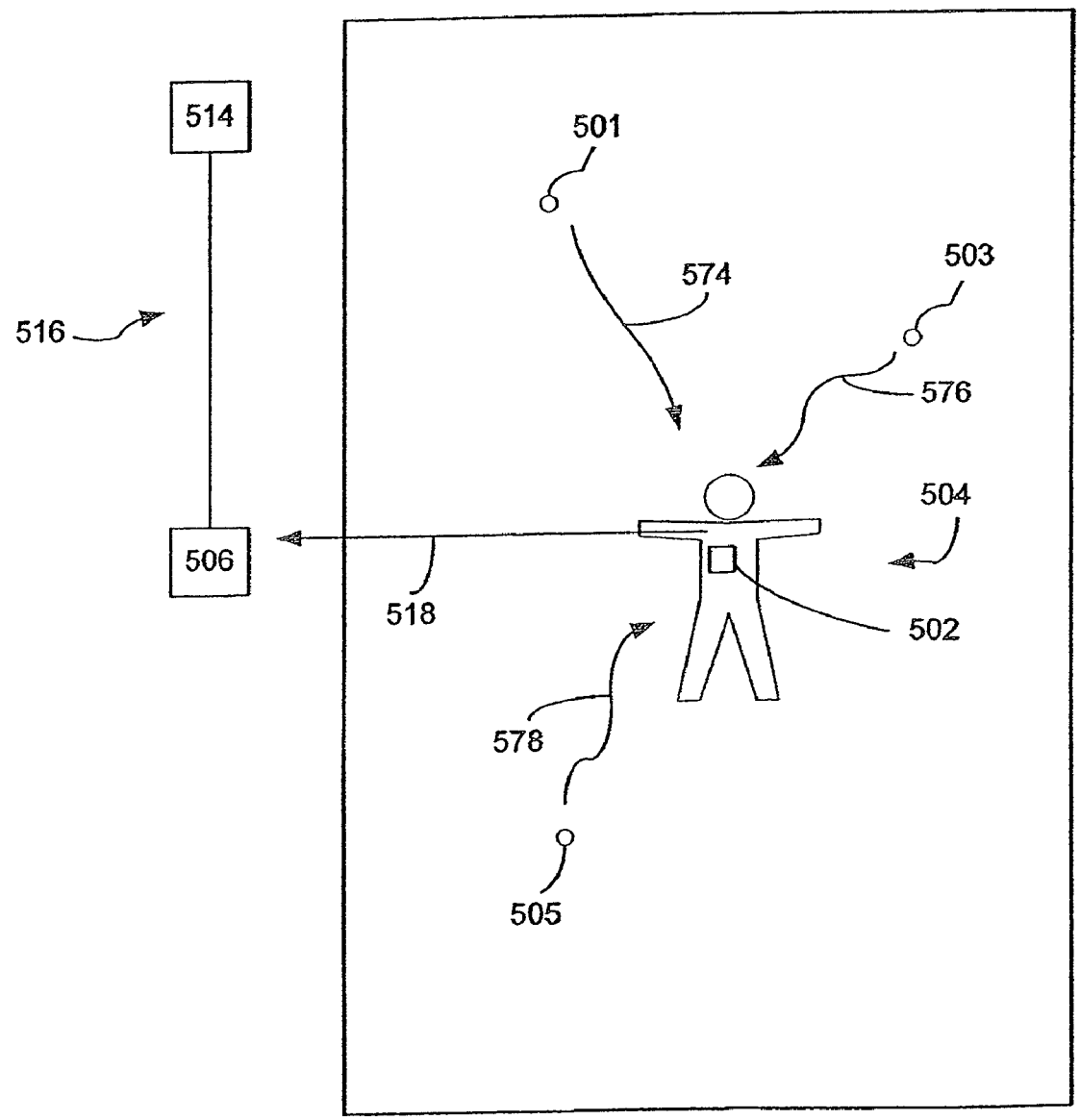
FIG. 15 illustrates the interactions between a badge and multiple fixed pingers of the exemplary locating and tracking system of FIG. 1, wherein the badge determines its location based on signals from the fixed pingers.

In another embodiment shown in FIG. 15, a single transceiver or receiver, such as transceiver 506, is provided in area 512 along with multiple fixed pingers, such as pingers 501, 503, 505. Each pinger is configured to generate an excitation signal, such as excitation signal 574, 576, 578, which is received by transceiver 506 and by a badge 502 associated with asset 504. Each excitation signal 574, 576, 578 includes a unique ID to identify the respective pinger 501, 503, 505. Badge 502, in response to receiving an excitation signal, generates an ID signal 518, which includes a unique ID associated with badge 502 and the unique ID of the pinger or pingers 501, 503, 505 which generated the received excitation signal.

In another example, badge 502 and fixed pingers 501, 503, 505 are synchronized and each pinger 501, 503, 505 generates an excitation signal 574, 576, 578 respectively. Excitation signal 574, 576, 578 includes a unique ID associated with the respective pinger 501, 503, 505 and a timestamp corresponding to the time of generation of the excitation signal 574, 576, 578. Badge 502 receives the excitation signals from each pinger 501, 503, 505 and determines a distance measurement between itself and pingers 501, 503, 505 and the location of itself based on time between the generation of the respective excitation signals 574, 576, 578 and the reception of the respective excitation signals 574, 576, 578 and a knowledge of the location of the respective pinger 501, 503, 505. At least two pingers of pingers 501, 503, 505 are needed to locate badge 502 in a two dimensional space, as explained above in connection with FIGS. 11, 12, 13A. At least three pingers are needed to locate badge 502 in three dimensional space as explained above in connection with FIGS. 11, 13B, 13C.

For instance, badge 502 may include a lookup table that includes the location of each fixed pinger, such that badge 502 can determine a loci of possible locations for itself based on knowing the location of the pinger similar to the spheres and circles discussed in relation with FIGS. 13A and 13B. In another instance, the unique ID included in the respective excitation signal 574, 576, 578 provides information related to the location of the respective fixed pinger 501, 503, 505. In one case, the unique ID is the location coordinates of the fixed pinger. As such, when badge 502 receives the respective excitation signal 574, 576, 578, badge 502 knows the location of the respective pinger 501, 503, 505 from the pinger ID and the distance badge 502 is from the respective pinger 501, 503, 505 based on the time difference between the generation of the respective excitation signal 574, 576, 578 and the reception of the respective excitation signal 574, 576, 578. In another case, badge 502 can use the signal strength of the respective excitation signals 574, 576, 578. Based on the signal strength information, badge 502 may determine a loci of possible locations for itself.

Once badge 502 determines its location, badge 502 generates ID signal 518 which is sent to receiver or transceiver 506. Receiver 506 forwards the location information on to central computing device 514. Since receiver 506 is not used in determining the location of badge 502, receiver 506 may be positioned at an arbitrary location and receive ID signals 518 from various areas, such as area 512. In one embodiment, badge 502 sends an RF ID signal 518 and receiver 506 is located in a hallway adjacent several rooms in a hospital ward. Since RF signals can penetrate walls, receiver 506 may receive signals from badges 502 positioned in several rooms of the hospital ward.

In one embodiment wherein badge 502 determines its own distance measurements and hence location, excitation signals 574, 576, 578 from pingers 501, 503, 505, respectively, are RF signals and ID signal 518 is an RF signal. As stated above, an advantage of using RF technology is that RF signals are not blocked by obstructions in a similar manner as line of sight systems (IR based). However, one of the disadvantages of RF based systems is that RF signals are susceptible to interference, such as attenuation by objects, and multiple reflections. The attenuation of excitation signals 574, 576, 578 or multiple reflections of excitation signals 574, 576, 578 may introduce errors into the calculation of the location of badge 502. (Attenuation and multiple reflections effect calculations based on signal strength. Multiple reflections effect calculations based on timing information.)

Figure 16:
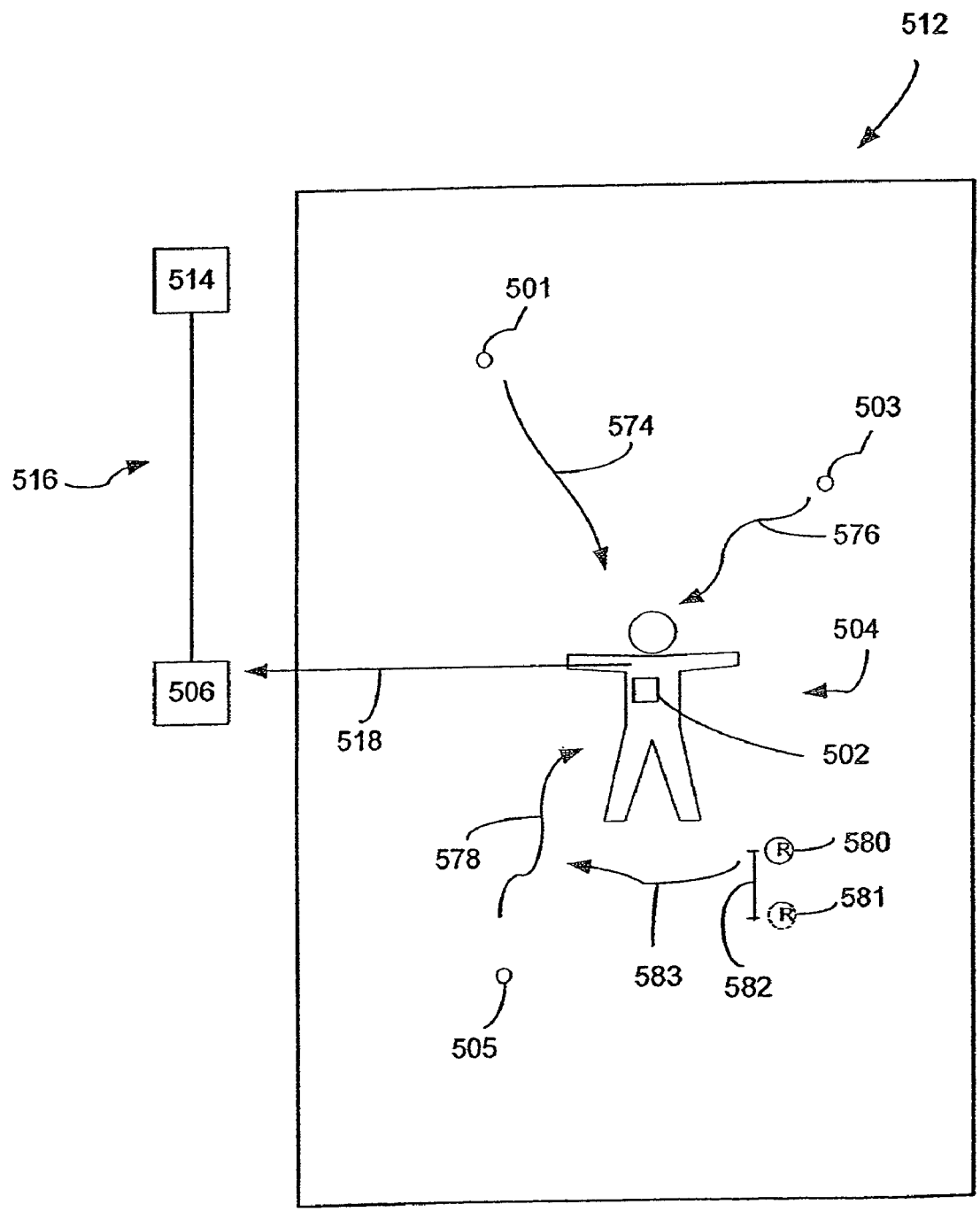
FIG. 16 illustrates the interactions between a fixed receiver and multiple fixed pingers of the exemplary locating and tracking system of FIG. 11.

Referring to FIG. 16, locating system 500 further includes a fixed location transceiver 580 positioned in area 512. Fixed transceiver 580 knows its location relative to fixed pingers 501, 503, 505. Fixed transceiver 580 is configured to receive excitation signals 574, 576, 578 and to determine distance measurements to pingers 501, 503, 505 and a calculated location, shown illustratively as transceiver 581 in FIG. 16. Transceiver 580 generates an ID signal 583 which is received by transceiver 506 and includes at least an indication of the calculated location 581 of transceiver 580.

As shown in FIG. 16 the calculated location 581 of transceiver 580 is displaced from the known location of transceiver 580 by a distance 582. The difference between the calculated location 581 and the true location of transceiver 580 may be caused by interference or multiple reflections or both. However, by knowing the error distance 582 introduced in the location of transceiver 580, a better estimate of the location of badge 502 may be made by central computing device 514. That is, the calculated location of badge 502 may be offset by a distance corresponding to distance 582.

In one embodiment of locating system 500, the above enumerated examples use RF for transmitting both excitation signals if needed and ID signals. Further, ultra-wideband technology (UWB) may be used to assist in minimizing the effects of interference and multiple reflections.

Figure 17:
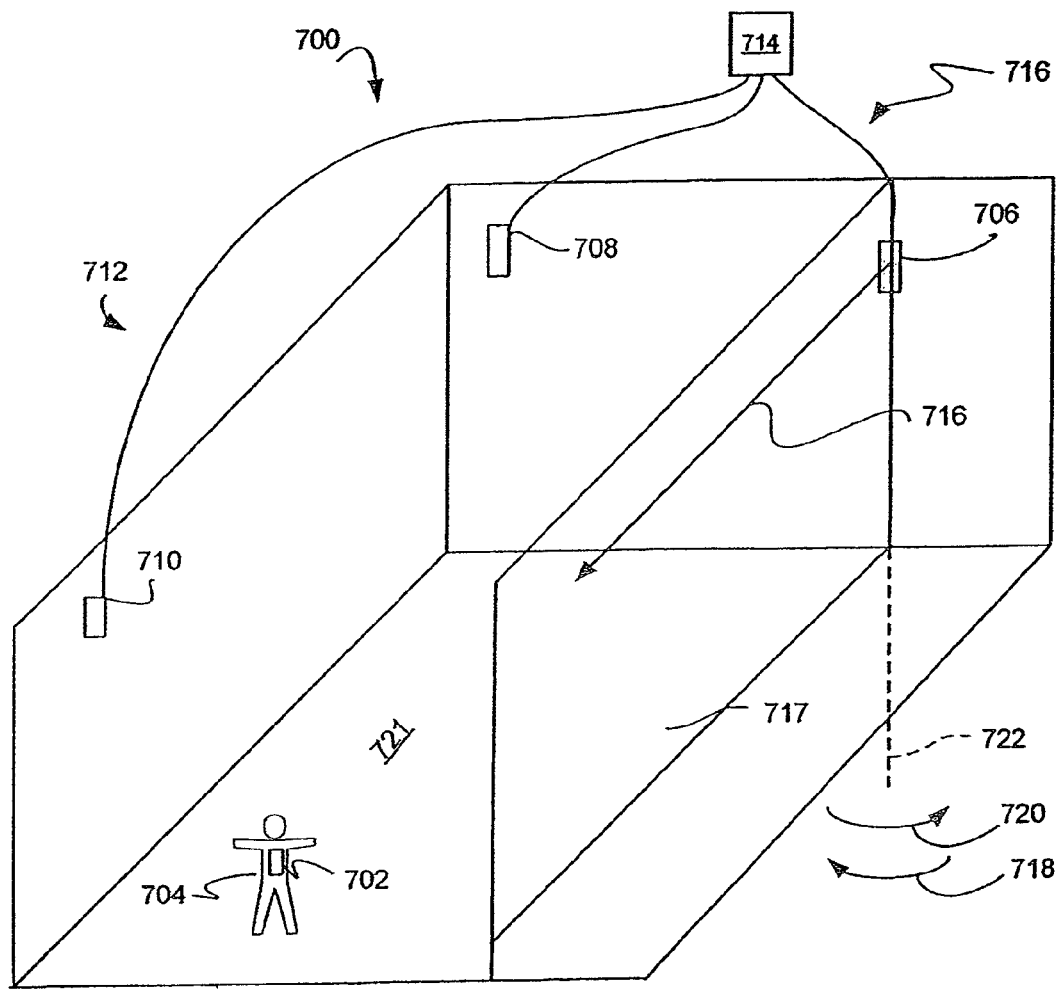
FIG. 17 illustrates another exemplary locating and tracking system of the present invention including at least one steerable antenna.
Figure 18:
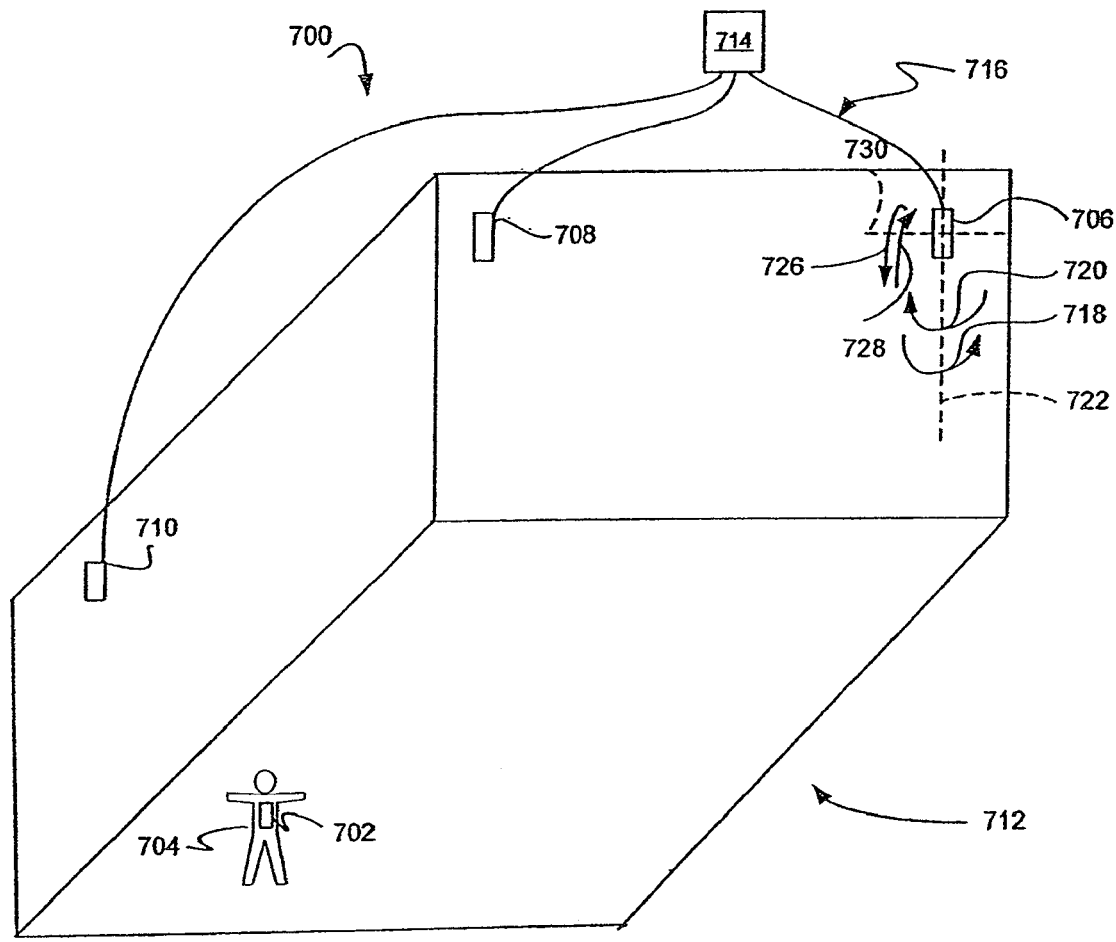
FIG. 18 illustrates that the at least one steerable antenna is steerable along multiple directions.
Figure 19:
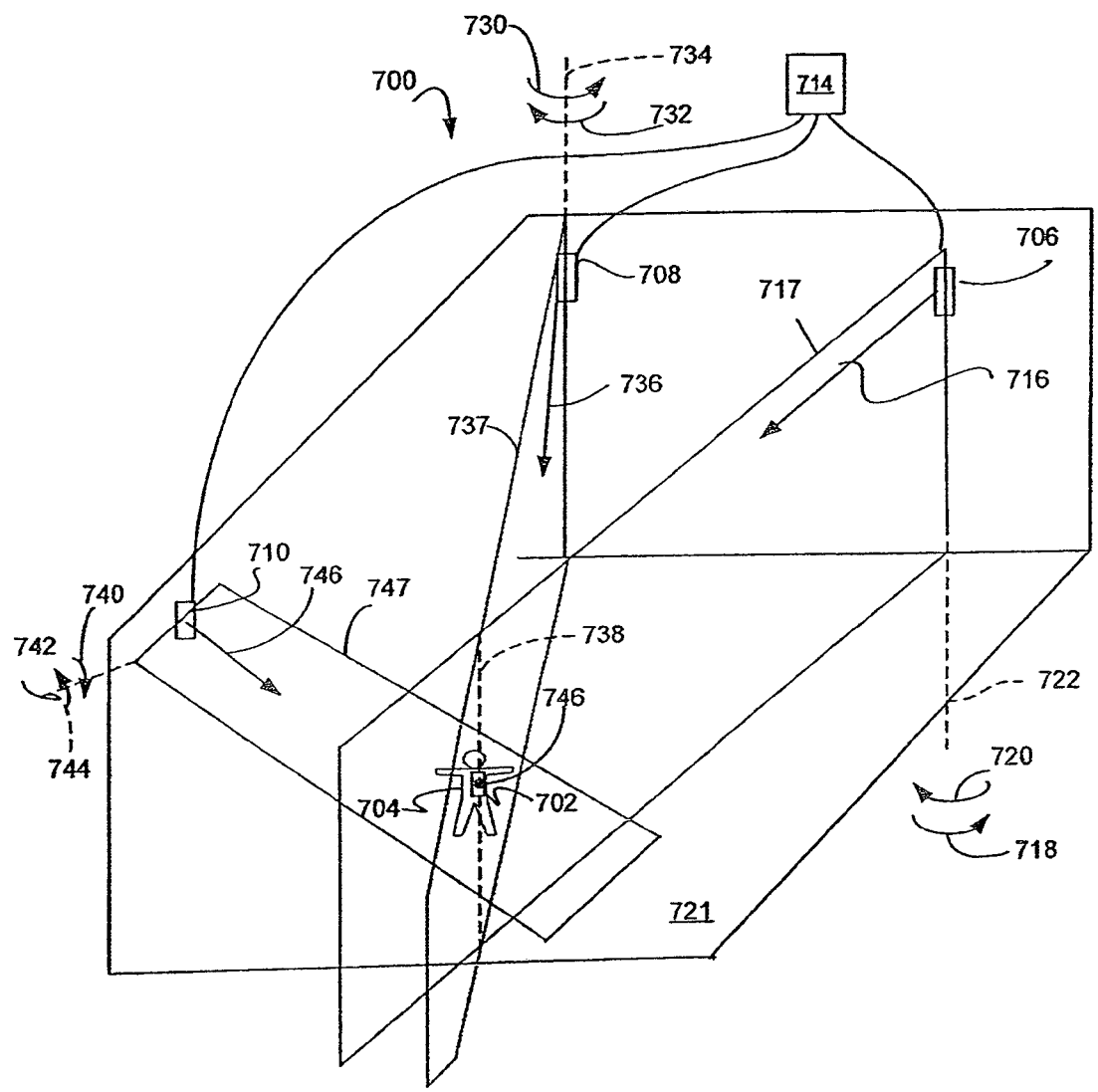
FIG. 19 illustrates a method of locating an asset in two dimensional space and three dimensional space with the system of FIG. 17.

Another exemplary locating system is shown in FIGS. 17-19. Locating system 700 includes one or more transceivers 706, 708, 710. Each transceiver 706, 708, 710 is configured to generate a signal which is detectable by a badge 702 which is associated with an asset 704. In one example, the signal generated by transceivers 706, 708, 710 is an excitation signal which causes badge 702 to generate an ID signal including a unique ID associated with asset 704.

Referring to FIG. 17, transceivers 706, 708, 710 are positioned within a room 712. Transceivers 706, 708, 710 are configured to generate an excitation signal in a specified direction based on the geometry of the respective transceiver, such as generally normal to the front of the respective transceiver. As shown in FIG. 17, transceiver 706 generates an excitation signal generally in direction 716. The excitation signal generated by transceiver 706 is of limited extent in substantially one dimension. As illustratively shown in FIG. 17, the excitation signal is generally defined by a plane 717 that is generally normal to floor 721 of area 712. As such, badge 702 receives the excitation signal generated by transceiver 706 regardless of its altitude if badge 702 is positioned in plane 717 along direction 716 relative to transceiver 706.

If badge 702 is so positioned, then badge 702 acknowledges the reception of the excitation signal by emitting an ID signal including the ID associated with the badge 702. However, if badge 702 is not positioned relative to transceiver 706 along direction 716, then badge 702 would not receive the excitation signal from transceiver 706 and therefore would not generate an ID signal. (It is understood that badge 702 might generate an ID signal in response to being in line with one of the other transceivers 708 and 710.)

Based on either the signal strength of at least one of the excitation signal and the ID signal or the time delay between the generation of the excitation signal and the reception of the ID signal from badge 702, transceiver 706 or computing device 714 is able to calculate the depth or distance from transceiver 706 to badge 702. Further, by knowing the direction, such as direction 716, associated with the emission of the excitation signal, transceiver 706 or computing device 714 is able to determine a two-dimensional position of badge 702 in room 712.

In one variation, transceivers 706, 708, 710 are steerable, for example, about an axis such that the direction of the respective excitation signal can be changed over time. As such, a two dimensional location, such as the position of badge 702 over floor 721 regardless of altitude is roughly determined by sweeping a transceiver's excitation signal through room 712 and recording the direction corresponding to badge 702 and the depth of badge 702 within room 712 based on the time between generation of the excitation signal and the reception of the badge ID signal or based on the signal strength of at least one of the excitation signal and the ID signal. As shown in FIG. 17, transceiver 706 is sweepable in directions 718, 720 about an axis 722. It should be appreciated that in this variation locating system 700 only requires a single transceiver, such as transceiver 706, to determine a two dimensional location of badge 702 since a single transceiver can cover the entire area 712 by sweeping through area 712 and since the depth of badge 702 can be determined by either signal strength or timing information. However, additional transceivers, such as transceivers 708, 710, may be used to increase the accuracy of locating system 700.

In one example, transceivers 706, 708, 710 are mechanically steerable, such as by securing each transceiver 706, 708, 710 to a base (not shown) which is rotatable using a controller (not shown). In another example, transceivers 706, 708, 710 are steerable using MEMS technology, such as by electrically actuating a plurality of directional transmitters formed on a wafer of each transceiver 706, 708, 710. In yet another example, transceivers 706, 708, 710 are both mechanically and electronically steerable.

In another variation, the excitation signal generated by transceiver 706 is of limited extent in two dimensions and the position of badge 702 in area 712 is determined by sweeping at least one transceiver, such as transceiver 706, in multiple directions. Badge 702 will generate an ID signal when it is generally positioned along a line defined by the direction of the excitation signal as opposed to the plane defined by the excitation signal in FIG. 17, since the excitation signal of this variation is of limited extent in two dimensions. As shown in FIG. 18, transceiver 706 is sweepable in directions 718, 720 about axis 722 and in directions 726, 728 about axis 730.

The direction of badge 702 relative to transceiver 706 is determined by sweeping transceiver 706 throughout room 712 and recording or otherwise denoting the direction corresponding to badge 702. The depth of badge 702 within room 712 is based on the time between generation of the excitation signal and the reception of the badge ID signal or is based on the signal strength of at least one of the excitation signal and the ID signal. It should be appreciated that in this variation, locating system 700 only requires a single transceiver, such as transceiver 706, to determine a three dimensional location of badge 702 since a single transceiver can cover the entire area 712 by sweeping through area 712 in multiple directions and since the depth of badge 702 can be determined by either signal strength or timing information. However, additional transceivers, such as transceivers 708, 710, may be used to increase the accuracy of locating system 700.

In a further variation, transceivers 706, 708, 710 and/or central computing device 714 do not rely on signal strength information or timing information to determine either a two-dimensional location or a three-dimensional location of badge 702 in area 712. Referring to FIG. 19, transceiver 706 is configured to be steerable in directions 718, 720 about an axis 722 and transceiver 708 is configured to be steerable in directions 730, 732 about an axis 734. Further, both transceiver 706 and transceiver 708 are configured to generate an excitation signal that is of limited extent in one dimension. As illustratively shown in FIG. 19, plane 717 generally defines the extent of the excitation signal of transceiver 706 generally along a direction 716 and a plane 737 generally defines the extent of the excitation signal of transceiver 708 generally along a direction 736. Both planes 717, 737 are generally normal to floor 721 of area 712.

If badge 702 is positioned relative to transceiver 706 within plane 717, then badge 702 acknowledges the excitation signal from transceiver 706 by generating an ID signal. However, if badge 702 is not so positioned, then badge 702 would not receive the excitation signal from transceiver 706 and therefore would not generate an ID signal. Similarly, if badge 702 is positioned relative to transceiver 708 within the plane including direction 736, then badge 702 acknowledges the excitation signal from transceiver 708 by generating an ID signal. However, if badge 702 is not so positioned, then badge 702 would not receive the excitation signal from transceiver 708 and therefore would not generate an ID signal.

In one example, the excitation signals generated by transceivers 706, 708 each include a transceiver ID which is unique to the respective transceiver. Further, the ID signal generated by badge 702 includes both a unique ID that is associated with asset 704 and the received transceiver ID signal. As such, transceivers 706, 708 can determine to which excitation signal badge 702 is responding.

In order to locate badge 702 in two dimensions, transceivers 706, 708 sweep area 712 with their respective excitation signals until an ID signal is generated by badge 702, indicating that badge 702 is along either direction 716 or 736. When transceiver 706 receives an ID signal corresponding to its excitation signal, transceiver 706 records or otherwise denotes the direction corresponding to badge 702. Similarly, when transceiver 708 receives an ID signal corresponding to its excitation signal, transceiver 708 records or otherwise denotes the direction corresponding to badge 702. As illustratively shown in FIG. 19, badge 702 is positioned along direction 716 relative to transceiver 706 and along direction 736 relative to transceiver 708. Based on a knowledge of the location of transceivers 706, 708 and the directions 716, 736, central computing device 714 is able to apply known mathematical techniques to determine that badge 702 is located somewhere along the intersection of planes 717, 737. Therefore, the location of badge 702 is somewhere along line 738.

In order to locate badge 702 in three dimensions, one of three methods may be used. First, at least one of transceivers 706, 708 may be configured to determine the depth of badge 702 relative to the respective transceiver, of transceivers 706, 708. The determined depth of badge 702 corresponds to two separate locations on line 738 creating an ambiguity. In a first example, the ambiguity is removed because transceivers 706, 708 are generally located above potential locations of badge 702. In such a situation only a single transceiver is needed to determine the depth of badge 702 because the single transceiver or central computing device 714 can eliminate any ambiguity by restricting the location of badge 702 to be lower than the respective transceiver or within area 712. In a second example, the ambiguity is removed because both transceivers 706, 708 are configured to determine the depth of badge 702. The approximate location of badge 702 is then determined based on the depths calculated by both transceivers 706, 708.

Second, at least one of transceivers 706, 708 is configured to be steerable in multiple directions and to limit the extent of the respective excitation signal in two dimensions. As described above in connection with FIG. 18, transceiver 706 may be configured to be is steerable in directions 718, 720 about axis 722 and in directions 726, 728 about axis 730. As such, badge 702 may be located in three dimensions by steering transceivers 706, 708 in directions 718, 720 and directions 730, 732, respectively. Once transceiver 706 receives an ID signal from badge 702, transceiver 706 may limit the extent of the respective excitation signal in two dimensions and steer in directions 726, 728 to determine an altitude of badge 702 along line 738.

Third, at least three transceivers, each steerable about at least one axis, are positioned in area 712, such as transceivers 706, 708, 710. As discussed above transceivers 706, 708 are able to locate badge 702 in two dimensions at the intersection of planes 717, 737. Transceiver 710 is configured to be steerable in directions 740, 742 about an axis 744 and to generate an excitation signal. A plane 747 generally defines the extent of the excitation signal of transceiver 710 generally along a direction 746. By knowing the direction 746 which corresponds to badge 702 receiving the excitation signal from transceiver 710 and subsequently generating an ID signal, the location of badge 702 along line 738 may be narrowed to generally a point 746.

Figure 20:
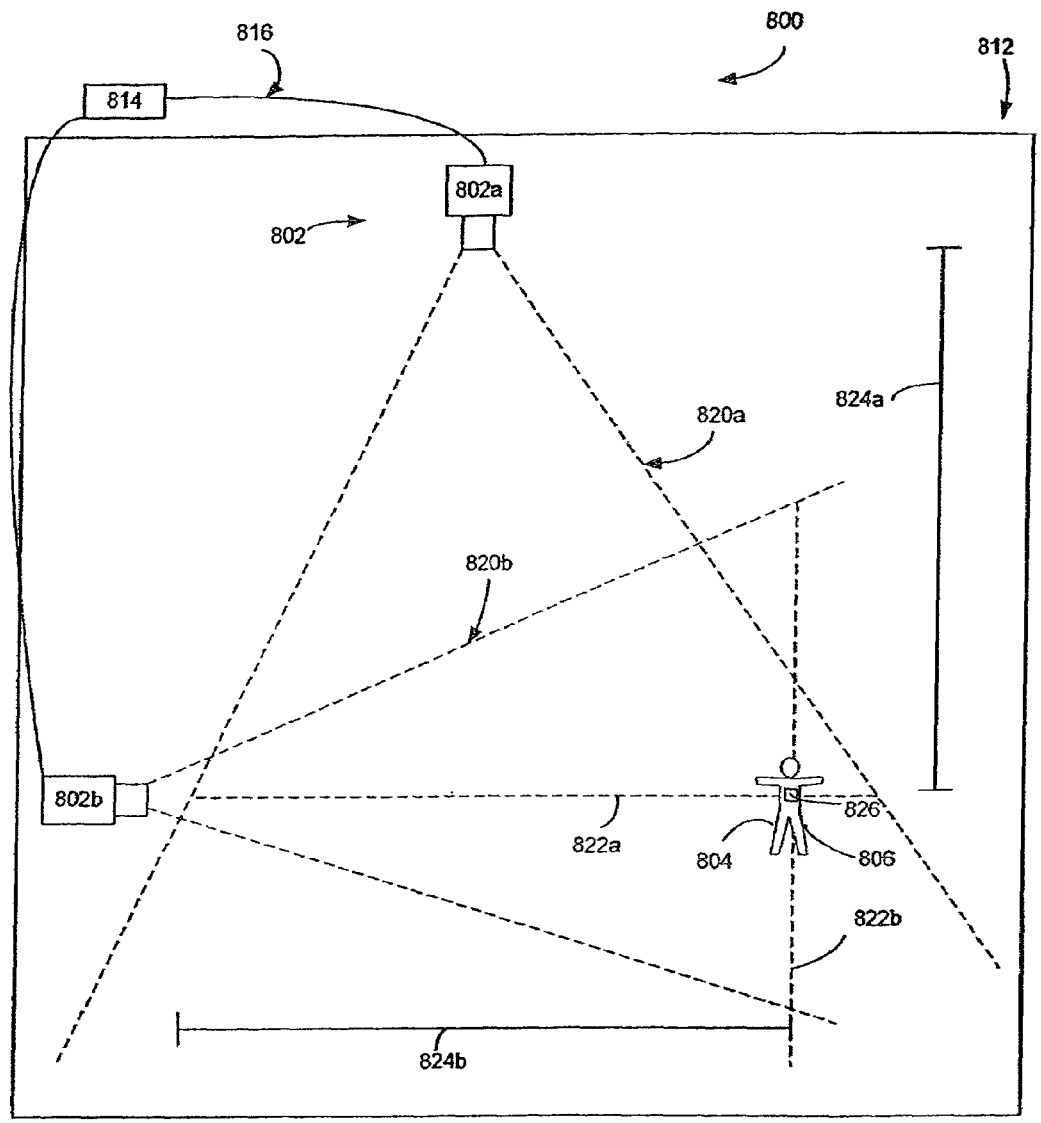
FIG. 20 illustrates a further exemplary locating and tracking system of the present invention including at least one camera.
Figure 21:
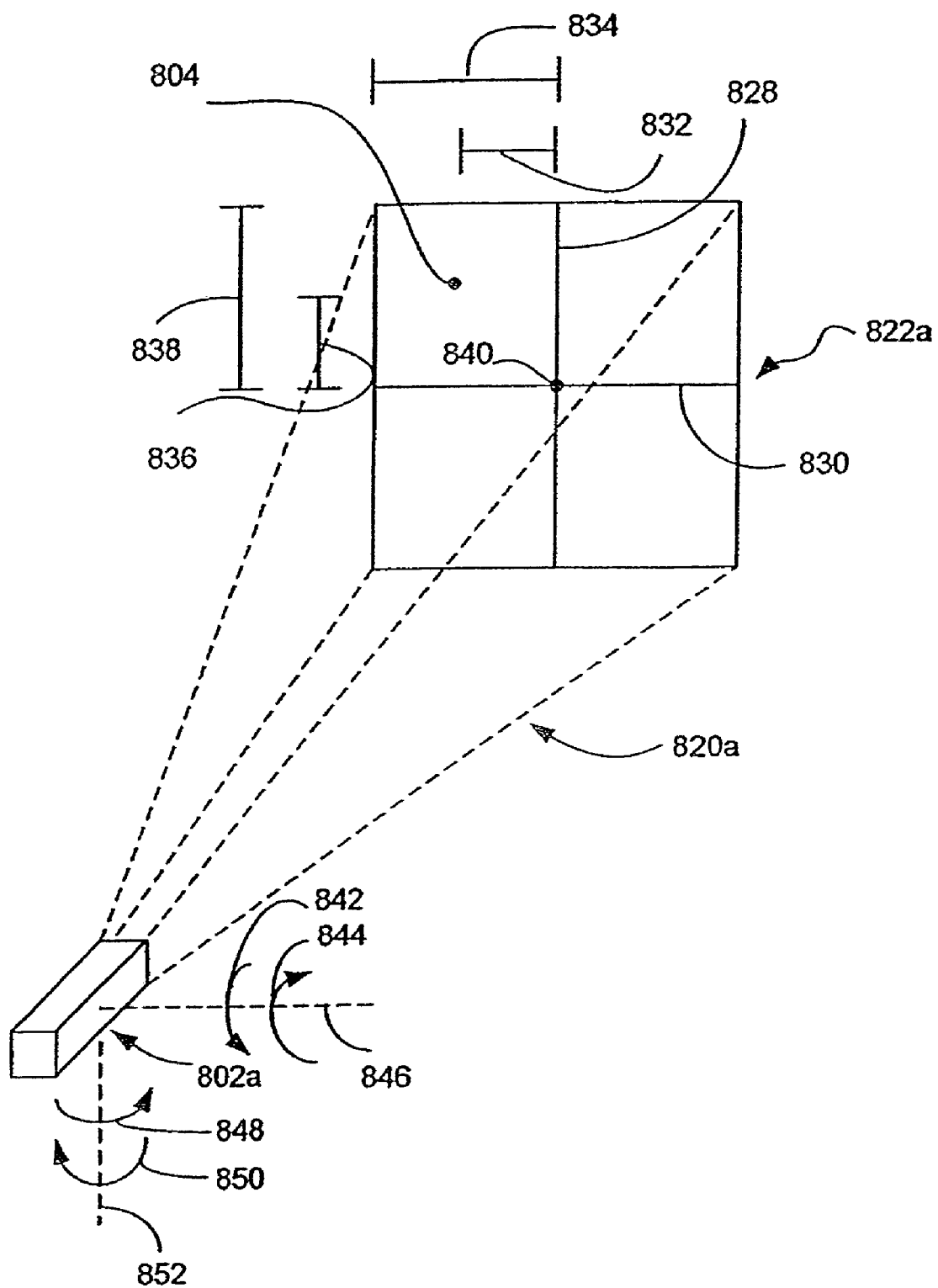
FIG. 21 illustrates a method of locating an asset in two dimensional space and three dimensional space with the system of FIG. 20.

Another exemplary locating system is shown in FIGS. 20-21. Locating system 800 includes one or more cameras 802, such as cameras 802a and 802b which are positioned within an area of interest, such as a room 812. Cameras 802 are configured to detect the presence of an indicator 804 corresponding to an asset 806. Example indicators include the color of clothing being worn by an individual, a badge or name plate associated with an individual or equipment, a temperature characteristic, such as a heat image associated with a person, etc.

In one example, indicator 804 is a badge or nameplate. Camera 802 is configured to detect the presence of badge 804 based on a characteristic of badge 804, such as color or emission. Known image processing techniques can be implemented by camera 802 and/or central computing device 814 to detect the presence of badge 804. Further, camera 802 may be configured to capture an image of the face of a person associated with a badge such that conventional image recognition techniques may be used to determine the identity of the person.

Camera 802 is further configured to adjust the focal length associated with camera 802 to bring badge 804 into focus. Badge 804 may include writing or other markings that are viewable by camera 802. Based on the focal length of camera 802, the depth or distance of badge 804 from camera 802 can be determined. For example, assuming the optics of camera 802 may be represented as a thin-lens, the depth of badge 804 relative to camera 802 may be approximately calculated by equation (5)

$$z_1 = 1/((1/f)-(1/z_2)) \quad (5)$$

wherein $z_1$ is the depth of an object plane containing badge 804, f is the focal length of camera 802 and $Z_2$ is the distance to an image plane of camera 802 which is assumed to be a fixed value. As such, once badge 804 is detected by camera 802, the depth of badge 804 can also be calculated.

In one example, the location of badge 804 in two dimensions may be determined from the depth calculations of two cameras 802a, 802b positioned at an angle to each other. As shown in FIG. 20, cameras 802a, 802b are generally at a right angle to each other. However, cameras 802a, 802b may be placed at any angle relative to each other except for 180. degree. As shown in FIG. 20, badge 804 is located within a field of view 820a of camera 802a and within a plane 822a a distance 824a from camera 802a. Similarly, badge 804 is located within a field of view 820b of camera 802b and within a plane 822b a distance 824b from camera 802b. The location of badge 804 may be determined in two dimensions based on calculating an intersection 826 of object planes 824a, 824b of cameras 802a, 802b, respectively.

In another example, a single camera such as camera 802a may be used to determine the location of badge 804 in two dimensions or in three dimensions. Referring to FIG. 21, an illustration of object plane 822a (corresponding to the plane determined to contain badge 804 based on the focal length of camera 802a) of camera 802a is shown. At this point, locating system based solely on camera 802a knows the location of badge 804 in one dimension, a depth from camera 802a. The location of badge 804 in a second and a third dimension may be determined by several methods.

In a first method, the location of badge 804 in at least either a second dimension or in a second dimension and a third dimension may be based on the location of badge 804 in object plane 822a. As shown in FIG. 21, badge 804 is positioned to the left of a vertical centerline 828 of object plane 822a and above a horizontal centerline 830 of object plane 822a. The horizontal position or dimension of badge 804 is determined by calculating a horizontal offset percentage associated with badge 804. The offset percentage is calculated by dividing the horizontal offset of badge 804 from vertical centerline 828, as represented by the number of pixels 832 by the total half field view number of pixels 834. The offset percentage is then multiplied by a known distance value for the half field of view in the horizontal extent of camera 802 a to determine the distance badge 804 is from vertical centerline 828 of camera 802a. As such, by knowing the direction of camera 802a, badge 804 may be located in two dimensions.

To locate badge 804 in three dimensions a vertical position or dimension of badge 804 in object plane 822a must be determined in addition to the horizontal position or dimension of badge 804 and the depth of badge 804. The vertical position or dimension of badge 804 is determined by calculating a vertical offset percentage associated with badge 804. The vertical offset percentage is calculated by dividing the vertical offset of badge 804 from horizontal centerline 830, as represented by the number of pixels 836 by the total half field view number of pixels 838 in the vertical extent of object plane 822a. The vertical offset percentage is then multiplied by a known distance value for the half field of view in the vertical extent of camera 802 a to determine the distance badge 804 is from horizontal centerline 830 of camera 802a. As such, by knowing the direction of camera 802a, badge 804 may be located in three dimensions.

In a second method, the location of badge 804 in at least either a second dimension or in a second dimension and a third dimension may be based on the direction of camera 802a corresponding to badge 804 being coincident with a centerline 828, 830 or center point 840 of object plane 822a. Camera 802a is configured to be mechanically steerable in at least one direction. Referring to FIG. 21, in one example camera 802a is steerable in directions 848, 850 about an axis 852. To determine a second dimension related to badge 804, camera 802a is steered until badge 804 is aligned with vertical centerline 828 of object plane 822a. Based on the direction of camera 802a and the depth of badge 804, the location of badge 804 may be determined in two dimensions. In another example, camera 802a is steerable in directions 848, 850 about axis 852 and is steerable in directions 842, 844 about an axis 846. Camera 802a is steered about axes 846, 852 until badge 804 is generally aligned with center point 840 of object plane 822a. Therefore, based on the direction of camera 802a and the depth of badge 804, the location of badge 804 may be determined in three dimensions.

In another embodiment, cameras 802a and 802b may be replaced with a plurality of scanning lasers mounted on one or more surfaces of room 812, and badge 804 may be replaced with a tag or label including a bar code indicator that identifies the associated asset. In such an embodiment, the lasers are movably mounted to surfaces in room 812 and electronically controlled to collectively scan the entire room 812 to detect and read the bar code using conventional bar code technology or other suitable techniques. In this manner, the asset associated with the bar code may be identified regardless of its location in room 812, so long as the bar code is within the line-of-sight of the scanning lasers.

In yet another embodiment, a plurality of lasers are arranged in fixed locations around room 812. Each laser is configured to detect interference caused by objects when objects pass through the beam of the lasers. The lasers may be situated at known angles relative to one another to permit two or three dimensional detection of objects. For example, a first plurality of laser may be located in a substantially horizontal row along one wall of room 812, and a second plurality of lasers may be located in a substantially horizontal row along a second wall of room 812 that is perpendicular to the first wall. When an asset passes through the various beams of the lasers and causes detectable interference, a computing device coupled to the lasers is configured to determine which laser(s) detect the interference. Since the position of each laser is known, the computing device is able to determine a two dimensional location of the asset. It should be understood that the lasers may further be configured to sweep vertically to detect interference caused by assets, regardless of the altitude of the asset. Additionally, a third plurality of lasers may be added, arranged in a substantially vertical column on one wall of room 812 and configured to sweep horizontally, to determine the altitude of the asset according to principles described above, and provide a three-dimensional location of the asset. Moreover, any of the identification techniques described herein may be used with this variation of the invention to identify the asset in addition to determining its location.

Figure 22:
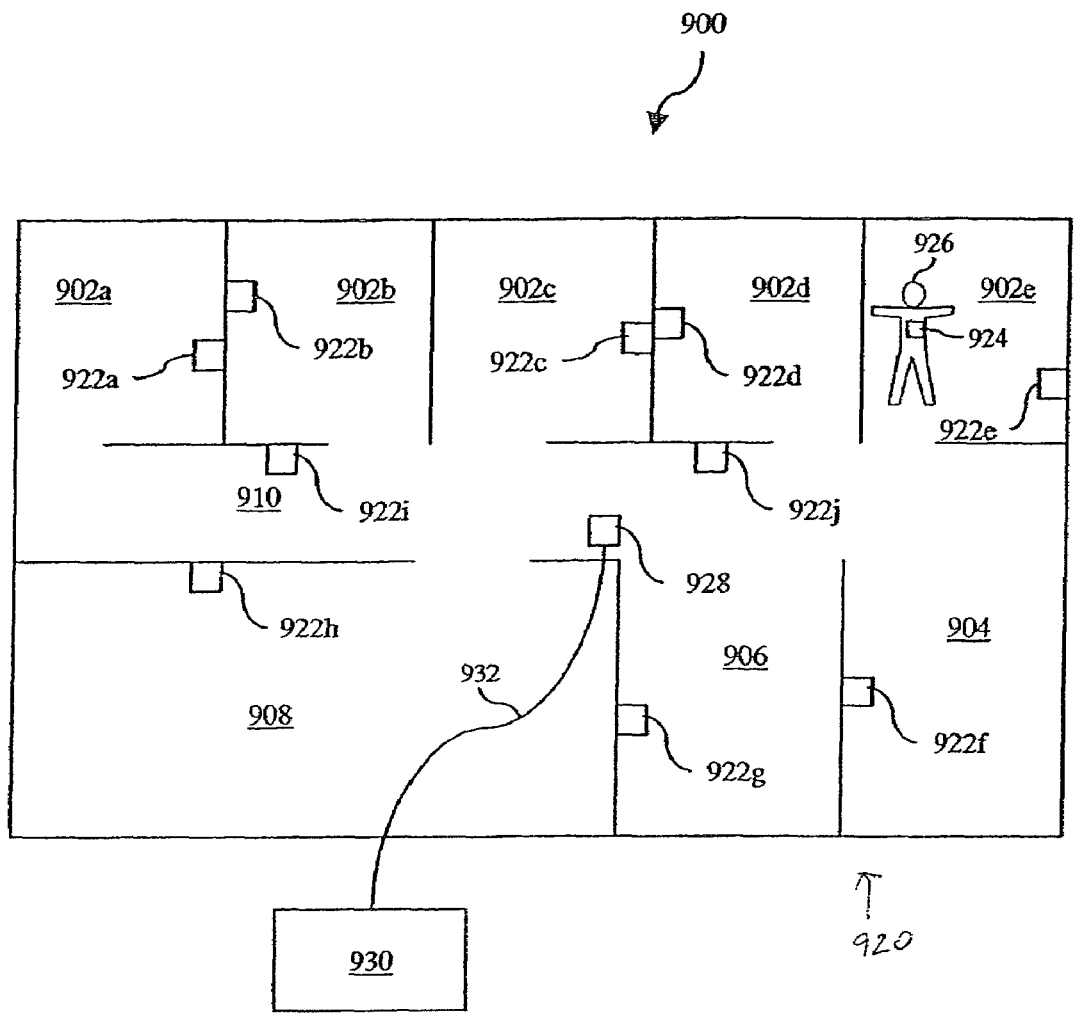
FIG. 22 illustrates yet another exemplary locating and tracking system of the present invention.

Another exemplary locating system is shown in FIG. 22. Referring to FIG. 22, a facility 900, such as a healthcare facility, includes a plurality of areas, such as patient rooms 902a-e, waiting room 904, nurse station 906, and break room 908, all connected by a hallway 910. Facility 900 includes a locating system 920 including a plurality of transmitters positioned throughout facility 900, such as transmitters 922a-j, at least one badge 924 associated with an asset 926, a receiver 928, and a central computing device 930.

Transmitters 922a-j are configured to generate an ID signal (not shown) containing a unique ID associated with the respective transmitter 922a-j. The transmitter ID may be set by the setting of a conventional dip switch associated with each of transmitters 922a-j. In one example, transmitters 922a-j include one of an IR transmitter, an ultrasound transmitter, or other line-of-sight transmitter. In another example, transmitters 922a-j include a low-frequency RF transmitter. Transmitters 922a-j, in one example, include a battery (not shown) to provide power to generate the respective ID signal. In another example, transmitters 922a-j are coupled to a power supply (not shown) such as a facility electrical system.

Badge 924 is configured to receive the ID signal generated by transmitters 922a-j when badge 924 is proximate to one of transmitters 922a-j. Referring to FIG. 22, badge 924 receives the ID signal generated by transmitter 922e because badge 924 is located in patient room 902e. Badge 924 is generally similar to badge 12 and is configured to generate an ID signal associated with badge 924. The badge ID signal includes an ID unique to badge 924 (asset 926) and at least the last received transmitter ID from one of transmitters 922a-j. In one example, badge 924 generates an ID signal every time badge 924 receives a new transmitter ID, such as when badge 924 leaves patient room 902e and enters hallway 910 proximate to transmitter 922j. In another example, badge 924 generates a badge ID signal at a predetermined interval and includes all transmitter IDs received since the previously transmitted badge ID signal. In yet another example, badge 924 transmits the badge ID signal at two or more predetermined time intervals based on a characteristic of a displacement sensor (not shown) associated with badge 924. In the above examples, badge 924 is configured to store one or more transmitter IDs for later transmission in a badge ID signal.

Badge 924 includes an RF transmitter or other transmitter that is capable of sending the badge ID signal to receiver 928 which may be centrally located in facility 900. As such, the transmitter associated with badge 924 must be capable of penetrating facility walls and other obstructions. Receiver 928 is connected to central computing device 930 through either a wired or wireless connection, represented in FIG. 22 as 932.

The location of transmitters 922a-j are stored in or otherwise made available to central computing device 930. As such, the location of badge 924 is determined by correlating the transmitter ID(s) transmitted with the badge ID signal with the known locations of transmitters 922a-j. Central computing device 930 stores the location information related to badge 924 for later processing or retrieval.

Figure 23:
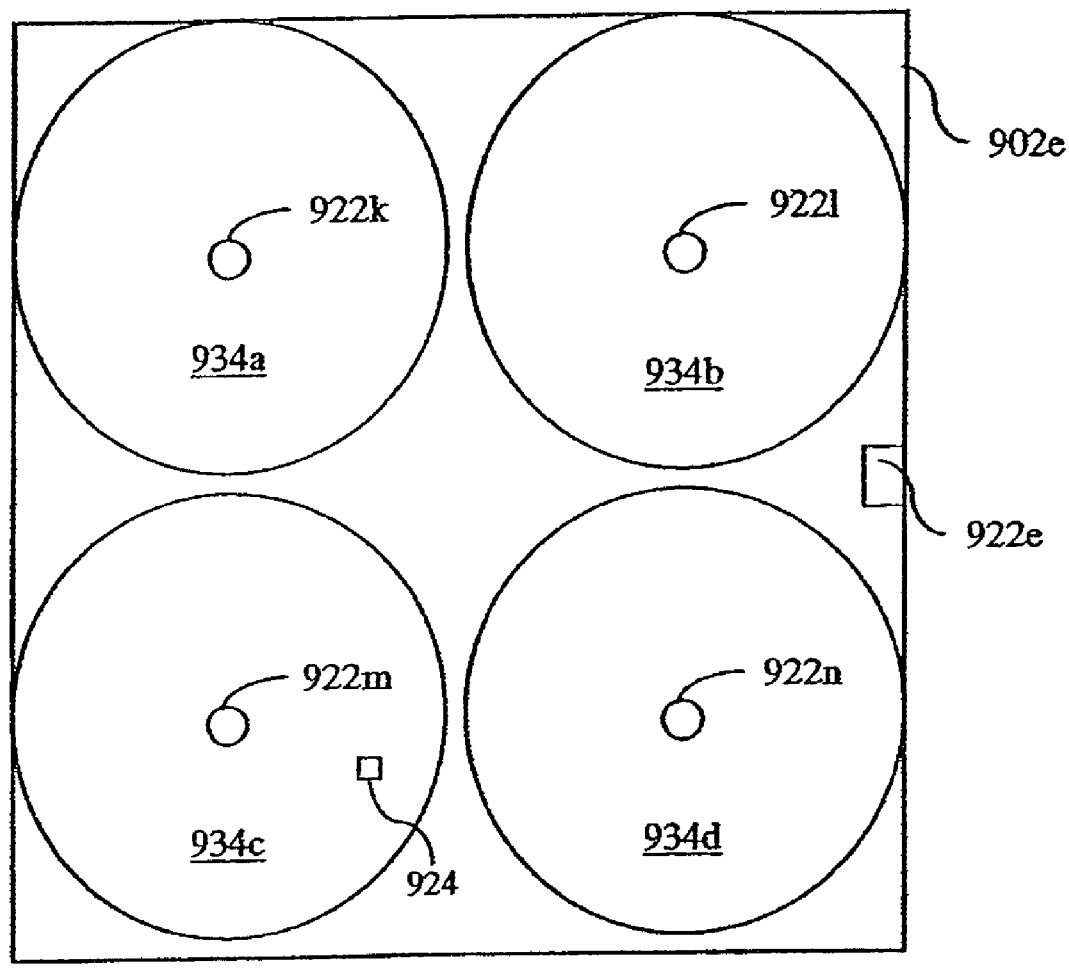
FIG. 23 illustrates exemplary zones of transmitters in the locating and tracking system of FIG. 22.

Referring to FIG. 23, patient room 902e is shown with transmitter 922e and additional transmitters 922k-n. Transmitters 922k-n, like transmitter 922e, generate a transmitter ID signal which is received by badge 924. However, transmitters 922k-n generate their respective transmitter IDs in limited areas, 934a-d respectively, of patient room 902e. As such, badge 924 only receives an ID signal from transmitters 922k-n if badge 924 is within a respective area of one of transmitters 922k-n. For example, as shown in FIG. 23, badge 924 will receive an ID signal from transmitter 922m, but not from transmitters 922k,l,n. As such, locating system 900 not only knows that badge 924 is in patient room 902e, due to transmitter 922e or 922m, but also that badge 924 is in region 934c of patient room 902e corresponding to transmitter 922m. Therefore transmitters 922k-n increase the resolution of locating system 900 over transmitters 922a-j. It should be understood that transmitter 922e is optional in light of transmitters 922k-n.

Regions 934a-d are shown in FIG. 23 to be mutually exclusive regions. However, it is within the scope of the present invention that one or more of regions 934a-d may overlap one or more of the other regions 934a-d. As such, badge 924 at a given location may receive a transmitter ID signal from one or more of transmitters 922k-n. When badge 924 receives a transmitter ID signal from more than one of transmitters 922k-n, the techniques for determining the location of badge 924 relative to the multiple transmitters of transmitters 922k-n based on at least one of signal strength and timing information may be implemented in locating system 900.

In one example, transmitters 922k-n are RF transmitters which generate their respective ID signals at a low frequency, such as about 125 KHz. In one case transmitters 922k-n are mounted to a ceiling of patient room 902e and generate their respective ID signals in a region about six feet below the ceiling and in about a three foot radius of the respective transmitter 922k-n. In one example, badge 924 includes an RF transmitter which is capable of sending a badge ID signal to receiver 928 over a distance of about 200 to 300 feet.

One feature of locating system 900 is that a network connecting transmitters, receivers, or transceivers in every location of facility 900 is not required. This may reduce the cost associated with implementing locating system 900 into an existing facility.

It should be understood that various signals other than conventional electronic signals may be used to locate and track assets consistent with the teachings of the various embodiments of the invention described above. For example, badges may be configured to maintain a particular temperature or temperature characteristic which, when detected by sensors permits location of the asset associated with the badge. Conventional thermal imaging technology may be employed to identify certain distinguishing characteristics of badges, thereby permitting identification of the asset associated therewith. Additionally, the badge may be configured to maintain a temperature corresponding to the asset such that the locating and tracking system can also determine the temperature of the tracked asset. Such temperature information may be used to trigger activities. For example, if a sink is a tagged asset, an alarm may be activated if the sink temperature exceeds a predetermined threshold.

The location information collected and processed by any of the above mentioned location systems 10, 500, 700, 800, 900 can be used in applications designed to improve the level of care provided to patients in a hospital, reduce the demands on hospital staff, and/or maximize the efficiency of the healthcare environment. For instance, as explained above in connection with ABT 10, the collected location information can be used to determine handwashing compliance, to easily locate assets, to determine waste handling compliance, to associate assets with particular patients, to provide data for healthcare environment simulations, and many more applications. Additionally, many of the locating and tracking techniques described herein may be employed to track assets, such as laboratory test results, through pneumatic systems. In such an application, the locating and tracking system may determine, for example, exactly where in the tubing network of the pneumatic system a particular asset (e.g., specimens or results of a particular patient) are located (or lodged).

While the invention has been illustrated and described in detail in the drawings and foregoing description, such illustration and description is to be considered as exemplary and not restrictive in character, it being understood that only exemplary embodiments have been shown and described and that all changes and modifications that come within the spirit of the invention and the attached claims are desired to be protected.

What is claimed is:

1. A method for monitoring an asset to determine if the asset has been dropped or has fallen, the method comprising the steps of:
    providing a badge adapted to be coupled to the asset, the badge having an accelerometer configured to monitor a vertical acceleration of the asset and a transmitter;
    monitoring the vertical component of the acceleration of the badge;
    transmitting information regarding the vertical acceleration of the badge;
    determining if the vertical acceleration of the badge has exceeded a threshold value, wherein the step of determining if the vertical acceleration of the badge has exceeded the threshold value is performed by a processor remote from the badge; and
    identifying the asset as having been dropped or as having fallen based on the vertical acceleration exceeding the threshold value.

2. The method of claim 1, further comprising the step of determining where the asset is located.

3. The method of claim 1, wherein the vertical acceleration component is used to determine a speed associated with the asset.

4. The method of claim 1, further comprising the step of initiating an alarm based on a determination that the asset has fallen or has been dropped.

5. The method of claim 1, further comprising the step of providing an indication to a caregiver associated with the asset that the asset has fallen or has been dropped.

6. The method of claim 1, further comprising the step of determining an estimated heading at which the asset traveled.

7. A system for monitoring an asset to determine if the asset has been dropped or has fallen, the system comprising:
    a badge adapted to be coupled to the asset, the badge having an accelerometer configured to sense a vertical acceleration of the asset and a transmitter; and
    a processor operable to execute software to monitor the vertical component of the acceleration of the badge which is transmitted from the badge, to determine if the vertical acceleration of the badge has exceeded a threshold value, and to identify the asset as having been dropped or as having fallen based on the vertical acceleration exceeding a threshold value, wherein the processor is located remotely from the badge.

8. The system of claim 7, wherein the processor is operable to determine where the asset is located.

9. The system of claim 7, wherein the vertical acceleration component is used to determine a speed associated with the asset.

10. The system of claim 7, wherein the processor is operable to activate an alarm based on a determination that the asset has fallen or has been dropped.

11. The system of claim 7, wherein the processor is operable to initiate a notification to a caregiver associated with the asset that the asset has fallen or has been dropped.

12. The system of claim 7, wherein the processor is operable to determine a heading at which the asset traveled.

* * * * *